(12) United States Patent
Takanashi et al.

(10) Patent No.: US 6,933,305 B2
(45) Date of Patent: Aug. 23, 2005

(54) AMIDE COMPOUNDS AND USE THEREOF

(75) Inventors: Shinichi Takanashi, Tokyo (JP); Yoichiro Naito, Tokyo (JP); Hiroshi Tanaka, Tokyo (JP); Masayoshi Uehata, Tokyo (JP); Koshiro Katayama, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 62 days.

(21) Appl. No.: 10/221,655

(22) PCT Filed: Mar. 16, 2001

(86) PCT No.: PCT/JP01/02132
§ 371 (c)(1),
(2), (4) Date: Oct. 21, 2002

(87) PCT Pub. No.: WO01/68607
PCT Pub. Date: Sep. 20, 2001

(65) Prior Publication Data
US 2003/0158413 A1 Aug. 21, 2003

(30) Foreign Application Priority Data
Mar. 16, 2000 (JP) ......................................... 2000-074764

(51) Int. Cl.⁷ .................. A61K 31/437; A61K 31/4436; C07D 471/04; C07D 409/12; A61P 9/12
(52) U.S. Cl. ....................... 514/300; 514/303; 514/337; 514/349; 546/113; 546/119; 546/280.1; 546/279.7; 546/282.7; 546/309
(58) Field of Search .......................... 546/280.1, 279.7, 546/309, 282.7, 119, 113; 514/303, 300, 337, 349

(56) References Cited

U.S. PATENT DOCUMENTS 6,218,410 B1 * 4/2001 Uehata et al. .............. 514/352

FOREIGN PATENT DOCUMENTS

| JP | 11-130751 | 5/1999 |
| JP | 2000-63274 | 2/2000 |
| WO | 98/06433 | 2/1998 |

OTHER PUBLICATIONS

Sasaki et al. Pharmacology & Therapeutics. 2002, 93:225–232.*

Loge et al. Journal of Enzyme Inhibition and Medicinal Chemistry, 2002, 17(6): 381–290.*

H. Nagumo et al., "Rho kinase inhibitor HA–1077 prevents Rho–mediated myosin phosphatase inhibition in smooth muscle cells", Am. J. Physiol. Cell. Physiol., vol. 278, No. 1, Jan. 2000, C57–65.

* cited by examiner

*Primary Examiner*—Evelyn Mei Huang
(74) *Attorney, Agent, or Firm*—Wenderoth, Lind & Ponack, L.L.P.

(57) ABSTRACT

The present invention relates to an amide compound of the formula

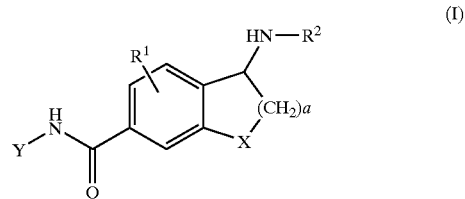

wherein $R^1$ is a hydrogen and the like, $R^2$ is a hydrogen and the like, X is $SO_2$ and the like, Y is the formula (III) and the like and a is 2, an isomer thereof or pharmaceutically acceptable salts thereof. The compound of the present invention shows a remarkable and selective Rho kinase inhibitory action, is free of problematic toxicity, shows fine oral absorption and drug kinetics (absorption, distribution, metabolism, excretion and the like of the drug), and shows superior properties (e.g., stability etc.) as a compound. Accordingly, it can be used as a therapeutic drug for various diseases in which Rho kinase is involved.

7 Claims, 1 Drawing Sheet

```
                                                                      Sequence Listing SEQ ID No:5
  477         Artificial Amino Acids
N   Q   R   N   L   A   L   E   H   H   H   H   H   H   *            Sequence Listing SEQ ID No:3
AAT CAA AGA AAT TTA GCA CTC GAG CAC CAC CAC CAC CAC CAC TAA CCT AGG TAG CTG
TTA GTT TCT TTA AAT CGT GAG CTC GTG GTG GTG GTG GTG GTG ATT GGA TCC ATC GAC  Sequence Listing SEQ ID No:4
                            Xho I
```

FIG. 1

SEQUENCE LISTING

<160> NUMBER OF SEQ ID NOS: 5

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide designed to act as primer for PCR

```
<400> SEQUENCE: 1
ccgagctcca tgtcgactgg ggacagtttt gag                          33

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide designed to act as primer for PCR

<400> SEQUENCE: 2
tagcggccgc actagttttt ccagatgtat ttttg                        35

<210> SEQ ID NO 3
<211> LENGTH: 60
<212> TYPE: DNA
<213> ORGANISM: Unknown
<220> FEATURE:
<221> NAME/KEY: CDS
<222> LOCATION: (1)..(45)
<223> OTHER INFORMATION: DNA sequence of part of expression vector of
      human ROCK-1 kinase domain having His-Tag sequence added
      to C-terminal

<400> SEQUENCE: 3 aat caa aga aga aat cta gca ctc gag cac cac cac cac cac cac   45
Asn Gln Arg Arg Asn Leu Ala Leu Glu His His His His His His
 1               5                  10                  15 taacctaggt agctg                                              60

<210> SEQ ID NO 4
<211> LENGTH: 60
<212> TYPE: DNA
<213> ORGANISM: Unknown
<220> FEATURE:
<223> OTHER INFORMATION: Description of Unknown Organism: Complementary
      strand to DNA sequence of Sequence Listing SEQ ID
      No:3

<400> SEQUENCE: 4 tta gtt tct tct tta gat cgt gag ctc gtg gtg gtg gtg gtg gtg   45 attggatcca tcgac                                              60

<210> SEQ ID NO 5
<211> LENGTH: 15
<212> TYPE: PRT
<213> ORGANISM: Unknown
<220> FEATURE:
<223> OTHER INFORMATION: Description of Unknown Organism: Amino acid
      sequence of part of human ROCK-1 kinase domain
      having His-Tag sequence added to C-terminal

<400> SEQUENCE: 5

Asn Gln Arg Arg Asn Leu Ala Leu Glu His His His His His His
 1               5                  10                  15
```

AMIDE COMPOUNDS AND USE THEREOF

The present application is a U.S. national stage of PCT/JP01/02132 filed Mar. 16, 2001.

TECHNICAL FIELD

The present invention relates to a novel amide compound having a Rho kinase inhibitory action. Moreover, the present invention relates to use of the compound as a pharmaceutical agent, a reagent or a diagnostic agent.

BACKGROUND ART

Ever since the discovery of Ras in 1981, a number of small GTP binding proteins (small G proteins) similar to Ras have been found, and many physiological functions they possess have been studied. These small. G proteins have a molecular weight of 20,000–30,000 and do not have a subunit structure. They all specifically bind GDP and GTP, and hydrolyze the thus-bound GTP (GTPase activity) (Hall, A., Science, 249, 635–640, 1990; Bourne, H. R. et al., Nature, 349, 117–127, 1991).

To date, more than 50 kinds of genes encoding these small G proteins have been found from yeast to mammals, forming a superfamily. These small G proteins are largely divided into 5 groups of Ras, Rho, Rab, Arf and others, according to the similarity of their amino acid sequences.

Of these, Rho was named so because its gene isolated in the form of cDNA from sea hare neuromuscle encodes a polypeptide having about 35% homology with Ras (Ras homologue) (Madaule, P., Cell, 41, 31–40, 1985).

Rho is specifically ADP ribosylated by C3 enzyme, which is one of the botulinum toxins, and Staphylococcal toxin EDIN, and inactivated (Narumiya, S. and Morii, S., Cell Signal, 5, 9–19, 1993; Sekine, A. et al., J. Biol. Chem., 264, 8602–8605, 1989). Hence, the C3 enzyme and EDIN were used to study the involvement of Rho in cell functions from various aspects.

For example, phosphorylation by myosin light chain (MLC) kinase is considered to enable actin-myosin interaction and initiate contraction of smooth muscle, and the structure of smooth muscle myosin phosphatase, which dephosphorylates MLC, has been clarified (Shimizu, H. et al., J. Biol. Chem., 269, 30407–30411). It has been clarified that the activity of myosin phosphatase is, like MLC kinase, under the control of the intracellular signal transduction system and Rho is involved in this mechanism. Moreover, an active Rho bound with GTP has been found to enhance Ca-dependent contraction in a smooth muscle skinned fiber specimen (Hirata, K., J. Biol. Chem., 267, 8719–8722, 1992), thereby suggesting that the increase in Ca sensitivity in smooth muscle contraction is caused by the inhibition of myosin phosphatase activity via Rho.

In Swiss 3T3 cell and 3Y1 cell, moreover, Rho-dependent promotion of tyrosine phosphorylation (Kumagai, N. et al., J. Biol. Chem., 270, 8466–8473, 1993) and activation of many kinds of serine/threonine kinases (Kumagai, N. et al., FEBS Lett., 366, 11–16, 1995) have been acknowledged. From this, the presence of plural protein kinases in the downstream of Rho in the signal transduction pathway via Rho has been suggested and, serine/threonine kinase (Rho kinase) activated along with the activation of Rho, such as ROCα (Leung, T. et al., J. Biol. Chem., 270, 29051–29054, 1995) [another name Rho-kinase, ROCK-II] and p160ROCK (Ishizaki, T. et al., EMBO J., 15, 1885–1893, 1996) [another name ROCKβ, ROCK-I], have been reported as one of the proteins that transduct signals from Rho.

In addition, it has been reported that this Rho kinase directly phosphorylates myosin phosphatase and inhibits its activity (Kimura, K. et al., Science, 273, 245–248, 1996).

In recent years, a certain kind of amide compound has been found to be a selective Rho kinase inhibitor (Uehata, M. et al., Nature, 389, 990–994, 1996, WO 98/06433), and further, certain kinds of isoquinoline sulfonamide derivatives (WO 98/06433) and isoquinoline derivatives (Naunyn-Schmiedeberg'S Archives of Pharmacology 385(1) Suppl. R219 1998, 11) have been found to be Rho kinase inhibitors.

In addition, certain kinds of vinylbenzene derivatives such as ethacrynic acid, 4-[2-(2,3,4,5,6-pentafluorophenyl)-acryloyl]cinnamic acid and the like, and cinnamic acid derivatives have been recently reported as Rho kinase inhibitors (WO 00/57914, JP-A-2000-44513).

Particularly, various physiological functions of signal transduction via Rho-Rho kinase have been elucidated using (+)-trans-4-(1-aminoethyl)-1-(4-pyridylcarbamoyl)cyclohexane, which is one of the above-mentioned selective Rho kinase inhibitors.

For example, it has been clarified that a selective Rho kinase inhibitor suppresses formation of desmosome and a stress fiber, which is due to the stimulation of Rho or LPA (lysophoshatidic acid), and shows an inhibitory activity on the contraction caused by calcium sensitivity accentuation in smooth muscle (Uehata, M. et al., Nature, 389, 990–994, 1996).

In addition, this inhibitor has been reported to be involved in various cell functions such as an inhibitory action on neurite degeneracy by LPA in nerve cell-derived cultured cell, NIE-115 cell (Hirose, M. et al., J. Cell Biol. 141, 1625–1636, 1998), an inhibitory action on the activation of 1 type $Na^+$—$H^+$ exchanger (Tominaga, T. et al., EMBO J. 17, 4712–4722, 1998).

Furthermore, a concentration-dependent inhibition of AH cell invasion by a specific ROCK/Rho kinase inhibitor in an invasion model of rat ascites hepatoma (AH cell) into homogeneous rat single layer mesothelial cell layer has been reported (Itoh, K. et al., Nature Med. 5, 221–225, 1999), that kinematic accentuation of cells via Rho-Rho kinase has been found to be critical to cancer cell invasion and metastasis, and further that transformation via Rho-Rho kinase is critical in the malignant alteration of cancer cells (Sahai, E. et al., Curr. Biol. 9, 136–145, 1999).

A signal transduction via Rho-Rho kinase is considered to be involved in a great diversity of cell phenomena, such as smooth muscle contraction, cell movement, cell adhesion, morphological change of cells, cell growth and the like, and therefore, a drug that blocks the function of Rho-Rho kinase has a potential of becoming a therapeutic agent of diseases such as hypertension, pulmonary hypertension, angina pectoris, cerebrovascular contraction, asthma, peripheral circulation disorder, glaucoma, erectile dysfunction and the like, in which smooth muscle contraction is involved, invasion and metastasis of cancer, angiostenosis, arteriosclerosis, retinopathy, immune response, fibrosing disease, ischemia-reperfusion injury and the like, in which cell movement is involved, metastasis of cancer, inflammation, autoimmune disease, AIDS, ischemia-reperfusion injury and the like, in which cell adhesion is involved, brain function disorder, osteoporosis (bone formation and resorption) and the like, in which morphological change of cell is involved, and cancer, arteriosclerosis, ischemia-reperfusion injury and the like, in which cell growth is involved.

Accordingly, a specific Rho kinase inhibitor can be a therapeutic drug of various diseases, and creation of a superior new compound is desired.

It is an object of the present invention to provide a novel compound having a Rho kinase inhibitory activity, which has a potential of becoming a therapeutic drug of the diseases in which Rho-Rho kinase is involved.

The present inventors have conducted intensive studies in view of the above-mentioned situation, and found that a novel amide compound represented by the following formula (I), an isomer thereof and a pharmaceutically acceptable salt thereof have a potent Rho kinase inhibitory activity and completed the present invention. They have also found that the compound of the present invention can be useful as a therapeutic agent for various diseases where Rho-Rho kinase is involved, a reagent having a Rho kinase inhibitory activity and a diagnostic agent of diseases caused by Rho kinase, which resulted in the completion of the present invention.

DISCLOSURE OF INVENTION

Accordingly, the present invention provides the following.

(1) An amide compound of the formula

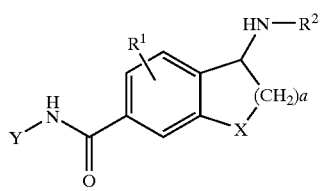

(I)

wherein $R^1$ is hydrogen, alkyl, cycloalkyl, halogen, hydroxyl, alkoxy, haloalkyl, hydroxyalkyl, aralkyl, acyl, alkoxycarbonyl, alkylcarbamoyl, alkylsulfone, nitro, amino optionally having substituents, cyano or phenyl;

$R^2$ is hydrogen, alkyl, cycloalkyl, phenyl or aralkyl, or a group represented by the formula (II)

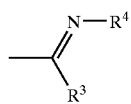

(II)

in the formula (II), $R^3$ is hydrogen, alkyl or amino optionally having substituents, and $R^4$ is hydrogen, alkyl, aralkyl, phenyl, nitro or cyano, or $R^3$ and $R^4$ may be bonded to form a heterocyclic ring containing, in the ring, oxygen atom, sulfur atom or nitrogen atom optionally having a substituent;

a is an integer of 1 to 4;

X is $CH_2$, O, S, $SO_2$ or $NR^7$ wherein $R^7$ is hydrogen, alkyl, aralkyl, haloalkyl or acyl; and Y is a group of the formula (III), (IV), (V) or (VI):

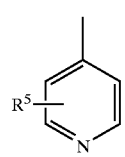

(III)

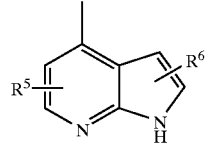

(IV)

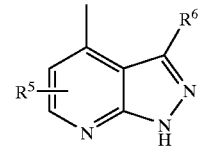

(V)

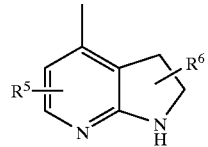

(VI)

in the formulas (III), (IV), (V) and (VI), $R^5$ and $R^6$ are the same or different and each is hydrogen, alkyl, cycloalkyl, phenyl, halogen, hydroxyl, alkoxy, alkoxyalkyl, nitro, amino optionally having substituents or cyano, an isomer thereof or a pharmaceutically acceptable salt thereof.

(2) The amide compound of the above-mentioned (1), wherein, in the formula (I), $R^1$ is hydrogen, alkyl, halogen, hydroxyl, alkoxy, nitro, amino optionally having substituents or cyano; $R^2$ is hydrogen; a is an integer of 1 to 3; X is $CH_2$, S, O or $SO_2$; and Y is a group of the formula (III), (IV) or (V), wherein $R^5$ and $R^6$ in the formulas (III), (IV) and (V) are the same or different and each is hydrogen, alkyl, halogen, hydroxyl, alkoxy, nitro, amino optionally having substituents or cyano, an isomer thereof or a pharmaceutically acceptable salt thereof.

(3) The amide compound of the above-mentioned (2), which is selected from the group consisting of (S)-4-amino-N-(4-pyridyl)thiochromane-7-carboxamide, (S)-4-amino-N-(4-pyridyl)thiochromane-7-carboxamide 1,1-dioxide, (S)-4-amino-N-(1H-pyrazolo[3,4-b]pyridin-4-yl) thiochromane-7-carboxamide, (S)-4-amino-N-(1H-pyrazolo[3,4-b]pyridin-4-yl) thiochromane-7-carboxamide 1,1-dioxide, (S)-4-amino-N-(1H-pyrrolo[2,3-b]pyridin-4-yl) thiochromane-7-carboxamide and (S)-4-amino-N-(1H-pyrrolo[2,3-b]pyridin-4-yl) thiochromane-7-carboxamide 1,1-dioxide, an isomer thereof or a pharmaceutically acceptable salt thereof.

(4) The amide compound of the above-mentioned (2), which is selected from the group consisting of (S)-4-amino-6-methyl-N-(4-pyridyl)thiochromane-7-carboxamide, (S)-4-amino-6-methyl-N-(4-pyridyl)thiochromane-7-carboxamide 1,1-dioxide, (S)-4-amino-6-chloro-N-(4-pyridyl)thiochromane-7-carboxamide, (S)-4-amino-6-chloro-N-(4-pyridyl)thiochromane-7-carboxamide 1,1-dioxide, (S)-4-amino-8-methyl-N-(4-pyridyl)thiochromane-7-carboxamide, (S)-4-amino-8-methyl-N-(4-pyridyl)thiochromane-7-carboxamide 1,1-dioxide, (S)-4-amino-6-methyl-N-(1H-pyrrolo[2,3-b]pyridin-4-yl)thiochromane-7-carboxamide 1,1-dioxide and
(S)-4-amino-6-chloro-N-(1H-pyrrolo[2,3-b]pyridin-4-yl)thiochromane-7-carboxamide 1,1-dioxide, an isomer thereof or a pharmaceutically acceptable salt thereof.
(5) A pharmaceutical agent comprising the amide compound of any of the above-mentioned (1) to (4), an isomer thereof or a pharmaceutically acceptable salt thereof.
(6) A pharmaceutical composition comprising the amide compound of any of the above-mentioned (1) to (4), an isomer thereof or a pharmaceutically acceptable salt thereof, and a pharmaceutically acceptable carrier.
(7) The pharmaceutical agent of the above-mentioned (5), wherein the pharmaceutical agent is at least one member selected from the group consisting of an anticancer drug, a suppressive agent of metastasis of cancer, a suppressive agent of angiogenesis, an antihypertensive, an anti-pulmonary hypertension drug, an anti-angina pectoris drug, a cerebrovascular contraction suppressive agent, an anti-asthma drug, a peripheral circulation-improving drug, an early delivery-preventive drug, an anti-arteriosclerosis drug, a suppressive agent of angiostenosis, an anti-inflammatory agent, an analgesic, an immunosuppressant, a suppressive agent of autoimmune disorder, an anti-AIDS drug, an inhibitor of fertilization and implantation of fertilized egg, a bone formation-promoting drug, a bone resorption inhibitor, a therapeutic agent of retinopathy, a therapeutic agent of glaucoma, a nerve axon-regenerating drug, a brain function-improving drug, a preventive of cell infection of digestive tract, a suppressive agent of fibrosis of various organs, a therapeutic agent of erectile dysfunction and an agent for the prophylaxis or therapy of ischemia-reperfusion injury.
(8) A Rho kinase inhibitor comprising the amide compound of any of the above-mentioned (1) to (4), an isomer thereof or a pharmaceutically acceptable salt thereof.
(9) A therapeutic drug for a disease, in which Rho kinase is involved, which comprises the amide compound of any of the above-mentioned (1) to (4), an isomer thereof or a pharmaceutically acceptable salt thereof.
(10) A reagent comprising the amide compound of any of the above-mentioned (1) to (4), an isomer thereof or a pharmaceutically acceptable salt thereof.
(11) A diagnostic agent comprising the amide compound of any of the above-mentioned (1) to (4), an isomer thereof or a pharmaceutically acceptable salt thereof.

BRIEF DESCRIPTION OF THE DRAWING

FIG. 1 shows a DNA sequence of a part of an expression vector for human ROCK-1 kinase domain part (1 to 477 amino acids) wherein a His-Tag sequence has been added to the C-terminal and the amino acid sequence of the C-terminal of said human ROCK-1 kinase domain part.

DETAILED DESCRIPTION OF THE INVENTION

In the present specification, each substituent of the above-mentioned formula (I) is defined as follows.

Alkyl for $R^1$, $R^2$, $R^3$, $R^4$, $R^5$ and $R^6$ is linear or branched alkyl having 1 to 10 carbon atoms, which is exemplified by methyl, ethyl, propyl, isopropyl, butyl, isobutyl, secondary butyl, tertiary butyl, pentyl, hexyl, heptyl, octyl, nonyl, decyl and the like, with preference given to alkyl having 1 to 4 carbon atoms.

Cycloalkyl for $R^1$, $R^2$, $R^5$ and $R^6$ is that having 3 to 6 carbon atoms and is exemplified by cyclopropyl, cyclobutyl, cyclopentyl, cyclohexyl and the like.

Halogen for $R^1$, $R^5$ and $R^6$ is fluorine, chlorine, bromine or iodine.

Alkoxy for $R^1$, $R^5$, and $R^6$ is linear or branched alkoxy having 1 to 4 carbon atoms, which is exemplified by methoxy, ethoxy, propoxy, isopropoxy, butoxy, tertiary butoxy and the like.

Amino optionally having substituents for $R^1$, $R^3$, $R^5$ and $R^6$ is optionally substituted by substituent(s) selected from the group consisting of alkyl having 1 to 4 carbon atoms, acyl having 1 to 4 carbon atoms and benzoyl. Examples thereof include amino, methylamino, dimethylamino, ethylamino, diethylamino, formylamino, acetylamino, propionylamino, benzoylamino and the like.

Aralkyl for $R^1$, $R^2$ and $R^4$ is that wherein alkyl moiety is alkyl having 1 to 4 carbon atoms and is exemplified by benzyl, 1-phenylethyl, 2-phenylethyl and the like.

Hydroxyalkyl for $R^1$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like.

Haloalkyl for $R^1$ is alkyl for $R^1$, which is substituted by 1 to 5 halogen and exemplified by fluoromethyl, difluoromethyl, trifluoromethyl, 2,2,2-trifluoroethyl, 2,2,3,3,3-pentafluoropropyl and the like.

Acyl for $R^1$ is alkanoyl having 2 to 6 carbon atoms (acetyl, propionyl, butyryl, valeryl, pivaloyl etc.), benzoyl, or phenylalkanoyl wherein the alkanoyl moiety has 2 to 4 carbon atoms (phenylacetyl, phenylpropionyl, phenylbutyryl etc.).

Alkoxycarbonyl for $R^1$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, secondary butoxycarbonyl, tertiary butoxycarbonyl, pentyloxycarbonyl, hexyloxycarbonyl and the like.

Alkylcarbamoyl for $R^1$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkylsulfone for $R^1$ is that wherein the alkyl moiety is linear or branched alkyl having 1 to 6 carbon atoms, which is exemplified by methylsulfone, ethylsulfone, propylsulfone, isopropylsulfone, butylsulfone, isobutylsulfone, secondary butylsulfone, tertiary butylsulfone, pentylsulfone, hexylsulfone and the like.

Alkoxyalkyl for $R^5$ and $R^6$ is that wherein the alkoxy moiety is linear or branched alkoxy having 1 to 4 carbon atoms as exemplified for $R^1$, and the alkyl moiety is alkyl having 1 to 4 carbon atoms. Examples thereof include methoxymethyl, 2-methoxyethyl, 1-methoxyethyl, 3-methoxypropyl, 4-methoxybutyl, ethokymethyl, propoxymethyl, butoxymethyl and the like.

The group formed by $R^3$ and $R^4$ in combination, which forms a heterocyclic ring optionally having, in the ring, oxygen atom, sulfur atom or nitrogen atom optionally having a substituent, is, for example, imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl, or benzoimidazol-2-yl, benzothiazol-2-yl or benzooxazol-2-yl, which optionally has substituents such as halogen, alkyl, alkoxy, haloalkyl, nitro, amino, phenyl, aralkyl and the like. As used herein, halogen, alkyl, alkoxy, haloalkyl and aralkyl are as defined for $R^1$. The substituent of the above-mentioned nitrogen atom optionally having a substituent is exemplified by alkyl, aralkyl, haloalkyl and the like. As used herein, alkyl, aralkyl and haloalkyl are those defined for $R^1$.

Alkyl, aralkyl, haloalkyl and acyl for $R^7$ when X is $NR^7$ are those defined for $R^1$.

The preferable compound of the formula (I) of the present invention is exemplified by the following compounds.

(RS)-4-amino-N-(4-pyridyl)thiochromane-7-carboxamide 1,1-dioxide (RS)-4-amino-N-(4-pyridyl)thiochromane-7-carboxamide (RS)-4-amino-N-(4-pyridyl)chromane-7-carboxamide (RS)-5-amino-N-(4-pyridyl)-5,6,7,8-tetrahydronaphthalene-2-carboxamide (RS)-5-amino-3-methyl-N-(4-pyridyl)-5,6,7,8-tetrahydronaphthalene-2-carboxamide (RS)-3-amino-N-(4-pyridyl)-2,3-dihydrobenzo[b]thiophene-6-carboxamide 1,1-dioxide (RS)-3-amino-5-methyl-N-(4-pyridyl)-2,3-dihydrobenzo[b]-thiophene-6-carboxamide 1,1-dioxide (RS)-3-amino-N-(4-pyridyl)-2,3-dihydrobenzo[b]thiophene-6-carboxamide (RS)-3-amino-5-methyl-N-(4-pyridyl)-2,3-dihydrobenzo[b]-thiophene-6-carboxamide (RS)-3-amino-N-(4-pyridyl)-2,3-dihydrobenzo[b]furan-6-carboxamide (RS)-1-amino-N-(4-pyridyl)indane-5-carboxamide (RS)-5-amino-N-(4-pyridyl)-2,3,4,5-tetrahydro-1-benzothiepine-8-carboxamide 1,1-dioxide (RS)-5-amino-N-(4-pyridyl)-2,3,4,5-tetrahydro-1-benzothiepine-8-carboxamide (RS)-5-amino-N-(4-pyridyl)-2,3,4,5-tetrahydro-1-benzooxepine-8-carboxamide (RS)-5-amino-N-(4-pyridyl)-6,7,8,9-tetrahydrobenzocycloheptene-2-carboxamide (RS)-4-amino-N-(1H-pyrrolo[2,3-b]pyridin-4-yl)thiochromane-7-carboxamide 1,1-dioxide (RS)-4-amino-N-(1H-pyrrolo[2,3-b]pyridin-4-yl)thiochromane-7-carboxamide (RS)-4-amino-N-(1H-pyrrolo[2,3-b]pyridin-4-yl)chromane-7-carboxamide (RS)-5-amino-N-(1H-pyrrolo[2,3-b]pyridin-4-yl)-5,6,7,8-tetrahydronaphthalene-2-carboxamide (RS)-5-amino-3-methyl-N-(1H-pyrrolo[2,3-b]pyridin-4-yl)-5,6,7,8-tetrahydronaphthalene-2-carboxamide (RS)-3-amino-N-(1H-pyrrolo[2,3-b]pyridin-4-yl)-2,3-dihydrobenzo[b]thiophene-6-carboxamide 1,1-dioxide (RS)-3-amino-5-methyl-N-(1H-pyrrolo[2,3-b]pyridin-4-yl)-2,3-dihydrobenzo[b]thiophene-6-carboxamide 1,1-dioxide (RS)-3-amino-N-(1H-pyrrolo[2,3-b]pyridin-4-yl)-2,3-dihydrobenzo[b]thiophene-6-carboxamide (RS)-3-amino-5-methyl-N-(1H-pyrrolo[2,3-b]pyridin-4-yl)-2,3-dihydrobenzo[b]thiophene-6-carboxamide (RS)-3-amino-N-(1H-pyrrolo[2,3-b]pyridin-4-yl)-2,3-dihydrobenzo[b]furan-6-carboxamide (RS)-1-amino-N-(1H-pyrrolo[2,3-b]pyridin-4-yl)indane-5-carboxamide (RS)-5-amino-N-(1H-pyrrolo[2,3-b]pyridin-4-yl)-2,3,4,5-tetrahydro-1-benzothiepine-8-carboxamide 1,1-dioxide (RS)-5-amino-N-(1H-pyrrolo[2,3-b]pyridin-4-yl)-2,3,4,5-tetrahydro-1-benzothiepine-8-carboxamide (RS)-5-amino-N-(1H-pyrrolo[2,3-b]pyridin-4-yl)-2,3,4,5-tetrahydro-1-benzooxepine-8-carboxamide (RS)-5-amino-N-(1H-pyrrolo[2,3-b]pyridin-4-yl)-6,7,8,9-tetrahydrobenzocycloheptene-2-carboxamide (RS)-4-amino-N-(1H-pyrazolo[3,4-b]pyridin-4-yl)thiochromane-7-carboxamide 1,1-dioxide (RS)-4-amino-N-(1H-pyrazolo[3,4-b]pyridin-4-yl)thiochromane-7-carboxamide (RS)-4-amino-N-(1H-pyrazolo[3,4-b]pyridin-4-yl)chromane-7-carboxamide (RS)-5-amino-N-(1H-pyrazolo[3,4-b]pyridin-4-yl)-5,6,7,8-tetrahydronaphthalene-2-carboxamide (RS)-5-amino-3-methyl-N-(1H-pyrazolo[3,4-b]pyridin-4-yl)-5,6,7,8-tetrahydronaphthalene-2-carboxamide (RS)-3-amino-N-(1H-pyrazolo[3,4-b]pyridin-4-yl)-2,3-dihydrobenzo[b]thiophene-6-carboxamide 1,1-dioxide (RS)-3-amino-5-methyl-N-(1H-pyrazolo[3,4-b]pyridin-4-yl)-2,3-dihydrobenzo[b]thiophene-6-carboxamide 1,1-dioxide (RS)-3-amino-N-(1H-pyrazolo[3,4-b]pyridin-4-yl)-2,3-dihydrobenzo[b]thiophene-6-carboxamide (RS)-3-amino-5-methyl-N-(1H-pyrazolo[3,4-b]pyridin-4-yl)-2,3-dihydrobenzo[b]thiophene-6-carboxamide (RS)-3-amino-N-(1H-pyrazolo[3,4-b]pyridin-4-yl)-2,3-dihydrobenzo[b]furan-6-carboxamide (RS)-1-amino-N-(1H-pyrazolo[3,4-b]pyridin-4-yl)indane-5-carboxamide (RS)-5-amino-N-(1H-pyrazolo[3,4-b]pyridin-4-yl)-2,3,4,5-tetrahydro-1-benzothiepine-8-carboxamide 1,1-dioxide (RS)-5-amino-N-(1H-pyrazolo[3,4-b]pyridin-4-yl)-2,3,4,5-tetrahydro-1-benzothiepine-8-carboxamide (RS)-5-amino-N-(1H-pyrazolo[3,4-b]pyridin-4-yl)-2,3,4,5-tetrahydro-1-benzooxepine-8-carboxamide (RS)-5-amino-N-(1H-pyrazolo[3,4-b]pyridin-4-yl)-6,7,8,9-tetrahydrobenzocycloheptene-2-carboxamide (RS)-4-amino-8-methyl-N-(4-pyridyl)thiochromane-7-carboxamide (RS)-4-amino-8-methyl-N-(4-pyridyl)thiochromane-7-carboxamide 1,1-dioxide (RS)-4-amino-8-methyl-N-(1H-pyrazolo[3,4-b]pyridin-4-yl)thiochromane-7-carboxamide 1,1-dioxide (RS)-4-amino-6-methyl-N-(4-pyridyl)thiochromane-7-carboxamide (RS)-4-amino-6-methyl-N-(4-pyridyl)thiochromane-7-carboxamide 1,1-dioxide (RS)-4-amino-6-methyl-N-(1H-pyrazolo[3,4-b]pyridin-4-yl)thiochromane-7-carboxamide (RS)-4-amino-6-methyl-N-(1H-pyrazolo[3,4-b]pyridin-4-yl) thiochromane-7-carboxamide 1,1-dioxide (RS)-4-amino-6-methyl-N-(1H-pyrrolo[2,3-b]pyridin-4-yl)thiochromane-7-carboxamide 1,1-dioxide (RS)-4-amino-6-chloro-N-(4-pyridyl)thiochromane-7-carboxamide (RS)-4-amino-6-chloro-N-(4-pyridyl)thiochromane-7-carboxamide 1,1-dioxide (RS)-4-amino-6-chloro-N-(1H-pyrazolo[3,4-b]pyridin-4-yl)thiochromane-7-carboxamide (RS)-4-amino-6-chloro-N-(1H-pyrazolo[3,4-b]pyridin-4-yl)thiochromane-7-carboxamide 1,1-dioxide (RS)-4-amino-6-chloro-N-(1H-pyrrolo[2,3-b]pyridin-4-yl)thiochromane-7-carboxamide 1,1-dioxide (RS)-4-amino-6-methoxy-N-(4-pyridyl)thiochromane-7-carboxamide (RS)-4-amino-6-methoxy-N-(4-pyridyl)thiochromane-7-carboxamide 1,1-dioxide (R)-4-amino-N-(4-pyridyl)thiochromane-7-carboxamide 1,1-dioxide (R)-4-amino-N-(4-pyridyl)thiochromane-7-carboxamide (R)-4-amino-N-(4-pyridyl)chromane-7-carboxamide (R)-5-amino-N-(4-pyridyl)-5,6,7,8-tetrahydronaphthalene-2-carboxamide (R)-5-amino-3-methyl-N-(4-pyridyl)-5,6,7,8-tetrahydronaphthalene-2-carboxamide (R)-3-amino-N-(4-pyridyl)-2,3-dihydrobenzo[b]thiophene-6-carboxamide 1,1-dioxide (R)-3-amino-5-methyl-N-(4-pyridyl)-2,3-dihydrobenzo[b]thiophene-6-carboxamide 1,1-dioxide (R)-3-amino-N-(4-pyridyl)-2,3-dihydrobenzo[b]thiophene-6-carboxamide (R)-3-amino-5-methyl-N-(4-pyridyl)-2,3-dihydrobenzo[b]-thiophene-6-carboxamide (R)-3-amino-N-(4-pyridyl)-2,3-dihydrobenzo[b]furan-6-carboxamide (R)-1-amino-N-(4-pyridyl)indane-5-carboxamide (R)-5-amino-N-(4-pyridyl)-2,3,4,5-tetrahydro-1-benzothiepine-8-carboxamide 1,1-dioxide (R)-5-amino-N-(4-pyridyl)-2,3,4,5-tetrahydro-1-benzothiepine-8-carboxamide (R)-5-amino-N-(4-pyridyl)-2,3,4,5-tetrahydro-1-benzooxepine-8-carboxamide (R)-5-amino-N-(4-pyridyl)-6,7,8,9-tetrahydrobenzocycloheptene-2-carboxamide (R)-4-amino-N-(1H-pyrrolo[2,3-b]pyridin-4-yl)thiochromane-7-carboxamide 1,1-dioxide (R)-4-amino-N-(1H-pyrrolo[2,3-b]pyridin-4-yl)thiochromane-7-carboxamide (R)-4-amino-N-(1H-pyrrolo[2,3-b]pyridin-4-yl)chromane-7-carboxamide (R)-5-amino-N-(1H-pyrrolo[2,3-b]pyridin-4-yl)-5,6,7,8-tetrahydronaphthalene-2-carboxamide (R)-5-amino-3-methyl-N-(1H-pyrrolo[2,3-b]pyridin-4-yl)-5,6,7,8-tetrahydronaphthalene-2-carboxamide (R)-3-amino-N-(1H-pyrrolo[2,3-b]pyridin-4-yl)-2,3-dihydrobenzo[b]thiophene-6-carboxamide 1,1-dioxide (R)-3-amino-5-methyl-N-(1H-pyrrolo[2,3-b]pyridin-4-yl)-2,3-dihydrobenzo[b]thiophene-6-carboxamide 1,1-dioxide (R)-3-amino-N-(1H-pyrrolo[2,3-b]pyridin-4-yl)-2,3-dihydrobenzo[b]thiophene-6-carboxamide (R)-3-amino-5-methyl-N-(1H-pyrrolo[2,3-b]pyridin-4-yl)-2,3-dihydrobenzo[b]thiophene-6-carboxamide (R)-3-amino-N-(1H-pyrrolo[2,3-b]pyridin-4-yl)-2,3-dihydrobenzo[b]furan-6-carboxamide (R)-1-amino-N-(1H-pyrrolo[2,3-b]pyridin-4-yl)indane-5-carboxamide (R)-5-amino-N-(1H-pyrrolo[2,3-b]pyridin-4-yl)-2,3,4,5-tetrahydro-1-benzothiepine-8-carboxamide 1,1-dioxide (R)-5-amino-N-(1H-pyrrolo[2,3-b]pyridin-4-yl)-2,3,4,5-tetrahydro-1-benzothiepine-8-carboxamide (R)-5-amino-N-(1H-pyrrolo[2,3-b]pyridin-4-yl)-2,3,4,5-tetrahydro-1-benzooxepine-8-carboxamide (R)-5-amino-N-(1H-pyrrolo[2,3-b]pyridin-4-yl)-6,7,8,9-tetrahydrobenzocycloheptene-2-carboxamide (R)-4-amino-N-(1H-pyrazolo[3,4-b]pyridin-4-yl)thiochromane-7-carboxamide 1,1-dioxide (R)-4-amino-N-(1H-pyrazolo[3,4-b]pyridin-4-yl)thiochromane-7-carboxamide (R)-4-amino-N-(1H-pyrazolo[3,4-b]pyridin-4-yl)chromane-7-carboxamide (R)-5-amino-N-(1H-pyrazolo[3,4-b]pyridin-4-yl)-5,6,7,8-tetrahydronaphthalene-2-carboxamide (R)-5-amino-3-methyl-N-(1H-pyrazolo[3,4-b]pyridin-4-yl)-5,6,7,8-tetrahydronaphthalene-2-carboxamide (R)-3-amino-N-(1H-pyrazolo[3,4-b]pyridin-4-yl)-2,3-dihydrobenzo[b]thiophene-6-carboxamide 1,1-dioxide (R)-3-amino-5-methyl-N-(1H-pyrazolo[3,4-b]pyridin-4-yl)-2,3-dihydrobenzo[b]thiophene-6-carboxamide 1,1-dioxide (R)-3-amino-N-(1H-pyrazolo[3,4-b]pyridin-4-yl)-2,3-dihydrobenzo[b]thiophene-6-carboxamide (R)-3-amino-5-methyl-N-(1H-pyrazolo[3,4-b]pyridin-4-yl)-2,3-dihydrobenzo[b]thiophene-6-carboxamide (R)-3-amino-N-(1H-pyrazolo[3,4-b]pyridin-4-yl)-2,3-dihydrobenzo[b]furan-6-carboxamide (R)-1-amino-N-(1H-pyrazolo[3,4-b]pyridin-4-yl)indane-5-carboxamide (R)-5-amino-N-(1H-pyrazolo[3,4-b]pyridin-4-yl)-2,3,4,5-tetrahydro-1-benzothiepine-8-carboxamide 1,1-dioxide (R)-5-amino-N-(1H-pyrazolo[3,4-b]pyridin-4-yl)-2,3,4,5-tetrahydro-1-benzothiepine-8-carboxamide (R)-5-amino-N-(1H-pyrazolo[3,4-b]pyridin-4-yl)-2,3,4,5-tetrahydro-1-benzooxepine-8-carboxamide (R)-5-amino-N-(1H-pyrazolo[3,4-b]pyridin-4-yl)-6,7,8,9-tetrahydrobenzocycloheptene-2-carboxamide (R)-4-amino-8-methyl-N-(4-pyridyl)thiochromane-7-carboxamide (R)-4-amino-8-methyl-N-(4-pyridyl)thiochromane-7-carboxamide 1,1-dioxide (R)-4-amino-8-methyl-N-(1H-pyrazolo[3,4-b]pyridin-4-yl)thiochromane-7-carboxamide 1,1-dioxide (R)-4-amino-6-methyl-N-(4-pyridyl)thiochromane-7-carboxamide (R)-4-amino-6-methyl-N-(4-pyridyl)thiochromane-7-carboxamide 1,1-dioxide (R)-4-amino-6-methyl-N-(1H-pyrazolo[3,4-b]pyridin-4-yl)thiochromane-7-carboxamide (R)-4-amino-6-methyl-N-(1H-pyrazolo[3,4-b]pyridin-4-yl)thiochromane-7-carboxamide 1,1-dioxide (R)-4-amino-6-methyl-N-(1H-pyrrolo[2,3-b]pyridin-4-yl)thiochromane-7-carboxamide 1,1-dioxide (R)-4-amino-6-chloro-N-(4-pyridyl)thiochromane-7-carboxamide (R)-4-amino-6-chloro-N-(4-pyridyl)thiochromane-7-carboxamide 1,1-dioxide (R)-4-amino-6-chloro-N-(1H-pyrazolo[3,4-b]pyridin-4-yl)thiochromane-7-carboxamide (R)-4-amino-6-chloro-N-(1H-pyrazolo[3,4-b]pyridin-4-yl)thiochromane-7-carboxamide 1,1-dioxide (R)-4-amino-6-chloro-N-(1H-pyrrolo[2,3-b]pyridin-4-yl)thiochromane-7-carboxamide 1,1-dioxide (R)-4-amino-6-methoxy-N-(4-pyridyl)thiochromane-7-carboxamide (R)-4-amino-6-methoxy-N-(4-pyridyl)thiochromane-7-carboxamide 1,1-dioxide (S)-4-amino-N-(4-pyridyl)thiochromane-7-carboxamide 1,1-dioxide (S)-4-amino-N-(4-pyridyl)thiochromane-7-carboxamide (S)-4-amino-N-(4-pyridyl)chromane-7-carboxamide (S)-5-amino-N-(4-pyridyl)-5,6,7,8-tetrahydronaphthalene-2-carboxamide (S)-5-amino-3-methyl-N-(4-pyridyl)-5,6,7,8-tetrahydronaphthalene-2-carboxamide (S)-3-amino-N-(4-pyridyl)-2,3-dihydrobenzo[b]thiophene-6-carboxamide 1,1-dioxide (S)-3-amino-5-methyl-N-(4-pyridyl)-2,3-dihydrobenzo[b]-thiophene-6-carboxamide 1,1-dioxide (S)-3-amino-N-(4-pyridyl)-2,3-dihydrobenzo[b]thiophene-6-carboxamide (S)-3-amino-5-methyl-N-(4-pyridyl)-2,3-dihydrobenzo[b]-thiophene-6-carboxamide (S)-3-amino-N-(4-pyridyl)-2,3-dihydrobenzo[b]furan-6-carboxamide (S)-1-amino-N-(4-pyridyl)indane-5-carboxamide (S)-5-amino-N-(4-pyridyl)-2,3,4,5-tetrahydro-1-benzothiepine-8-carboxamide 1,1-dioxide (S)-5-amino-N-(4-pyridyl)-2,3,4,5-tetrahydro-1-benzothiepine-8-carboxamide (S)-5-amino-N-(4-pyridyl)-2,3,4,5-tetrahydro-1-benzooxepine-8-carboxamide (S)-5-amino-N-(4-pyridyl)-6,7,8,9-tetrahydrobenzocycloheptene-2-carboxamide (S)-4-amino-N-(1H-pyrrolo[2,3-b]pyridin-4-yl)thiochromane-7-carboxamide 1,1-dioxide (S)-4-amino-N-(1H-pyrrolo[2,3-b]pyridin-4-yl)thiochromane-7-carboxamide (S)-4-amino-N-(1H-pyrrolo[2,3-b]pyridin-4-yl)chromane-7-carboxamide (S)-5-amino-N-(1H-pyrrolo[2,3-b]pyridin-4-yl)-5,6,7,8-tetrahydronaphthalene-2-carboxamide (S)-5-amino-3-methyl-N-(1H-pyrrolo[2,3-b]pyridin-4-yl)-5,6,7,8-tetrahydronaphthalene-2-carboxamide (S)-3-amino-N-(1H-pyrrolo[2,3-b]pyridin-4-yl)-2,3-dihydrobenzo[b]thiophene-6-carboxamide 1,1-dioxide (S)-3-amino-5-methyl-N-(1H-pyrrolo[2,3-b]pyridin-4-yl)-2,3-dihydrobenzo[b]thiophene-6-carboxamide 1,1-dioxide (S)-3-amino-N-(1H-pyrrolo[2,3-b]pyridin-4-yl)-2,3-dihydrobenzo[b]thiophene-6-carboxamide (S)-3-amino-5-methyl-N-(1H-pyrrolo[2,3-b]pyridin-4-yl)-2,3-dihydrobenzo[b]thiophene-6-carboxamide (S)-3-amino-N-(1H-pyrrolo[2,3-b]pyridin-4-yl)-2,3-dihydrobenzo[b]furan-6-carboxamide (S)-1-amino-N-(1H-pyrrolo[2,3-b]pyridin-4-yl)indane-5-carboxamide (S)-5-amino-N-(1H-pyrrolo[2,3-b]pyridin-4-yl)-2,3,4,5-tetrahydro-1-benzothiepine-8-carboxamide 1,1-dioxide (S)-5-amino-N-(1H-pyrrolo[2,3-b]pyridin-4-yl)-2,3,4,5-tetrahydro-1-benzothiepine-8-carboxamide (S)-5-amino-N-(1H-pyrrolo[2,3-b]pyridin-4-yl)-2,3,4,5-tetrahydro-1-benzooxepine-8-carboxamide (S)-5-amino-N-(1H-pyrrolo[2,3-b]pyridin-4-yl)-6,7,8,9-tetrahydrobenzocycloheptene-2-carboxamide (S)-4-amino-N-(1H-pyrazolo[3,4-b]pyridin-4-yl)thiochromane-7-carboxamide 1,1-dioxide (S)-4-amino-N-(1H-pyrazolo[3,4-b]pyridin-4-yl)thiochromane-7-carboxamide (S)-4-amino-N-(1H-pyrazolo[3,4-b]pyridin-4-yl)chromane-7-carboxamide (S)-5-amino-N-(1H-pyrazolo[3,4-b]pyridin-4-yl)-5,6,7,8-tetrahydronaphthalene-2-carboxamide (S)-5-amino-3-methyl-N-(1H-pyrazolo[3,4-b]pyridin-4-yl)-5,6,7,8-tetrahydronaphthalene-2-carboxamide (S)-3-amino-N-(1H-pyrazolo[3,4-b]pyridin-4-yl)-2,3-dihydrobenzo[b]thiophene-6-carboxamide 1,1-dioxide (S)-3-amino-5-methyl-N-(1H-pyrazolo[3,4-b]pyridin-4-yl)-2,3-dihydrobenzo[b]thiophene-6-carboxamide 1,1-dioxide (S)-3-amino-N-(1H-pyrazolo[3,4-b]pyridin-4-yl)-2,3-dihydrobenzo[b]thiophene-6-carboxamide (S)-3-amino-5-methyl-N-(1H-pyrazolo[3,4-b]pyridin-4-yl)-2,3-dihydrobenzo[b]thiophene-6-carboxamide (S)-3-amino-N-(1H-pyrazolo[3,4-b]pyridin-4-yl)-2,3-dihydrobenzo[b]furan-6-carboxamide (S)-1-amino-N-(1H-pyrazolo[3,4-b]pyridin-4-yl)indane-5-carboxamide (S)-5-amino-N-(1H-pyrazolo[3,4-b]pyridin-4-yl)-2,3,4,5-tetrahydro-1-benzothiepine-8-carboxamide 1,1-dioxide (S)-5-amino-N-(1H-pyrazolo[3,4-b]pyridin-4-yl)-2,3,4,5-tetrahydro-1-benzothiepine-8-carboxamide (S)-5-amino-N-(1H-pyrazolo[3,4-b]pyridin-4-yl)-2,3,4,5-tetrahydro-1-benzooxepine-8-carboxamide (S)-5-amino-N-(1H-pyrazolo[3,4-b]pyridin-4-yl)-6,7,8,9-tetrahydrobenzocycloheptene-2-carboxamide (S)-4-amino-8-methyl-N-(4-pyridyl)thiochromane-7-carboxamide (S)-4-amino-8-methyl-N-(4-pyridyl)thiochromane-7-carboxamide 1,1-dioxide (S)-4-amino-8-methyl-N-(1H-pyrazolo[3,4-b]pyridin-4-yl)thiochromane-7-carboxamide 1,1-dioxide (S)-4-amino-6-methyl-N-(4-pyridyl)thiochromane-7-carboxamide (S)-4-amino-6-methyl-N-(4-pyridyl)thiochromane-7-carboxamide 1,1-dioxide (S)-4-amino-6-methyl-N-(1H-pyrazolo[3,4-b]pyridin-4-yl)thiochromane-7-carboxamide (S)-4-amino-6-methyl-N-(1H-pyrazolo[3,4-b]pyridin-4-yl)thiochromane-7-carboxamide 1,1-dioxide (S)-4-amino-6-methyl-N-(1H-pyrrolo[2,3-b]pyridin-4-yl)thiochromane-7-carboxamide 1,1-dioxide (S)-4-amino-6-chloro-N-(4-pyridyl)thiochromane-7-carboxamide (S)-4-amino-6-chloro-N-(4-pyridyl)thiochromane-7-carboxamide 1,1-dioxide (S)-4-amino-6-chloro-N-(1H-pyrazolo[3,4-b]pyridin-4-yl)thiochromane-7-carboxamide (S)-4-amino-6-chloro-N-(1H-pyrazolo[3,4-b]pyridin-4-yl)thiochromane-7-carboxamide 1,1-dioxide (S)-4-amino-6-chloro-N-(1H-pyrrolo[2,3-b]pyridin-4-yl)thiochromane-7-carboxamide 1,1-dioxide (S)-4-amino-6-methoxy-N-(4-pyridyl)thiochromane-7-carboxamide (S)-4-amino-6-methoxy-N-(4-pyridyl) thiochromane-7-carboxamide 1,1-dioxide Preferred are compounds having an (S)-configuration, more preferably the following compounds.

(S)-4-amino-N-(4-pyridyl)thiochromane-7-carboxamide (S)-4-amino-N-(4-pyridyl)thiochromane-7-carboxamide 1,1-dioxide (S)-4-amino-6-methyl-N-(4-pyridyl)thiochromane-7-carboxamide (S)-4-amino-6-methyl-N-(4-pyridyl)thiochromane-7-carboxamide 1,1-dioxide (S)-4-amino-6-chloro-N-(4-pyridyl)thiochromane-7-carboxamide (S)-4-amino-6-chloro-N-(4-pyridyl)thiochromane-7-carboxamide 1,1-dioxide (S)-4-amino-8-methyl-N-(4-pyridyl)thiochromane-7-carboxamide (S)-4-amino-8-methyl-N-(4-pyridyl)thiochromane-7-carboxamide 1,1-dioxide (S)-4-amino-N-(1H-pyrazolo[3,4-b]pyridin-4-yl)thiochromane-7-carboxamide (S)-4-amino-N-(1H-pyrazolo[3,4-b]pyridin-4-yl)thiochromane-7-carboxamide 1,1-dioxide (S)-4-amino-N-(1H-pyrrolo[2,3-b]pyridin-4-yl)thiochromane-7-carboxamide (S)-4-amino-N-(1H-pyrrolo[2,3-b]pyridin-4-yl)thiochromane-7-carboxamide 1,1-dioxide (S)-4-amino-6-methyl-N-(1H-pyrrolo[2,3-b]pyridin-4-yl)thiochromane-7-carboxamide 1,1-dioxide (S)-4-amino-6-chloro-N-(1H-pyrrolo[2,3-b]pyridin-4-yl)thiochromane-7-carboxamide 1,1-dioxide A pharmaceutically acceptable salt of the compound of the present invention is exemplified by a salt with an inorganic acid such as hydrochloric acid, hydrobromic acid, sulfuric acid, phosphoric acid, nitric acid and the like, and a salt with an organic acid such as acetic acid, propionic acid, succinic acid, maleic acid, fumaric acid, benzoic acid, citric acid, malic acid, methanesulfonic acid, benzenesulfonic acid and the like. Their hydrates (1 hydrate, 2 hydrate, 3 hydrate, 1/2 hydrate, 3/2 hydrate, 1/4 hydrate, 4/5 hydrate, 1/5 hydrate, 3/4 hydrate, 1/3 hydrate, 5/3 hydrate, 5/4 hydrate etc.), solvates and the like are also encompassed in the compound of the present invention. In addition, N-oxide compounds are also encompassed in the compound of the present invention.

When the compound of the present invention contains a geometrical isomer, the present invention encompasses an isomer, a trans isomer and a mixture thereof. When the compound of the present invention has one or more asymmetric centers in one molecule, various optical isomers are present. The present invention encompasses an optical isomer, a racemate and a diastereomer, and a mixture thereof.

The compound of the formula (I) of the present invention can be synthesized according to the following Methods 1 to 4.

Method 1:

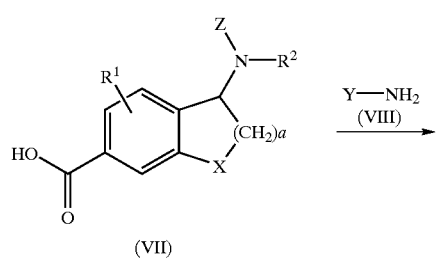

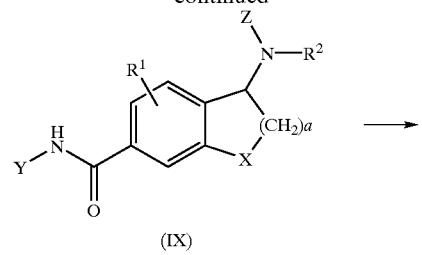

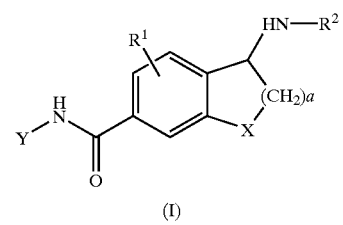

wherein Z is an amine-protecting group generally used in the organic synthesis chemistry, such as benzyloxycarbonyl, tertiary butoxycarbonyl, benzyl and the like, and other symbols are as defined above.

The condensation reaction of the compound of the formula (VII) and the compound of the formula (VIII) can be carried out according to the following three methods.

(1) The compound (VII) is converted to an acid halide by a conventional method using a halogenating agent such as thionyl chloride etc., and condensed with compound (VIII) in a suitable solvent (acetonitrile, dichloromethane, dichloroethane, chloroform etc.) in the presence of a base (triethylamine, diisopropylethylamine, pyridine, sodium methoxide, sodium ethoxide, sodium hydroxide, potassium hydroxide, sodium acetate etc.) at −20° C. to the refluxing temperature of the solvent for 30 min to 12 hr to give compound of the formula (IX). In this reaction, the base to be used may be used as a solvent. The amino group of compound (IX) is deprotected under the conditions generally used in the organic synthesis chemistry (hydrogen-palladium catalyst, 4 mol/L hydrochloric acid-dioxane, trifluoroacetic acid, hydrobromic acid-acetic acid etc.) to synthesize the compound of the formula (I). These reactions generally complete within 24 hours.

(2) The compound (IX) can be produced by condensing compound (VII) with compound (VIII) in, where necessary, a suitable solvent (N,N-dimethylformamide, dimethyl sulfoxide, methanol, ethanol, isopropyl alcohol, butanol etc.) in the presence of a condensing agent (1,3-dicyclohexylcarbodiimide, 1-ethyl-3-(3-dimethylaminopropyl)carbodiimide, carbonyldiimidazole, diethyl cyanophosphate, 2-chloro-1-methylpyridinium iodide etc.), or by condensing compound (VII) with compound (VIII) in a suitable solvent (N,N-dimethylformamide, dimethyl sulfoxide etc.) in the presence of a phosphoric ester such as diethyl cyanophosphate etc. and a base (triethylamine, pyridine etc.). The reaction temperature is generally 0° C. to 100° C., and the reaction time is generally 30 minutes to 24 hours. The reaction using a condensing agent may be carried out in the presence of 1-hydroxybenztriazole and the like as necessary. Then, the amino group of compound (IX) is deprotected under the conditions generally used in the organic synthesis chemistry (hydrogen-palladium catalyst, 4 mol/L hydrochloric acid-dioxane, trifluoroacetic acid, hydrobromic acid-acetic acid etc.) to synthesize the compound of the formula (I). These reactions generally complete within 24 hours.

(3) The compound (VII) is converted to a mixed acid anhydride with carbonate (methyl chlorocarbonate, ethyl chlorocarbonate etc.) and the like, and condensed with compound (VIII) in a suitable solvent (methanol, ethanol, isopropyl alcohol, butanol, ethylene glycol, tetrahydrofuran, toluene, nitrobenzene or a mixed solvent of these etc.) or without solvent in the presence of a base (triethylamine, pyridine, sodium methoxide, sodium ethoxide, sodium hydroxide, potassium hydroxide etc.) at −50° C. to the refluxing temperature of the solvent for 1–24 hr to synthesize compound (IX). Then, the amino group of compound (IX) is deprotected under the conditions generally used in the organic synthesis chemistry (hydrogen-palladium catalyst, 4 mol/L hydrochloric acid-dioxane, trifluoroacetic acid, hydrobromic acid-acetic acid etc.) to synthesize the compound of the formula (I). These reactions generally complete within 24 hours.

When Y of the formula (VIII) is represented by the formula (IV), (V) or (VI)

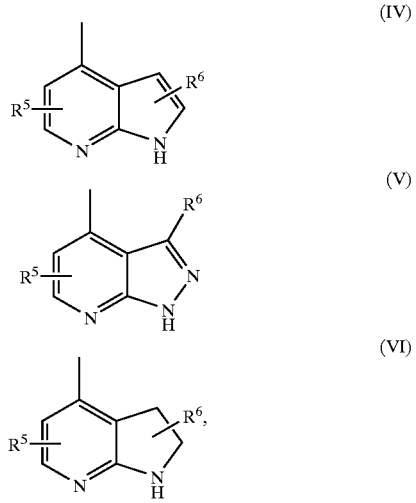

the objective compound of the formula (I) can be synthesized by protecting the secondary amine in the pyrrolopyridine (IV), pyrazolopyridine (V) or dihydropyrrolopyridine (VI) ring with an amine-protecting group (acetyl, trimethylsilylethoxymethyl, tertiary butoxycarbonyl, benzyloxycarbonyl, trityl etc.) generally used for organic synthesis, and carrying out the above-mentioned reaction, and after the reaction, eliminating the protecting group by the above-mentioned conventional method.

The compound of the formula (VII) can be synthesized by the method described in the following Methods 6 to 8, the compound of the formula (IX) wherein Y is represented by the formula (IV) or (V) can be synthesized by the method described in the following Method 5, and the amine compound of the formula (VIII) can be synthesized by the method described in WO 93/0521.

Method 2:

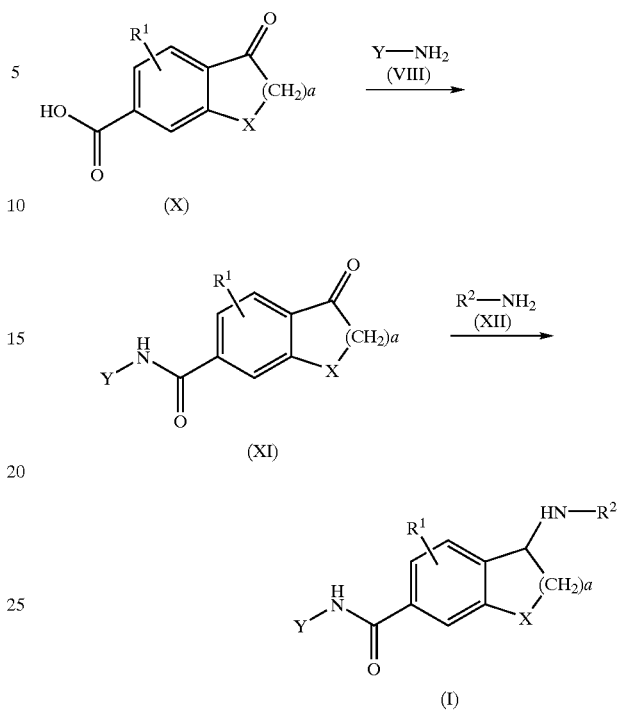

wherein each symbol is as defined above.

The compound of the formula (XI) can be synthesized by reacting the compound of the formula (X) and compound (VIII) by the amide synthetic method described in Method 1. The compound (XI) and compound of the formula (XII) can be led to the compound of the formula (I) by reductive amination. For example, compound (XI) and compound (XII) are reacted in a solvent that does not inhibit the progress of the reaction (methanol, ethanol, methylene chloride, chloroform, acetonitrile, tetrahydrofuran, N,N-dimethylformamide or an optionally mixed solvent thereof etc.) at a temperature of from cooling to the refluxing temperature of the solvent (preferably 0° C. to room temperature) for 10 minutes to 24 hours. The compound of the formula (I) can be obtained by adding a reducing agent generally used for organic synthesis (sodium borohydride, sodium cyanoborohydride etc.) to the reaction mixture under cooling to the refluxing temperature of the solvent (preferably 0° C. to room temperature) and allowing reaction at the same temperature for 10 minutes to 3 days. The compound of the formula (I) can be also synthesized by using, instead of adding a reducing agent, a catalytic hydrogenation reaction (hydrogen-palladium catalyst, hydrogen-Raney-nickel etc.).

Method 3: A compound of the formula (I) wherein $R^2$ is represented by the formula (II)

can be synthesized by the following method.

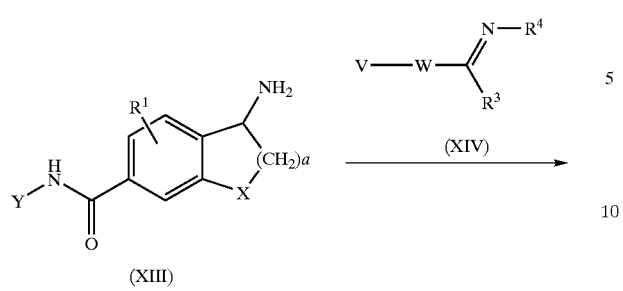

(XIII)

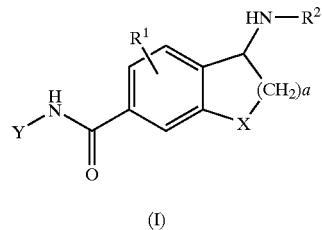

(I)

wherein $R^2$ is represented by the formula (II), when $R^3$ is an amino group, it may be protected by tertiary butoxycarbonyl, benzyloxycarbonyl, acetyl, benzoyl and the like, W is O, S or a heterocyclic ring such as pyrazole and the like, V is hydrogen, lower alkyl (methyl, propyl etc.), benzyl, p-nitrobenzyl and the like, and other symbols are as defined above.

The objective compound of the formula (I) can be synthesized by condensing compound of the formula (XIII) [compound of the formula (I) wherein $R^2$ is hydrogen] with compound of the formula (XIV) or an acid addition salt thereof. For example, the reaction can be carried out in a suitable solvent (water, methanol, ethanol, N,N-dimethylformamide, dioxane, tetrahydrofuran or an optionally mixed solvent thereof etc.) at an optional temperature (preferably 0–100° C.) for 30 minutes to 48 hours. Where necessary, a base (potassium hydroxide, sodium hydroxide, potassium carbonate, sodium carbonate, triethylamine, diisopropylethylamine, 4-dimethylaminopyridine etc.) is preferably used as a deoxidizing agent.

Method 4: A compound of the formula (I) wherein Y is represented by the formula (VI)

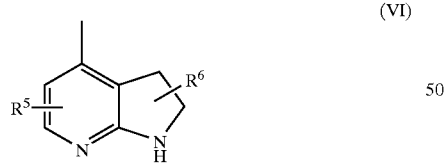

(VI)

can be synthesized by the following method.

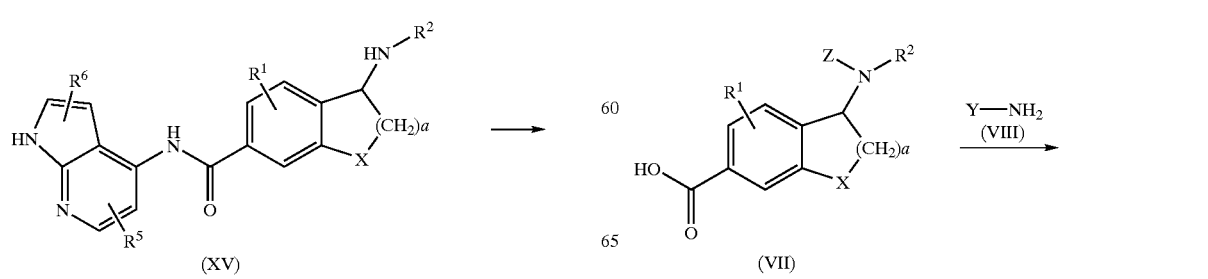

(XV)

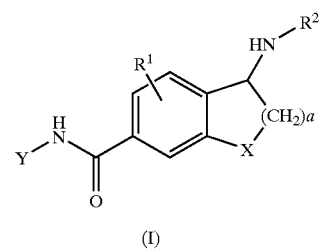

(I)

wherein Y represents the formula (VI) and other symbols are as defined above.

The compound of the formula (XV) [compound of the formula (I) wherein Y has the formula (V)] is subjected to hydrogenation (1–50 pressure) in a suitable solvent (trifluoroacetic acid, methanol, ethanol, isopropyl alcohol etc.) in the presence of a catalyst (palladium-carbon, platinum oxide, Raney-nickel etc.) at a temperature of from room temperature to 100° C. to synthesize the objective compound of the formula (I). The reaction generally ends in 24 hours. In this reaction, an acid (hydrochloric acid, acetic acid etc.) may be added as necessary.

Method 5: The compound of the formula (IX) wherein Y is the formula (IV) or (V)

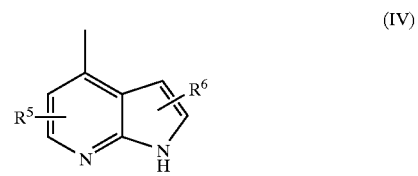

(IV)

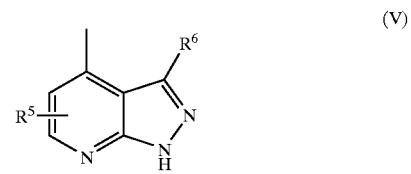

(V)

can be synthesized by the following method.

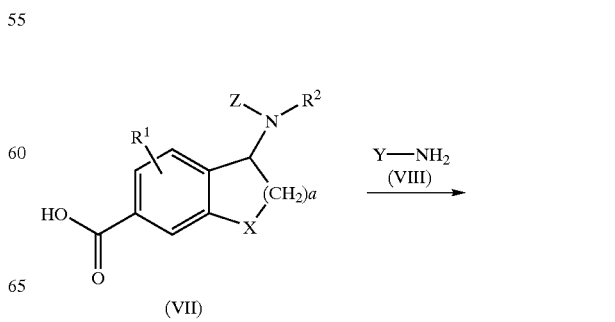

(VII)

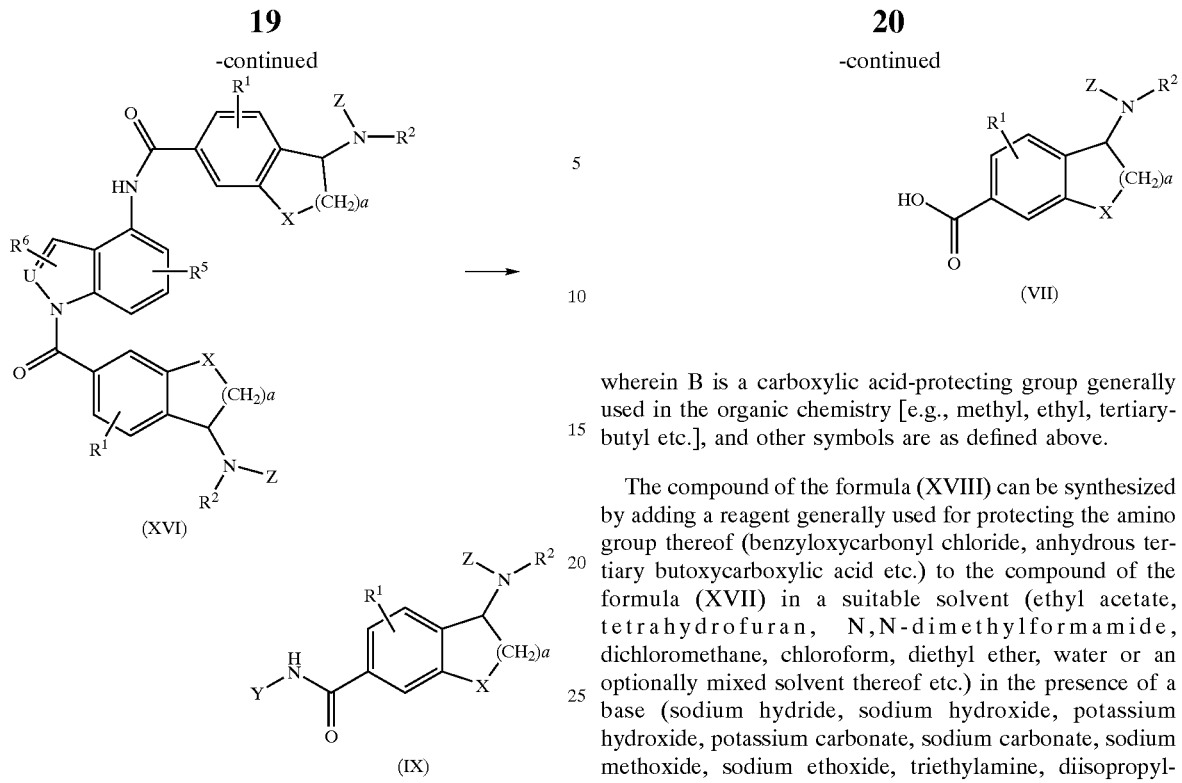

wherein Y represents the formula (IV) or (V), U represents —CH= or —N=, and other symbols are as defined above.

The compound of the formula (XVI) can be synthesized by reacting compound (VII) and two equivalents of compound (VIII) by the amide synthetic method mentioned under Method 1. The objective compound of the formula (IX) can be synthesized by hydrolysis or alcoholysis of compound (XVI) in a solvent (methanol, ethanol, isopropyl alcohol, water or an optionally mixed solvent thereof etc.) from 0° C. to the boiling point of the solvent for 30 min to 24 hr. In this reaction, a base (sodium hydroxide, potassium hydroxide, sodium methoxide, potassium carbonate, sodium carbonate, sodium hydrogencarbonate etc.) may be added as necessary.

Method 6: The compound of the formula (VII) can be synthesized by the following method.

wherein B is a carboxylic acid-protecting group generally used in the organic chemistry [e.g., methyl, ethyl, tertiary-butyl etc.], and other symbols are as defined above.

The compound of the formula (XVIII) can be synthesized by adding a reagent generally used for protecting the amino group thereof (benzyloxycarbonyl chloride, anhydrous tertiary butoxycarboxylic acid etc.) to the compound of the formula (XVII) in a suitable solvent (ethyl acetate, tetrahydrofuran, N,N-dimethylformamide, dichloromethane, chloroform, diethyl ether, water or an optionally mixed solvent thereof etc.) in the presence of a base (sodium hydride, sodium hydroxide, potassium hydroxide, potassium carbonate, sodium carbonate, sodium methoxide, sodium ethoxide, triethylamine, diisopropylethylamine etc.) and reacting the mixture at a temperature of from −20° C. to the boiling point of the solvent (preferably 0° C. to room temperature) for 1 min to 24 hr. Then compound (XVIII) is reacted in a suitable solvent (tetrahydrofuran, diethyl ether, ethyl acetate, methanol, ethanol, isopropyl alcohol, tertiary butyl alcohol, water or an optionally mixed solvent thereof etc.) under the conditions generally used for removing the carboxylic acid-protecting group (sodium hydride-water, potassium carbonate-water, trifluoroacetic acid etc.) at a temperature of from 0° C. to the boiling point of the solvent for 1 min to 24 hr to give compound (VII).

The compound of the formula (XVII) can be synthesized by the methods described in Methods 9–11.

Method 7: The compound of the formula (VII) wherein X is $SO_2$ can be synthesized by the following method.

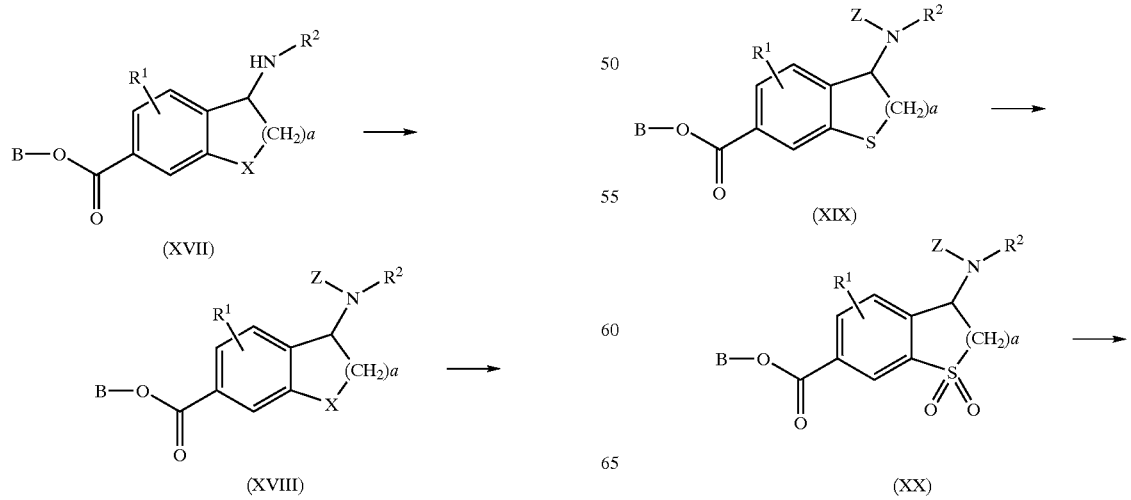

-continued

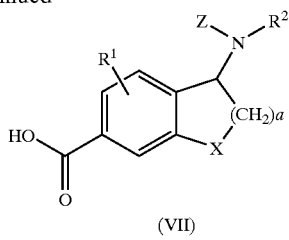

(VII)

wherein X represents SO₂ and other symbols are as defined above.

The compound of the formula (XIX) [compound of the formula (XVIII) wherein X is S] is reacted in a suitable solvent (ethyl acetate, tetrahydrofuran, N,N-dimethylformamide, dichloromethane, chloroform, diethylether, acetone, water or an optionally mixed solvent thereof etc.) using an oxidizing agent (meta-chloroperbenzoic acid, chromium oxide, pyridinium chlorochromate [PCC], 2KHSO₅.KHSO₄.K₂SO₄ etc.) generally used at a temperature of from 0° C. to the boiling point of the solvent for 1 min to 24 hr to synthesize the compound of the formula (XX).

Furthermore, compound (XX) is subjected to deprotection of the carboxyl group according to the method described in Method 6 to give the objective compound (VII).

In addition, a compound of the formula (VII) wherein X is S can be directly reacted under the reaction conditions of the oxidization method of sulfur atom mentioned above, which have been appropriately determined, to lead to the objective compound (VII) (compound wherein X is SO₂).

Method 8: The compound of the formula (VII) can be synthesized by the following method.

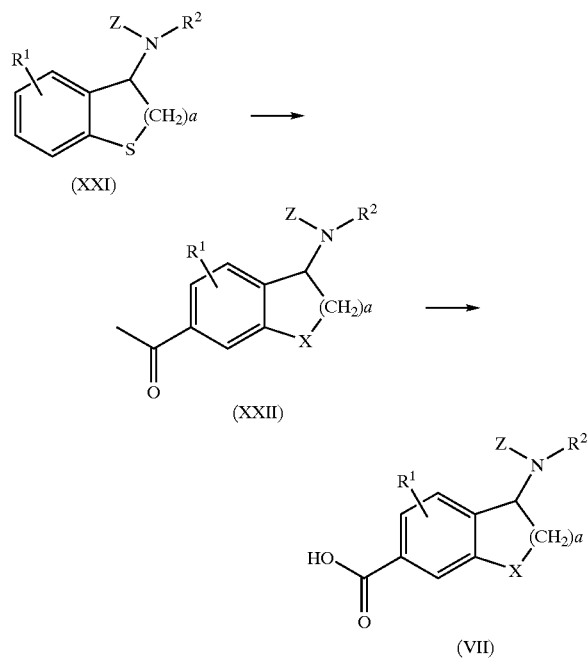

wherein each symbol is as defined above.

The compound of the formula (XXI) can be led to a compound of the formula (XXII) by the Friedel-Crafts reaction. For example, compound (XXII) can be synthesized by reacting compound (XXI) in a suitable solvent (methylene chloride, chloroform, nitrobenzene etc.) using acetic anhydride or acetyl chloride and a Lewis acid (aluminum chloride, tin tetrachloride, titanium tetrachloride etc.) at a temperature of from −20° C. to the boiling point of the solvent for 1 min to 24 hr.

Then, compound (XXII) can be converted to compound (VII) by haloform reaction. For example, compound (XXII) is dissolved in a suitable solvent (methanol, ethanol, isopropyl alcohol, water or an optionally mixed solvent thereof etc.), treated with halogen or an equivalent thereof (chlorine, bromine, iodine, sodium hypochlorite etc.) in the presence of a base (sodium hydroxide, potassium hydroxide etc.) at 0 to 150° C. for 30 min to 24 hr, and neutralized with an acid (hydrochloric acid, sulfuric acid, acetic acid etc.) to synthesize compound (VII).

Method 9: The compound of the formula (XVII) wherein R² is hydrogen can be synthesized by the following method.

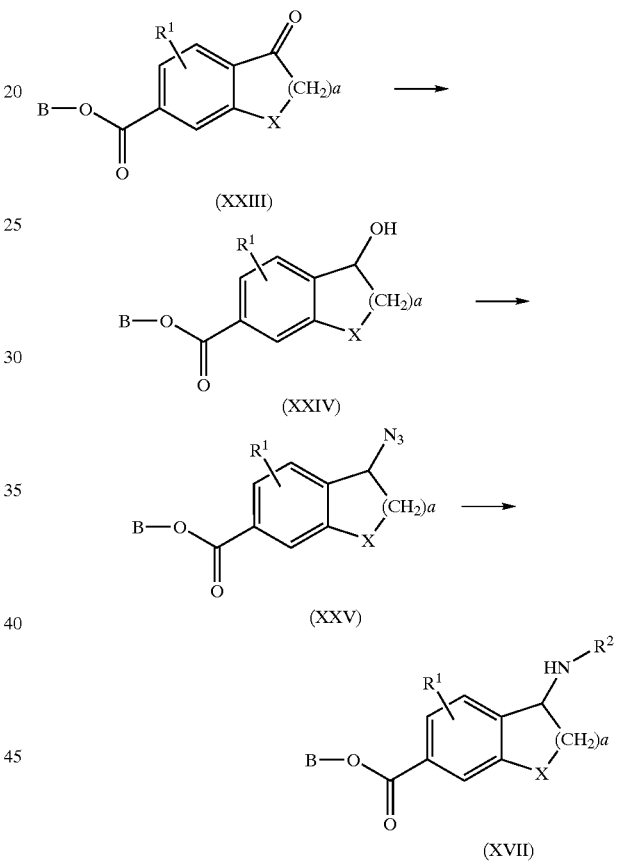

wherein R² is hydrogen and other symbols are as defined above.

The compound of the formula (XXIII) is dissolved in a suitable solvent (tetrahydrofuran, diethylether, enol, methanol or an optionally mixed solvent thereof etc.), a reducing agent (sodium borohydride, lithium aluminum hydride etc.) generally used is added, and the mixture is reacted under cooling to the refluxing temperature of the solvent for 1 min to 24 hr to give a compound of the formula (XXIV). In this case, an optically activated compound (XXIV) can be obtained by applying the generally employed asymmetric reduction of carbonyl [method using borane-(R) or (S)-5,5-diphenyl-2-methyl-3,4-propano-1,3,2-oxazaborolidine, hydrogen-(R) or (S)-bis(diphenylphosphino)-1,1'-binaphthyl etc.].

Then, compound (XXIV) is dissolved in a suitable solvent (tetrahydrofuran, diethylether, toluene, benzene, dichloromethane, chloroform etc.) and reacted using generally used azidation (diphenylphosphorylazide-1,8-diazabicyclo-[5,4,0]-7-undecene, diphenylphosphorylazide-triphenylphosphine-diethylazadicarboxylate, methanesulfonic anhydride-sodium azide etc.) at a temperature of from −78° C. to the refluxing temperature of the solvent for 1 min to 72 hr to give the compound of the formula (XXV).

The obtained compound (XXV) is dissolved in a suitable solvent (tetrahydrofuran, diethylether, toluene, benzene, ethanol, methanol, water or an optionally mixed solvent thereof etc.), and reacted using a reducing agent (triphenylphosphine, tin tetrachloride, hydrogen-palladium catalyst etc.) at a temperature of from under ice-cooling to the refluxing temperature of the solvent for 1 min to 24 hr to give the objective compound (XVII) (compound wherein $R^2$ is hydrogen).

The compound (XXIII) can be obtained according to the methods described in Tetrahedron Lett. pp. 5499–5502 (1992), Ger. Offen. DE 19532312 A16 WO 9709327 A1 and J. Org. Chem. pp. 1216–1218 (1994).

Method 10: The compound of the formula (XVII) wherein $R^2$ is alkyl or aralkyl can be synthesized by the following method.

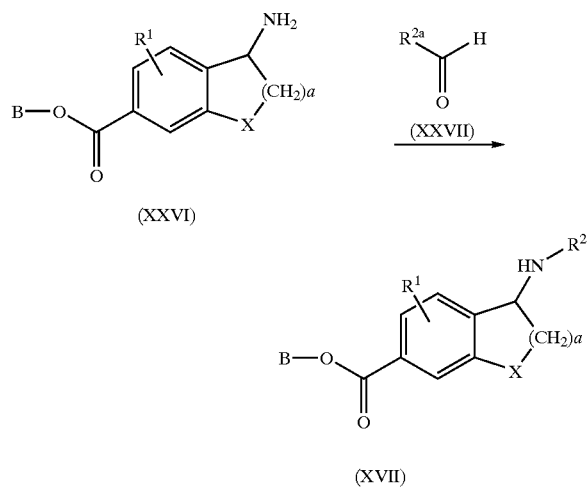

(XXVI)

(XVII)

wherein $R^{2a}$ is hydrogen, alkyl, phenyl or aralkyl, $R^2$ is alkyl or aralkyl, and other symbols are as defined above.

The objective compound (XVII) can be synthesized by reductive amination described for Method 2 of the compound of the formula (XXVI) [compound of the formula (XVII) wherein $R^2$ is hydrogen] and the compound of the formula (XXVII).

Method 11: The compound of the formula (XVII) can be synthesized by the following method.

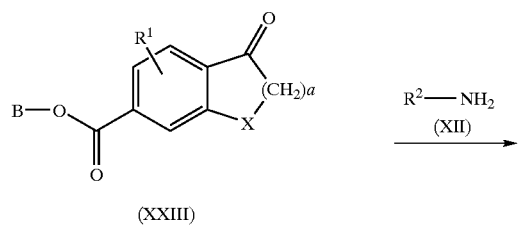

(XXIII)

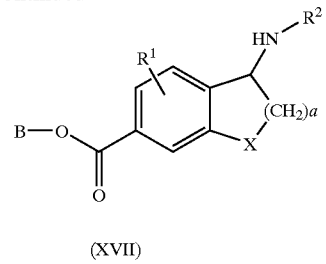

(XVII)

wherein each symbol is as defined above.

The compound (XVII) can be synthesized by subjecting the compound of the formula (XXIII) and compound (XII) to the reductive amination described in Method 2. The compound of the formula (XVII) wherein $R^2$ is hydrogen can be synthesized by using hydroxyamine instead of compound (XII).

The compound of the present invention can be isolated and purified by a method known in the field of the organic synthesis chemistry such as recrystallization, column chromatography and the like. When the obtained product is a racemate, it can be resolved into a desired optically active form by, for example, fractionation crystallization with a salt of an optically active acid or base, or by passing through a column packed with an optically active carrier. These optically active forms can be also produced by using an optically active starting material compound.

A pharmaceutically acceptable salt of the compound of the formula (I) can be formed by a conventional method. The acid to be used for forming an acid is appropriately selected from inorganic acids such as hydrochloric acid, hydrobromic acid, sulfuric acid and the like, organic acids such as methanesulfonic acid, fumaric acid, maleic acid, mandelic acid, citric acid, tartaric acid, salicylic acid and the like, amino acids such as lysin and the like, and metal such as sodium, potassium, calcium, magnesium, aluminum and the like. These acid addition salts can be converted to the corresponding free base according to a conventional method by, for example, reaction with alkali such as sodium hydroxide, potassium hydroxide and the like. It is possible to form a quaternary ammonium salt.

The compound of the formula (I) of the present invention thus formed shows a remarkable and selective Rho kinase inhibitory action, is free of problematic toxicity, shows fine oral absorption and drug kinetics (absorption, distribution, metabolism, excretion and the like of the drug), and shows superior properties (e.g., stability etc.) as a compound. Accordingly, it can be used as a therapeutic drug for various diseases in which Rho kinase is involved.

The compound of the present invention has an anti-cancer action, a cancer metastasis inhibitory action, an angiogenesis inhibitory action, an antihypertensive action, an anti-pulmonary hypertension action, an anti-angina pectoris action, a cerebrovascular contraction suppressive action, an anti-asthma action, a peripheral circulation improving action, an immature birth preventive action, an anti-arteriosclerosis action, an angiostenosis inhibitory action, an anti-inflammatory action, an analgesic action, an immunosuppressive action, an autoimmune disorder suppressive action, an anti-AIDS action, a preventive action of fertilization and nidation of fertilized egg, a bone formation promoting action, a bone resorption inhibitory action, a retinopathy treating action, a glaucoma treating action, a nerve axon regenerating action, a brain function improving action, a preventive action on cell infection of digestive tract, an inhibitory action on fibrosis of various organs, an erectile dysfunction treating action and a prophylactic or therapeutic action on ischemia-reperfusion injury, and can be an anticancer drug, a suppressive agent of metastasis of cancer, a suppressive agent of angiogenesis, an antihypertensive, an anti-pulmonary hypertension drug, an anti-angina pectoris drug, a cerebrovascular contraction suppressive agent, an anti-asthma drug, a peripheral circulation-improving drug, an early delivery-preventive drug, an anti-arteriosclerosis drug, a suppressive agent of angiostenosis, an anti-inflammatory agent, an analgesic, an immunosuppressant, a suppressive agent of autoimmune disorder, an anti-AIDS drug, an inhibitor of fertilization and implantation of fertilized egg, a bone formation-promoting drug, a bone resorption inhibitor, a therapeutic agent of retinopathy, a therapeutic agent of glaucoma, a nerve axon-regenerating drug, a brain function-improving drug, a preventive of cell infection of digestive tract, a suppressive agent of fibrosis of various organs, a therapeutic agent of erectile dysfunction or an agent for the prophylaxis or therapy of ischemia-reperfusion injury.

The compounds of the present invention have high affinity for Rho kinase. Thus, the labeled compounds thereof are industrially useful as selective ligands of Rho kinase. The compounds of the present invention and labeled compounds thereof (e.g., radio ligand of these compounds etc.) are useful as reagents for the study of Rho and Rho kinase and as diagnostics of the diseases relating to them.

When the compound of the present invention is used as the above-mentioned pharmaceutical agent, it is prepared into a general pharmaceutical preparation. For example, the Rho kinase inhibitor of the present invention is mixed with a pharmaceutically acceptable carrier (e.g., excipient, binder, disintegrator, corrective, corrigent, emulsifier, diluent, solubilizer etc.) to give a pharmaceutical composition or a pharmaceutical preparation in the form of tablet, pill, powder, granule, capsule, troche, syrup, liquid, emulsion, suspension, injection (e.g., liquid, suspension etc.), suppository, inhalant, percutaneous absorber, eye drop, eye ointment and the like in the form suitable for oral or parenteral preparation.

When preparing a solid preparation, an additive such as sucrose, lactose, cellulose sugar, D-mannitol, maltitol, dextran, starches, agar, arginates, chitins, chitosans, pectines, tragacanth, gum arabic, gelatins, collagens, casein, albumin, calcium phosphate, sorbitol, glycine, carboxymethyl cellulose, polyvinylpyrrolidone, hydroxypropylcellulose, hydroxypropylmethylcellulose, glycerol, polyethylene glycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil etc.), mineral fats and oils (e.g., petrolatum, white petrolatum, solid paraffin etc.), wax (e.g., jojoba oil, carnauba wax, bee wax etc.), partly or entirely synthesized glycerol fatty acid esters (e.g., lauric acid, myristic acid, palmitic acid etc.), and the like are used. Examples of commercially available products of these include Witepsol (manufactured by Dynamitnovel Ltd.), Farmazol (NOF Corporation) and the like.

When preparing a liquid preparation, an additive, such as sodium chloride, glucose, sorbitol, glycerol, olive oil, propylene glycol, ethyl alcohol and the like, is used. In particular, when preparing an injection, a sterile aqueous solution such as physiological saline, isotonizing liquid, oily liquid (e.g., sesame oil and soybean oil) and the like is used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The liquid for an eye drop can appropriately contain various additives such as buffer (preferred are borate buffer, acetate buffer, carbonate buffer and the like for less irritation), isotonizing agent, solubilizer, preservative, thickener, chelating agent, pH adjuster (preferably, pH is generally adjusted to about 6–8.5) and aromatic.

The content of the active ingredient in these preparation is 0.1–100 wt %, suitably 1–50 wt %, of the preparation. While subject to variation depending on the condition, body weight, age and the like of patient, in general, about 1–500 mg of the active ingredient is orally administered daily for an adult in a single dose or several doses.

The present invention is described in more detail in the following by way of Starting Material Synthetic Example, Example, Formulation Example and Experimental Example, to which the present invention is not limited.

In the Examples, Me means a methyl group, Za means a benzyloxycarbonyl group, Tr means a triphenylmethyl group, SEM means a 2-(trimethylsilyl)ethoxymethyl group.

STARTING MATERIAL SYNTHETIC EXAMPLE 1

4-hydroxythiochromane-7-carboxylic acid methyl ester

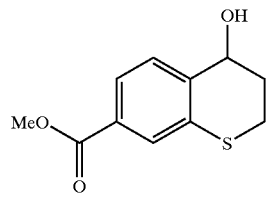

In a mixed solvent of ethanol (400 ml) and tetrahydrofuran (THF) (100 m) was dissolved 4-oxythiochromane-7-carboxylic acid methyl ester (20.0 g) synthesized by a known method (Ger. Offen. DE 19532312 A16 WO 9709327 A1), and sodium borohydride (3.41 g) was added at 0° C. The mixture was stirred at room temperature for 1 hr. To the reaction mixture was added water (500 ml) and the mixture was extracted with ethyl acetate. The organic layer was washed with saturated brine and dried over anhydrous magnesium sulfate. The solvent was concentrated under reduced pressure and the obtained residue was purified by silica gel column chromatography to give the objective 4-hydroxythiochromane-7-carboxylic acid methyl ester (19.6 g) as colorless crystals.

melting point: 79–81° C.

$^1$H-NMR(400 MHz, DMSO-$d_6$) δ=1.95–2.10(m, 2H), 2.90–3.05(m, 1H), 3.10–3.20(m, 1H), 3.82(s, 3H), 4.63(q, J=4 Hz, 1H), 5.57(d, J=4 Hz, 1H), 7.50(d, J=8 Hz, 1H), 7.59(s, 1H), 7.60(d, J=8 Hz, 1H).

STARTING MATERIAL SYNTHETIC EXAMPLE 2

4-azidethiochromane-7-carboxylic acid methyl ester

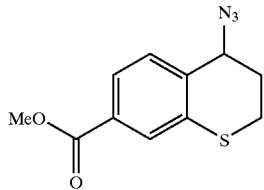

To a THF (500 ml) solution of 4-hydroxythiochromane-7-carboxylic acid methyl ester (19.0 g) and diphenyl phosphorazide (28.0 g) was added 1,8-diazabicyclo[5.4.0]-undecene (15.5 g) at 0° C., and the mixture was stirred at room temperature for 3 days. Water (500 ml) was added to the reaction mixture and the mixture was extracted with ethyl acetate. The organic layer was washed with 1N hydrochloric acid, water and saturated brine, and dried over anhydrous magnesium sulfate. The solvent was concentrated under reduced pressure and the obtained residue was purified by silica gel column chromatography to give a crude product (17.0 g) of the objective 4-azidethiochromane-7-carboxylic acid methyl ester as a colorless oil.

$^1$H-NMR(400 MHz, DMSO-$d_6$) δ=1.95–2.10(m, 1H), 2.25–2.35(m, 1H), 3.00–3.10(m, 1H), 3.10–3.25(m, 1H), 3.83(s, 3H), 5.04(t, J=4 Hz, 1H), 7.49(d, J=8 Hz, 1H), 7.66(d, J=8 Hz, 1H), 7.68(s, 1H).

STARTING MATERIAL SYNTHETIC EXAMPLE 3

4-aminothiochromane-7-carboxylic acid methyl ester

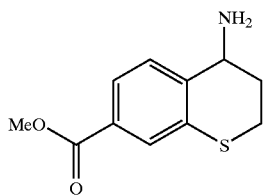

To a methanol (200 ml) solution of 4-azidethiochromane-7-carboxylic acid methyl ester (17.0 g) was added stannous chloride 2 hydrate (46.3 g), and the mixture was stirred under reflux for 5 hr. The reaction mixture was poured into saturated aqueous sodium hydrogencarbonate solution (500 ml) and the mixture was filtered through celite. The filtrate was extracted with chloroform, washed with water, saturated aqueous sodium hydrogencarbonate solution and saturated brine, and dried over anhydrous magnesium sulfate. The solvent was concentrated under reduced pressure and the obtained residue was purified by silica gel column chromatography to give the objective 4-aminothiochromane-7-carboxylic acid methyl ester (8.04 g) as a colorless oil.

$^1$H-NMR(400 MHz, DMSO-$d_6$) δ=1.90–2.05(m, 2H), 2.90–3.00(m, 1H), 3.15–3.30(m, 1H), 3.81(s, 3H), 3.90(t, J=4 Hz, 1H), 7.50–7.65(m, 3H).

STARTING MATERIAL SYNTHETIC EXAMPLE 4

4-(benzyloxycarbonylamino)thiochromane-7-carboxylic acid methyl ester

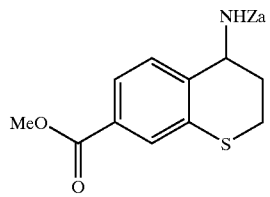

To an ethyl acetate (200 ml) solution of 4-aminothiochromane-7-carboxylic acid methyl ester (8.00 g) was added saturated aqueous sodium hydrogencarbonate solution (200 ml), and benzyloxycarbonyl chloride (6.75 g) was added at room temperature. The mixture was stirred at the same temperature for 2 hrs. The reaction mixture was extracted with ethyl acetate, washed with water, saturated aqueous sodium hydrogencarbonate solution and saturated brine, and dried over anhydrous magnesium sulfate. The solvent was concentrated under reduced pressure and the obtained residue was purified by silica gel column chromatography to give the objective 4-(benzyloxycarbonylamino)thiochromane-7-carboxylic acid methyl ester (12.8 g) as colorless crystals.

melting point: 128–130° C.

STARTING MATERIAL SYNTHETIC EXAMPLE 5

4-(benzyloxycarbonylamino)-1,1-dioxythiochromane-7-carboxylic acid methyl ester

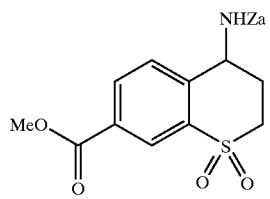

To a methylene chloride (200 ml) solution of 4-(benzyloxycarbonylamino)thiochromane-7-carboxylic acid methyl ester (8.50 g) was added 70% meta-chloroperbenzoic acid (12.9 g) at room temperature and the mixture was stirred at room temperature for 1 hr. To the reaction mixture were added saturated aqueous sodium hydrogencarbonate solution (100 ml) and saturated aqueous sodium thiosulfate solution (100 ml) and the mixture was extracted with chloroform. The obtained organic layer was washed with water and saturated brine, dried over anhydrous magnesium sulfate. The solvent was concentrated under reduced pressure, and the obtained residue was purified by silica gel column chromatography to give the objective 4-(benzyloxycarbonylamino)-1,1-dioxythiochromane-7-carboxylic acid methyl ester (7.23 g) as colorless crystals.

melting point: 139–140° C.

STARTING MATERIAL SYNTHETIC EXAMPLE 6

4-(benzyloxycarbonylamino)-1,1-dioxythiochromane-7-carboxylic acid

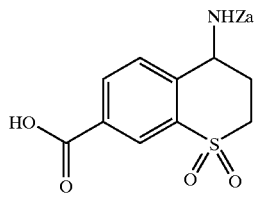

To a mixed solution of 4-(benzyloxycarbonylamino)-1,1-dioxythiochromane-7-carboxylic acid methyl ester (4.00 g) in methanol (200 ml) and water (50 ml) was added potassium carbonate (10.0 g) and the mixture was stirred under reflux for 2 hr. Then dilute hydrochloric acid was added until the reaction mixture had pH 1, and the precipitated crystals were collected by filtration. The crystals was dissolved in a mixed solvent of methylene chloride (200 ml) and dioxane (50 ml) and dried over anhydrous magnesium sulfate. The solvent was concentrated to give the objective 4-(benzyloxycarbonylamino)-1,1-dioxythiochromane-7-carboxylic acid (3.73 g) as a colorless amorphous solid.

$^1$H-NMR(400 MHz, DMSO-d$_6$) δ=2.40–2.50(m, 2H), 3.65–3.75(m, 1H), 3.75–3.85(m, 1H), 5.12(br.s, 3H), 7.30–7.40(m, 6H), 7.56(d, J=8 Hz, 1H), 8.14(d, J=8 Hz, 1H), 8.24(s, 1H), 13.55(br.s, 1H).

STARTING MATERIAL SYNTHETIC EXAMPLE 7

4-(benzyloxycarbonylamino)-1,1-dioxy-N-(4-pyridyl)thiochromane-7-carboxamide

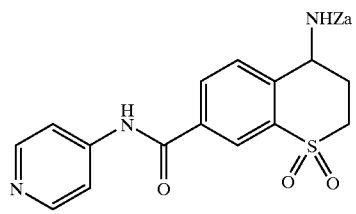

4-(Benzyloxycarbonylamino)-1,1-dioxythiochromane-7-carboxylic acid (4.00 g) was suspended in chloroform (150 ml) and thionyl chloride (3.43 g) and N,N-dimethylformamide (3.0 ml) were added. This mixture was refluxed under heating and stirred for 1 hr. The reaction system was cooled to room temperature and the solvent was evaporated under reduced pressure. The obtained crystals were dissolved in acetonitrile (25 ml) and added dropwise to a solution of 4-aminopyridine (903 mg) and triethylamine (1.94 g) in acetonitrile (50 ml) at 0° C. The mixture was allowed to warm to room temperature and continuously stirred for 2 hr. Water (500 ml) was added to the reaction mixture and the mixture was extracted with ethyl acetate. The obtained organic layer was washed with water and saturated brine, and dried over anhydrous magnesium sulfate. The solvent was concentrated under reduced pressure and the obtained residue was purified by silica gel column chromatography to give the objective 4-(benzyloxycarbonylamino)-1,1-dioxy-N-(4-pyridyl)thiochromane-7-carboxamide (2.02 g) as colorless crystals.

melting point: 217–220° C. (decomposition).

STARTING MATERIAL SYNTHETIC EXAMPLE 8

4-(benzyloxycarbonylamino)thiochromane-7-carboxylic acid

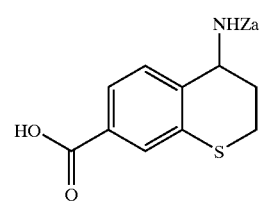

To a mixed solution of 4-(benzyloxycarbonylamino)thiochromane-7-carboxylic acid methyl ester (3.20 g) in methanol (50 ml), tetrahydrofuran (100 ml) and water (50 ml) was added 1N aqueous sodium hydroxide solution (20 ml), and the mixture was stirred at room temperature for 5 hr. Dilute hydrochloric acid was added to the reaction mixture until the pH became 1, and the precipitated crystals were collected by filtration. The crystals were recrystallized from acetone-hexane to give the objective 4-(benzyloxycarbonylamino)thiochromane-7-carboxylic acid (2.74 g) as colorless crystals.

melting point: 202–205° C.

$^1$H-NMR(400 MHz, DMSO-d$_6$) δ=2.05–2.15(m, 2H), 3.00–3.10(m, 2H), 4.79(q, J=4 Hz, 1H), 5.08(s, 2H), 7.30–7.40(m, 6H), 7.58(d, J=9 Hz, 1H), 7.59(s, 1H), 7.91(d, J=9 Hz, 1H), 13.00(br.s, 1H).

STARTING MATERIAL SYNTHETIC EXAMPLE 9

4-(benzyloxycarbonylamino)-N-(4-pyridyl)thiochromane-7-carboxamide

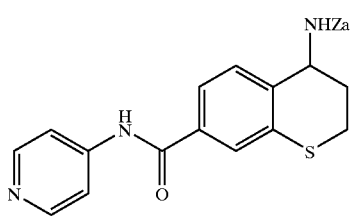

4-(Benzyloxycarbonylamino)thiochromane-7-carboxylic acid (2.80 g) was suspended in dichloromethane (120 ml), and oxalyl chloride (2.07 g) and N,N-dimethylformamide (15 ml) were added. This mixture was stirred at room temperature for 1 hr and the solvent was evaporated under reduced pressure. The obtained acid chloride was dissolved in acetonitrile (25 ml) and N,N-dimethylformamide (20 ml) and added dropwise to a solution of 4-aminopyridine (768 mg) and triethylamine (1.55 g) in acetonitrile (50 ml) at 0° C. The mixture was allowed to warm to room temperature and continuously stirred for 30 min. 4-Aminopyridine (768 mg) and triethylamine (1.55 g) were added to the reaction mixture and this suspension was further stirred at room temperature for 3 hr. The precipitated crystals were removed by suction filtration. The obtained the filtrate was stood overnight at 0° C. and the precipitated crystals were dried under reduced pressure to give the objective 4-(benzyloxycarbonylamino)-N-(4-pyridyl)thiochromane-7-carboxamide (1.57 g) as colorless crystals.

melting point: 223–225° C. (decomposition).

STARTING MATERIAL SYNTHETIC EXAMPLE 10

5-hydroxy-5,6,7,8-tetrahydronaphthalene-2-carboxylic acid methyl ester

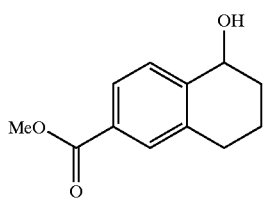

By a similar reaction operation as in Starting Material Synthetic Example 1 using 5-oxo-5,6,7,8-tetrahydronaphthalene-2-carboxylic acid methyl ester (3.50 g) obtained by a known method and sodium borohydride (650 mg), the objective 5-hydroxy-5,6,7,8-tetrahydronaphthalene-2-carboxylic acid methyl ester (3.54 g) was obtained as a pale yellow oil.

$^1$H-NMR(400 MHz, CDCl$_3$) δ=1.69(s, 1H), 1.70–2.25(m, 4H), 2.70–3.00(m, 2H), 3.91(s, 3H), 4.81(t, J=5 Hz, 1H), 7.53(d, J=7 Hz, 1H), 7.79(s, 1H), 7.58(d, J=7 Hz, 1H).

STARTING MATERIAL SYNTHETIC EXAMPLE 11

5-azide-5,6,7,8-tetrahydronaphthalene-2-carboxylic acid methyl ester

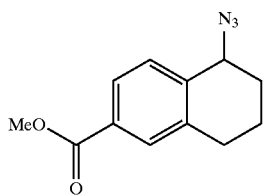

By a similar reaction operation as in Starting Material Synthetic Example 2 using 5-hydroxy-5,6,7,8-tetrahydronaphthalene-2-carboxylic acid methyl ester (3.50 g), diphenyl phosphorazide (5.61 g) and 1,8-diazabicyclo[5.4.0]-undecene (3.10 g), a crude product (3.50 g) of the objective 5-azide-5,6,7,8-tetrahydronaphthalene-2-carboxylic acid methyl ester was obtained as a pale yellow oil.

$^1$H-NMR(400 MHz, CDCl$_3$) δ=1.75–1.90(m, 1H), 1.90–2.10(m, 3H), 2.70–3.00(m, 2H), 3.91(s, 3H), 4.59(t, J=5 Hz, 1H), 7.38(d, J=8 Hz, 1H), 7.83(s, 1H), 7.87(d, J=8 Hz, 1H).

STARTING MATERIAL SYNTHETIC EXAMPLE 12

5-amino-5,6,7,8-tetrahydronaphthalene-2-carboxylic acid methyl ester

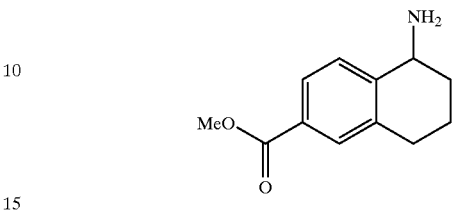

To a mixed solution of a crude product (3.50 g) of 5-azide-5,6,7,8-tetrahydronaphthalene-2-carboxylic acid methyl ester in THF (100 ml) and water (10 ml) was added triphenylphosphine (5.34 g), and the mixture was reacted under reflux overnight. The reaction mixture was concentrated under reduced pressure and 1N hydrochloric acid (200 ml) was added. The aqueous layer was washed with ethyl acetate. To the obtained aqueous layer was added potassium carbonate to make the solution alkaline, and the mixture was extracted with ethyl acetate. The extracted organic layer was washed with saturated brine, and dried over anhydrous sodium sulfate. This solution was concentrated under reduced pressure to give the objective 5-amino-5,6,7,8-tetrahydronaphthalene-2-carboxylic acid methyl ester (2.56 g) as a yellow oil.

$^1$H-NMR(400 MHz, CDCl$_3$) δ=1.60–2.40(m, 6H), 2.70–3.00(m, 2H), 3.90(s, 3H), 4.02(br.s, 1H), 7.48(d, J=8 Hz, 1H), 7.77(s, 1H), 7.82(d, J=8 Hz, 1H).

STARTING MATERIAL SYNTHETIC EXAMPLE 13

5-(benzyloxycarbonylamino)-5,6,7,8-tetrahydronaphthalene-2-carboxylic acid methyl ester

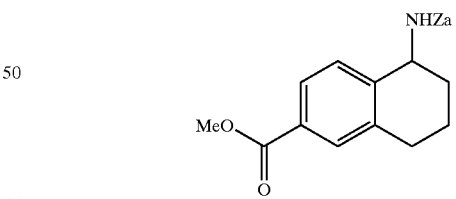

By a similar reaction operation as in Starting Material Synthetic Example 4 using 5-amino-5,6,7,8-tetrahydronaphthalene-2-carboxylic acid methyl ester (2.50 g) and benzyloxycarbonyl chloride (3.13 g), the objective 5-(benzyloxycarbonylamino)-5,6,7,8-tetrahydronaphthalene-2-carboxylic acid methyl ester (3.53 g) as colorless crystals.

melting point: 83–84° C.

STARTING MATERIAL SYNTHETIC EXAMPLE 14

5-(benzyloxycarbonylamino)-5,6,7,8-tetrahydronaphthalene-2-carboxylic acid

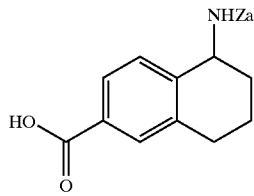

By a similar reaction operation as in Starting Material Synthetic Example 8 using 5-(benzyloxycarbonylamino)-5,6,7,8-tetrahydronaphthalene-2-carboxylic acid methyl ester (3.50 g) and 1N aqueous sodium hydroxide solution (20 ml), the objective 5-(benzyloxycarbonylamino)-5,6,7,8-tetrahydronaphthalene-2-carboxylic acid (2.79 g) was obtained as colorless crystals.

melting point: 203–205° C.

$^1$H-NMR(400 MHz, CDCl$_3$-D$_2$O substitution) δ=1.75–1.95(m, 3H), 2.00–2.20(m, 1H), 2.70–2.95(m, 2H), 4.90–5.05(m, 2H), 5.24(s, 1H), 7.25–7.40(m, 5H), 7.44(d, J=8 Hz, 1H), 7.84(s, 1H), 7.86(d, J=8 Hz, 1H).

STARTING MATERIAL SYNTHETIC EXAMPLE 15

5-(benzyloxycarbonylamino)-N-(4-pyridyl)-5,6,7,8-tetrahydronaphthalene-2-carboxamide

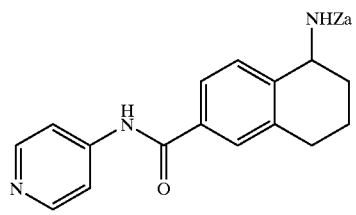

By a similar reaction operation as in Starting Material Synthetic Example 7 using 5-(benzyloxycarbonylamino)-5,6,7,8-tetrahydronaphthalene-2-carboxylic acid (2.50 g), thionyl chloride (2.75 g), 4-aminopyridine (724 mg) and triethylamine (1.55 g), the objective 5-(benzyloxycarbonylamino)-N-(4-pyridyl)-5,6,7,8-tetrahydronaphthalene-2-carboxamide (1.03 g) was obtained as colorless crystals.

melting point: 157–159° C.

STARTING MATERIAL SYNTHETIC EXAMPLE 16

5-oxo-2,3,4,5-tetrahydro-1-benzothiepine-8-carbonitrile

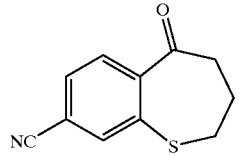

To a solution of 8-bromo-5-oxo-2,3,4,5-tetrahydro-1-benzothiepine (5.00 g) synthesized according to a known method in N,N-dimethylformamide (50 ml) were added zinc cyanide (2.28 g) and tetrakis(triphenylphosphine)palladium (0) (1.13 g) and the mixture was stirred at 80–90° C. for 1 hr. The reaction mixture was allowed to warm to room temperature and water (500 ml) and ethyl acetate (100 ml) were added. The mixture was passed through celite. The filtrate was extracted with ethyl acetate and the organic layer was washed with water and dried over anhydrous magnesium sulfate. The solvent was concentrated under reduced pressure and the obtained residue was recrystallized from ethyl acetate and hexane to give the objective 5-oxo-2,3,4,5-tetrahydro-1-benzothiepine-8-carbonitrile (3.37 g) as pale yellow crystals.

melting point: 109–111° C.

STARTING MATERIAL SYNTHETIC EXAMPLE 17

5-oxo-2,3,4,5-tetrahydro-1-benzothiepine-8-carboxylic acid methyl ester

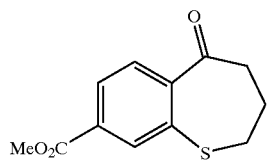

To an acetic acid (20 ml) solution of 5-oxo-2,3,4,5-tetrahydro-1-benzothiepine-8-carbonitrile (3.20 g) was added concentrated hydrochloric acid (20 ml) and the mixture was reacted under reflux overnight. The reaction mixture was allowed to warm to room temperature and water (350 ml) was added. The precipitated crystals were collected by filtration and the collected crystals were dissolved in ethyl acetate (400 ml). The mixture was dried over anhydrous magnesium sulfate and the solvent was concentrated under reduced pressure to give a crude product (3.42 g) of 5-oxo-2,3,4,5-tetrahydro-1-benzothiepine-8-carboxylic acid.

This 5-oxo-2,3,4,5-tetrahydro-1-benzothiepine-8-carboxylic acid (3.42 g) was dissolved in methanol (100 ml) and 4N hydrochloric acid dioxane solution (15 ml) was added. The mixture was stirred under reflux for 3 hr. The reaction mixture was cooled to room temperature and saturated aqueous sodium hydrogencarbonate solution (250 ml) was added. The mixture was extracted with ethyl acetate. The obtained organic layer was washed with water, saturated aqueous sodium hydrogencarbonate solution and saturated brine, and dried over anhydrous magnesium sulfate. The solvent was concentrated under reduced pressure to give the objective 5-oxo-2,3,4,5-tetrahydro-1-benzothiepine-8-carboxylic acid methyl ester (3.35 g) as colorless crystals.

melting point: 63–64° C.

STARTING MATERIAL SYNTHETIC EXAMPLE 18

5-hydroxy-2,3,4,5-tetrahydro-1-benzothiepine-8-carboxylic acid methyl ester

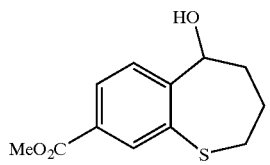

By a similar reaction operation as in Starting Material Synthetic Example 1 using 5-oxo-2,3,4,5-tetrahydro-1-benzothiepine-8-carboxylic acid methyl ester (3.30 g) and sodium borohydride (529 mg), the objective 5-hydroxy-2,3,4,5-tetrahydro-1-benzothiepine-8-carboxylic acid methyl ester (3.26 g) was obtained a pale yellow oil.

$^1$H-NMR(400 MHz, CDCl$_3$) δ=1.65–1.85(m, 1H), 2.00–2.20(m, 4H), 2.55–2.65(m, 1H), 2.75–2.85(m, 1H), 3.91(s, 3H), 5.30(d, J=7 Hz, 1H), 7.61(d, J=8 Hz, 1H), 7.97(dd, J=2 Hz, J=8 Hz, 1H), 8.17(d, J=2 Hz, 1H).

STARTING MATERIAL SYNTHETIC EXAMPLE 19

5-azide-2,3,4,5-tetrahydro-1-benzothiepine-8-carboxylic acid methyl ester

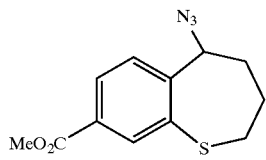

By a similar reaction operation as in Starting Material Synthetic Example 2 using 5-hydroxy-2,3,4,5-tetrahydro-1-benzothiepine-8-carboxylic acid methyl ester (3.30 g), diphenyl phosphorazide(15.3 g) and 1,8-diazabicyclo[5.4.0]undecene (8.46 g) (the reaction was carried out at 50–60° C.), a crude product (3.02 g) of the objective 5-azide-2,3,4,5-tetrahydro-1-benzothiepine-8-carboxylic acid methyl ester was obtained as a pale yellow oil.

$^1$H-NMR(400 MHz, CDCl$_3$) δ=1.60–1.70(m, 1H), 2.00–2.25(m, 3H), 2.55–2.65(m, 1H), 2.85–2.95(m, 1H), 3.92(s, 3H), 5.33(dd, J=2 Hz, J=10 Hz, 1H), 7.57(d, J=8 Hz, 1H), 7.99(dd, J=2 Hz, J=8 Hz, 1H), 8.21(d, J=2 Hz, 1H).

STARTING MATERIAL SYNTHETIC EXAMPLE 20

5-amino-2,3,4,5-tetrahydro-1-benzothiepine-8-carboxylic acid methyl ester

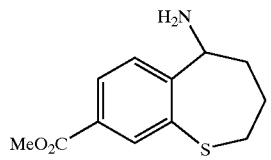

By a similar reaction operation as in Starting Material Synthetic Example 12 using a crude product (3.00 g) of 5-azide-2,3,4,5-tetrahydro-1-benzothiepine-8-carboxylic acid methyl ester and triphenylphosphine (5.97 g), a crude product (2.64 g) of the objective 5-amino-2,3,4,5-tetrahydro-1-benzothiepine-8-carboxylic acid methyl ester was obtained as a yellow oil.

$^1$H-NMR(400 MHz, CDCl$_3$) δ=1.60–1.75(m, 1H), 1.85–2.00(m, 1H), 2.00–2.20(m, 4H), 2.60–2.70(m, 1H), 2.75–2.85(m, 1H), 3.91(s, 3H), 4.64(dd, J=1 Hz, J=7 Hz, 1H), 7.56(d, J=8 Hz, 1H), 7.95(dd, J=2 Hz, J=8 Hz, 1H), 8.17(d, J=2 Hz, 1H).

STARTING MATERIAL SYNTHETIC EXAMPLE 21

5-(benzyloxycarbonylamino)-2,3,4,5-tetrahydro-1-benzothiepine-8-carboxylic acid methyl ester

By a similar reaction operation as in Starting Material Synthetic Example 4 using 5-amino-2,3,4,5-tetrahydro-1-benzothiepine-8-carboxylic acid methyl ester (2.50 g) and benzyloxycarbonyl chloride (2.69 g), the objective 5-(benzyloxycarbonylamino)-2,3,4,5-tetrahydro-1-benzothiepine-8-carboxylic acid methyl ester (3.53 g) was obtained as colorless crystals.

melting point: 132–134° C.

STARTING MATERIAL SYNTHETIC EXAMPLE 22

5-(benzyloxycarbonylamino)-1,1-dioxy-2,3,4,5-tetrahydro-1-benzothiepine-8-carboxylic acid methyl ester

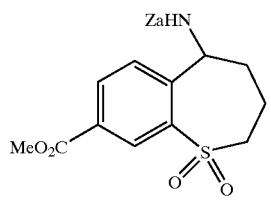

By a similar reaction operation as in Starting Material Synthetic Example 5 using 5-(benzyloxycarbonylamino)-2, 3,4,5-tetrahydro-1-benzothiepine-8-carboxylic acid methyl ester (2.75 g) and 70% meta-chloroperbenzoic acid (5.49 g), the objective 5-(benzyloxycarbonylamino)-1,1-dioxy-2,3,4,5-tetrahydro-1-benzothiepine-8-carboxylic acid methyl ester (2.79 g) was obtained as colorless crystals.

melting point: 137–139° C.

STARTING MATERIAL SYNTHETIC EXAMPLE 23

5-(benzyloxycarbonylamino)-1,1-dioxy-2,3,4,5-tetrahydro-1-benzothiepine-8-carboxylic acid

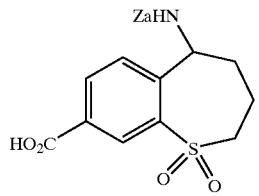

By a similar reaction operation as in Starting Material Synthetic Example 8 using 5-(benzyloxycarbonylamino)-1,1-dioxy-2,3,4,5-tetrahydro-1-benzothiepine-8-carboxylic acid methyl ester (3.00 g) and 1N aqueous sodium hydroxide solution (15 ml), the objective 5-(benzyloxycarbonylamino)-1,1-dioxy-2,3,4,5-tetrahydro-1-benzothiepine-8-carboxylic acid (2.58 g) was obtained as colorless crystals.

melting point: 213–215° C.

$^1$H-NMR(400 MHz, CDCl$_3$-D$_2$O substitution) δ=1.85 (br.t, J=10 Hz, 1H), 2.10–2.70(m, 3H), 3.23(br.t, J=14 Hz, 1H), 3.65–3.75(m, 1H), 5.11(dd, J=12 Hz, J=30 Hz, 2H), 5.49(br.t, J=4 Hz, 1H), 6.65(br.s, 1H), 7.20–7.40(m, 5H), 7.67(d, J=8 Hz, 1H), 8.30(d, J=8 Hz, 2H), 8.81(s, 1H).

STARTING MATERIAL SYNTHETIC EXAMPLE 24

5-(benzyloxycarbonylamino)-1,1-dioxy-N-(4-pyridyl)-2,3,4,5-tetrahydro-1-benzothiepine-8-carboxamide

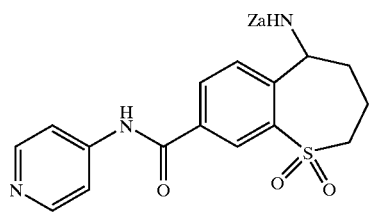

By a similar reaction operation as in Starting Material Synthetic Example 7 using 5-(benzyloxycarbonylamino)-1,1-dioxy-2,3,4,5-tetrahydro-1-benzothiepine-8-carboxylic acid (2.35 g), thionyl chloride (2.16 g), 4-aminopyridine (568 mg) and triethylamine (1.22 g), the objective 5-(benzyloxycarbonylamino)-1,1-dioxy-N-(4-pyridyl)-2,3,4,5-tetrahydro-1-benzothiepine-8-carboxamide (1.93 g) was obtained as colorless crystals.

melting point: 230–231° C.

STARTING MATERIAL SYNTHETIC EXAMPLE 25

4-hydroxychromane-7-carboxylic acid methyl ester

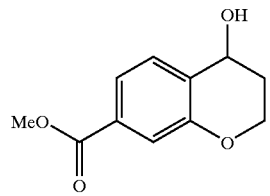

By a similar reaction operation as in Starting Material Synthetic Example 1 using 4-oxochromane-7-carboxylic acid methyl ester (1.4 g) synthesized according to a known method and sodium borohydride (0.26 g), the objective 4-hydroxychromane-7-carboxylic acid methyl ester (1.5 g) was obtained as a colorless oil.

$^1$H-NMR(400 MHz, CDCl$_3$) δ=1.89(br.s, 1H), 2.0–2.2(m, 2H), 3.90(s, 3H), 4.25–4.35(m, 2H), 4.8–4.9(m, 1H), 7.35–7.45(m, 1H), 7.51(s, 1H), 7.5–7.6(m, 1H).

STARTING MATERIAL SYNTHETIC EXAMPLE 26

4-azidechromane-7-carboxylic acid methyl ester

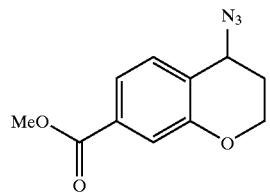

By a similar reaction operation as in Starting Material Synthetic Example 2 using 4-hydroxychromane-7-carboxylic acid methyl ester (1.4 g), diphenyl phosphorazide (3.7 g) and 1,8-diazabicyclo[5.4.0]undecene (2.0 g), a mixture (2:1) (2.6 g) of the objective 4-azidechromane-7-carboxylic acid methyl ester and diphenyl phosphorazide was obtained as a pale yellow oil.

$^1$H-NMR(400 MHz, CDCl$_3$) δ=2.0–2.3(m, 2H), 3.91(s, 3H), 4.2–4.4(m, 2H), 4.6–4.65(m, 1H), 7.2–7.4(m, 1H), 7.55(s, 1H), 7.60(d, J=9 Hz, 1H).

STARTING MATERIAL SYNTHETIC EXAMPLE 27

4-aminochromane-7-carboxylic acid methyl ester

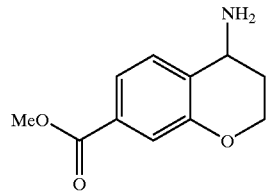

By a similar reaction operation as in Starting Material Synthetic Example 12 using a mixture (2.6 g) of 4-azidechromane-7-carboxylic acid methyl ester and diphenyl phosphorazide and triphenylphosphine (3.9 g), the objective 4-aminochromane-7-carboxylic acid methyl ester (1.4 g) was obtained as a pale yellow oil.

$^1$H-NMR(400 MHz, CDCl$_3$) δ=1.57(br.s, 2H), 1.8–1.9(m, 1H), 2.1–2.2(m, 1H), 3.89(s, 3H), 4.07(t, J=5 Hz, 1H), 4.2–4.4(m, 2H), 7.38(d, J=9 Hz, 1H), 7.48(d, J=3 Hz, 1H), 7.56(dd, J=9 Hz, J=3 Hz, 1H).

STARTING MATERIAL SYNTHETIC EXAMPLE 28

4-(benzyloxycarbonylamino)chromane-7-carboxylic acid methyl ester

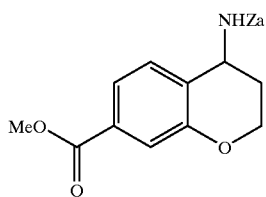

By a similar reaction operation as in Starting Material Synthetic Example 4 using 4-aminochromane-7-carboxylic acid methyl ester (1.4 g) and benzyloxycarbonyl chloride (2.0 ml), the objective 4-(benzyloxycarbonylamino) chromane-7-carboxylic acid methyl ester (1.9 g) was obtained as colorless crystals.

melting point: 140–142° C.

$^1$H-NMR(400 MHz, CDCl$_3$) δ=2.0–2.1(m, 1H), 2.1–2.3 (m, 1H), 3.89(s, 3H), 4.1–4.3(m, 2H), 4.9–5.1(m, 2H), 5.16(s, 2H), 7.2–7.4(m, 6H), 7.47(s, 1H), 7.54(d, J=8 Hz, 1H).

STARTING MATERIAL SYNTHETIC EXAMPLE 29

4-(benzyloxycarbonylamino)chromane-7-carboxylic acid

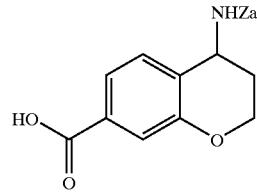

By a similar reaction operation as in Starting Material Synthetic Example 8 using 4-(benzyloxycarbonylamino) chromane-7-carboxylic acid methyl ester (1.9 g) and 1N sodium hydroxide (14 ml), the objective 4-(benzyloxycarbonylamino)chromane-7-carboxylic acid (1.7 g) was obtained as colorless crystals.

melting point: 227–228° C.

$^1$H-NMR(400 MHz, DMSO-d$_6$) δ=1.9–2.0(m, 1H), 2.0–2.1(m, 1H), 4.2–4.3(m, 2H), 4.8–4.9(m, 1H), 5.10(s, 2H), 7.2–7.5(m, 8H), 7.88(d, J=8 Hz, 1H), 12.93(brs, 1H).

STARTING MATERIAL SYNTHETIC EXAMPLE 30

4-(benzyloxycarbonylamino)-N-(4-pyridyl) chromane-7-carboxamide

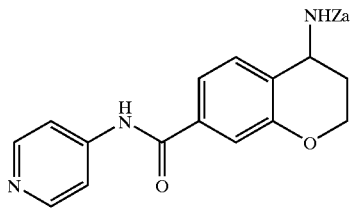

By a similar reaction operation as in Starting Material Synthetic Example 7 using 4-(benzyloxycarbonylamino) chromane-7-carboxylic acid (1.6 g), thionyl chloride (1.2 ml) and 4-aminopyridine (480 mg), the objective 4-(benzyloxycarbonylamino)-N-(4-pyridyl)chromane-7-carboxamide (2.34 g) was obtained as colorless crystals.

melting point: 226–228° C.

$^1$H-NMR(400 MHz, DMSO-d$_6$) δ=1.9–2.0(m, 1H), 2.05–2.15(m, 1H), 4.25–4.35(m, 2H), 4.8–4.9(m, 1H), 5.11 (s, 2H), 7.3–7.4(m, 7H), 7.47(d, J=8 Hz, 1H), 7.78(d, J=6 Hz, 2H), 7.92(d, J=8 Hz, 1H), 8.46(d, J=6 Hz, 2H), 10.51 (br.s, 1H).

STARTING MATERIAL SYNTHETIC EXAMPLE 31

(S)-4-hydroxythiochromane-7-carboxylic acid methyl ester

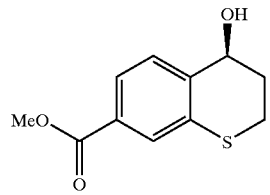

To a methylene chloride (160 ml) solution of (R)-5,5-diphenyl-2-methyl-3,4-propano-1,3,2-oxazaborolidine was added a borane-methyl sulfide complex (2.0 M toluene solution, 36.0 ml) at −20° C. and the mixture was stirred at the same temperature for 10 min. Then, to this solution was added dropwise a solution of 4-oxythiochromane-7-carboxylic acid methyl ester (8.00 g) synthesized according to a known method in methylene chloride (80 ml) at −20° C. to −10° C. The reaction mixture was heated to about 10° C., and stirred for 2 hrs. Methanol (15 ml) and 1N hydrochloric acid (300 ml) were added to the reaction mixture and the mixture was stirred at room temperature for 20 min. This mixed solution was extracted with chloroform, and the organic layer was washed with water and saturated brine and dried over anhydrous magnesium sulfate. The solvent was concentrated under reduced pressure and the obtained residue was recrystallized from chloroform-hexane to give the objective (S)-4-hydroxythiochromane-7-carboxylic acid methyl ester (7.29 g) as colorless crystals.

melting point: 118–120° C.

$^1$H-NMR(400 MHz, DMSO-d$_6$) δ=1.95–2.10(m, 2H), 2.90–3.05(m, 1H), 3.10–3.20(m, 1H), 3.82(s, 3H), 4.63(q, J=4 Hz, 1H), 5.57(d, J=4 Hz, 1H), 7.50(d, J=8 Hz, 1H), 7.59(s, 1H), 7.60(d, J=8 Hz, 1H).

STARTING MATERIAL SYNTHETIC EXAMPLE 32

(R)-4-azidethiochromane-7-carboxylic acid methyl ester

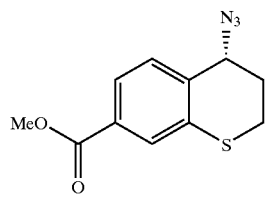

By a similar reaction operation as in Starting Material Synthetic Example 2 using (S)-4-hydroxythiochromane-7-carboxylic acid methyl ester (7.00 g), diphenyl phosphorazide (17.2 g) and 1,8-diazabicyclo[5.4.0]undecene (9.52 g), a crude product (7.93 g) of the objective (R)-4-azidethiochromane-7-carboxylic acid methyl ester was obtained as a pale yellow oil.

$^1$H-NMR(400 MHz, DMSO-d$_6$) δ=1.95–2.10(m, 1H), 2.25–2.35(m, 1H), 3.00–3.10(m, 1H), 3.10–3.25(m, 1H), 3.83(s, 3H), 5.04(t, J=4 Hz, 1H), 7.49(d, J=8 Hz, 1H), 7.66(d, J=8 Hz, 1H), 7.68(s, 1H).

STARTING MATERIAL SYNTHETIC EXAMPLE 33

(R)-4-aminothiochromane-7-carboxylic acid methyl ester

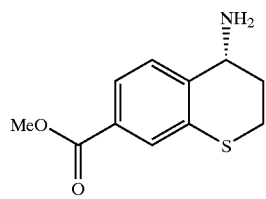

By a similar reaction operation as in Starting Material Synthetic Example 12 using a crude product (7.93 g) of (R)-4-azidethiochromane-7-carboxylic acid methyl ester and triphenylphosphine (12.3 g), the objective (R)-4-aminothiochromane-7-carboxylic acid methyl ester (5.76 g) was obtained as a pale yellow oil.

$^1$H-NMR(400 MHz, DMSO-d$_6$) δ=1.90–2.05(m, 2H), 2.90–3.00(m, 1H), 3.15–3.30(m, 1H), 3.81(s, 3H), 3.90(t, J=4 Hz, 1H), 7.50–7.65(m, 3H).

STARTING MATERIAL SYNTHETIC EXAMPLE 34

(R)-4-(benzyloxycarbonylamino)thiochromane-7-carboxylic acid methyl ester

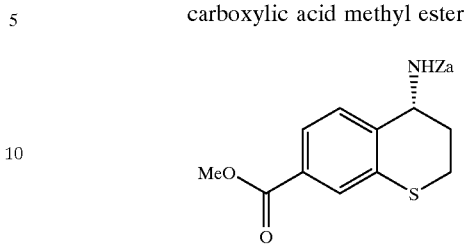

By a similar reaction operation as in Starting Material Synthetic Example 4 using (R)-4-aminothiochromane-7-carboxylic acid methyl ester (5.70 g) and benzyloxycarbonyl chloride (5.50 ml), the objective (R)-4-(benzyloxycarbonylamino)thiochromane-7-carboxylic acid methyl ester (7.35 g) was obtained as colorless crystals.

melting point: 139–140° C.

STARTING MATERIAL SYNTHETIC EXAMPLE 35

(R)-4-(benzyloxycarbonylamino)-1,1-dioxythiochromane-7-carboxylic acid methyl ester

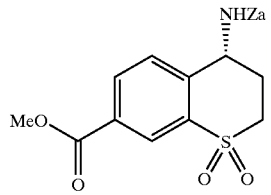

By a similar reaction operation as in Starting Material Synthetic Example 5 using (R)-4-(benzyloxycarbonylamino)thiochromane-7-carboxylic acid methyl ester (7.20 g) and 70% meta-chloroperbenzoic acid (15.0 g), the objective (R)-4-(benzyloxycarbonylamino)-1,1-dioxythiochromane-7-carboxylic acid methyl ester (7.68 g) was obtained as colorless crystals.

melting point: 174–175° C.

STARTING MATERIAL SYNTHETIC EXAMPLE 36

(R)-4-(benzyloxycarbonylamino)-1,1-dioxythiochromane-7-carboxylic acid

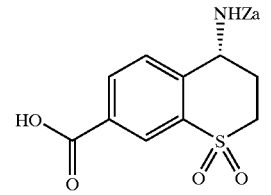

By a similar reaction operation as in Starting Material Synthetic Example 6 using (R)-4-(benzyloxycarbonylamino)-1,1-dioxythiochromane-7-carboxylic acid methyl ester (7.50 g) and potassium carbonate (5.33 g), the objective (R)-4-(benzyloxycarbonylamino)-

1,1-dioxythiochromane-7-carboxylic acid (6.54 g) was obtained as a colorless amorphous solid.

¹H-NMR(400 MHz, DMSO-d₆) δ=2.40–2.55(m, 2H), 3.68(br.s, 1H), 3.70–3.80(m, 1H), 5.11(s, 3H), 7.35–7.50(m, 5H), 7.55(br.s, 1H), 8.13(d, J=3 Hz, 1H), 8.23(s, 1H), 13.54(br.s, 1H).

STARTING MATERIAL SYNTHETIC EXAMPLE 37

(R)-4-(benzyloxycarbonylamino)thiochromane-7-carboxylic acid

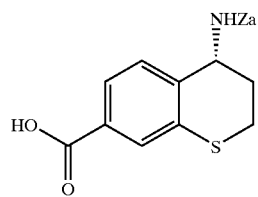

By a similar reaction operation as in Starting Material Synthetic Example 6 using (R)-4-(benzyloxycarbonylamino)thiochromane-7-carboxylic acid methyl ester (3.35 g) and potassium carbonate (2.59 g), the objective (R)-4-(benzyloxycarbonylamino)thiochromane-7-carboxylic acid (3.13 g) was obtained as colorless crystals.

¹H-NMR(400 MHz, DMSO-d₆) δ=1.95–2.15(m, 2H), 3.00–3.15(m, 2H), 4.81(br.q, J=6 Hz, 1H), 5.09(s, 2H), 7.30–7.40(m, 6H), 7.58(d, J=8 Hz, 1H), 7.60(s, 1H), 7.92(d, J=8.3 Hz, 1H), 13.02(s, 1H).

STARTING MATERIAL SYNTHETIC EXAMPLE 38

(R)-4-(benzyloxycarbonylamino)-1,1-dioxythiochromane-7-carboxylic acid

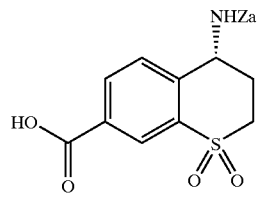

To an acetic acid (100 ml) solution of (R)-4-(benzyloxycarbonylamino)thiochromane-7-carboxylic acid (3.10 g) was added sodium peroxoborate 4 hydrate (4.01 g) at 50–60° C. and the mixture was stirred for 4 hr. Water (200 ml) was added to the reaction mixture and extracted with ethyl acetate. The obtained organic layer was washed with water and saturated brine and dried over anhydrous magnesium sulfate. The solvent was evaporated and recrystallized from ethyl acetate-hexane to give the objective (R)-4-(benzyloxycarbonylamino)-1,1-dioxythiochromane-7-carboxylic acid (3.56 g) as colorless crystals.

¹H-NMR(400 MHz, DMSO-d₆) δ=2.40–2.55(m, 2H), 3.68(br.s, 1H), 3.70–3.80(m, 1H), 5.11(br.s, 3H), 7.35–7.50 (m, 6H), 7.55(br.s, 1H), 8.13(d, J=8 Hz, 1H), 8.23(s, 1H), 13.54(br.s, 1H).

STARTING MATERIAL SYNTHETIC EXAMPLE 39

(R)-4-(benzyloxycarbonylamino)-1,1-dioxy-N-(4-pyridyl)thiochromane-7-carboxamide

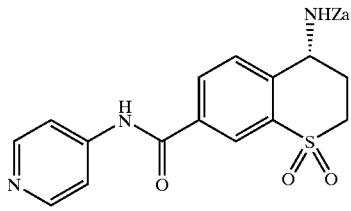

To an acetonitrile (200 ml) solution of (R)-4-(benzyloxycarbonylamino)-1,1-dioxythiochromane-7-carboxylic acid (3.00 g) and 4-aminopyridine (753 mg) were added triethylamine (3.23 g) and 2-chloro-1-methylpyridinium iodide (6.12 g). The mixture was stirred with heating under reflux for 1 hr, and the reaction system was cooled at room temperature. To the reaction mixture was added saturated aqueous sodium hydrogencarbonate solution (250 ml) and extracted with ethyl acetate. The obtained organic layer was washed with water and saturated brine and the obtained organic layer was dried over anhydrous magnesium sulfate. The solvent was concentrated under reduced pressure and the obtained residue was recrystallized from ethyl acetate-diisopropyl ether-hexane to give the objective (R)-4-(benzyloxycarbonylamino)-1,1-dioxy-N-(4-pyridyl)thiochromane-7-carboxamide (1.48 g) as pale-red crystals.

melting point: 211–213° C. (decomposition).

STARTING MATERIAL SYNTHETIC EXAMPLE 40

(R)-4-(benzyloxycarbonylamino)-1,1-dioxy-N-(4-pyridyl)thiochromane-7-carboxamide

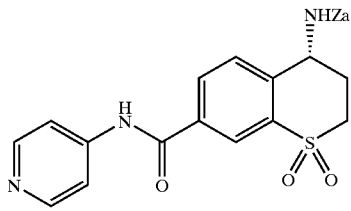

By a similar reaction operation as in Starting Material Synthetic Example 9 using (R)-4-(benzyloxycarbonylamino)-1,1-dioxythiochromane-7-carboxylic acid (3.25 g) and 4-aminopyridine (816 mg), the objective (R)-4-(benzyloxycarbonylamino)-1,1-dioxy-N-(4-pyridyl)thiochromane-7-carboxamide (2.87 g) was obtained as a pale-brown solid.

¹H-NMR(400 MHz, DMSO-d₆) δ=2.45–2.55(m, 2H), 3.65–3.85(m, 2H), 5.12(br.s, 3H), 7.30–7.40(m, 5H), 7.58(d, J=8 Hz, 1H), 7.80(d, J=7 Hz, 2H), 8.10–8.25(m, 2H), 8.43(s, 1H), 8.51(d, J=7 Hz, 2H), 10.87(s, 1H).

STARTING MATERIAL SYNTHETIC EXAMPLE 41

(R)-4-hydroxythiochromane-7-carboxylic acid methyl ester

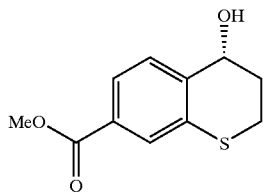

By a similar reaction operation as in Starting Material Synthetic Example 31 using (S)-5,5-diphenyl-2-methyl-3,4-propano-1,3,2-oxazaborolidine (997 mg), a borane-methyl sulfide complex (2.0 M toluene solution, 36.0 ml) and 4-oxythiochromane-7-carboxylic acid methyl ester (8.00 g), the objective (R)-4-hydroxythiochromane-7-carboxylic acid methyl ester (7.01 g) was obtained as colorless crystals.

melting point: 119–120° C.

$^1$H-NMR(400 MHz, DMSO-d$_6$) δ=1.95–2.10(m, 2H), 2.90–3.05(m, 1H), 3.10–3.20(m, 1H), 3.82(s, 3H), 4.63(q, J=4 Hz, 1H), 5.57(d, J=4 Hz, 1H), 7.50(d, J=8 Hz, 1H), 7.59(s, 1H), 7.60(d, J=8 Hz, 1H).

STARTING MATERIAL SYNTHETIC EXAMPLE 42

(S)-4-azidethiochromane-7-carboxylic acid methyl ester

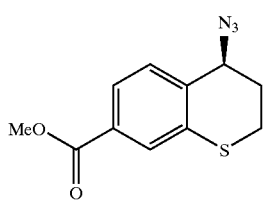

By a similar reaction operation as in Starting Material Synthetic Example 2 using (R)-4-hydroxythiochromane-7-carboxylic acid methyl ester (6.80 g), diphenyl phosphorazide (16.7 g) and 1,8-diazabicyclo[5.4.0]undecene (9.23 g), a crude product (9.26 g) of the objective (S)-4-azidethiochromane-7-carboxylic acid methyl ester was obtained as a pale yellow oil.

$^1$H-NMR(400 MHz, DMSO-d$_6$) δ=1.95–2.10(m, 1H), 2.25–2.35(m, 1H), 3.00–3.10(m, 1H), 3.10–3.25(m, 1H), 3.83(s, 3H), 5.04(t, J=4 Hz, 1H), 7.49(d, J=8 Hz, 1H), 7.66(d, J=8 Hz, 1H), 7.68(s, 1H).

STARTING MATERIAL SYNTHETIC EXAMPLE 43

(S)-4-aminothiochromane-7-carboxylic acid methyl ester

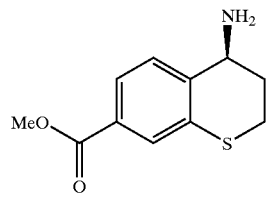

By a similar reaction operation as in Starting Material Synthetic Example 12 using a crude product (9.26 g) of (S)-4-azidethiochromane-7-carboxylic acid methyl ester and triphenylphosphine (11.9 g), the objective (S)-4-aminothiochromane-7-carboxylic acid methyl ester (3.96 g) was obtained as a pale yellow oil.

$^1$H-NMR(400 MHz, DMSO-d$_6$) δ=1.90–2.05(m, 2H) 2.90–3.00(m, 1H), 3.15–3.30(m, 1H), 3.81(s, 3H), 3.90(t, J=4 Hz, 1H), 7.50–7.65(m, 3H).

STARTING MATERIAL SYNTHETIC EXAMPLE 44

(S)-4-(benzyloxycarbonylamino)thiochromane-7-carboxylic acid methyl ester

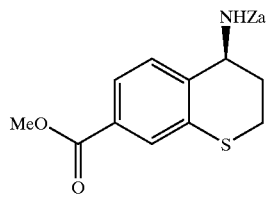

By a similar reaction operation as in Starting Material Synthetic Example 4 using (S)-4-aminothiochromane-7-carboxylic acid methyl ester (3.80 g) and benzyloxycarbonyl chloride (3.65 ml), the objective (S)-4-(benzyloxycarbonylamino)thiochromane-7-carboxylic acid methyl ester (5.02 g) was obtained as colorless crystals.

melting point: 140–141° C.

STARTING MATERIAL SYNTHETIC EXAMPLE 45

(S)-4-(benzyloxycarbonylamino)-1,1-dioxythiochromane-7-carboxylic acid methyl ester

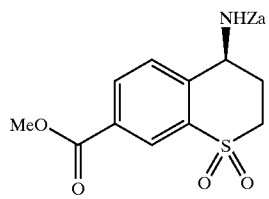

By a similar reaction operation as in Starting Material Synthetic Example 5 using (S)-4-(benzyloxycarbonylamino)thiochromane-7-carboxylic acid methyl ester (4.90 g) and 70% meta-chloroperbenzoic acid (10.2 g), the objective (S)-4-(benzyloxycarbonylamino)-1,1-dioxythiochromane-7-carboxylic acid methyl ester (5.03 g) was obtained as colorless crystals.

melting point: 174–175° C.

STARTING MATERIAL SYNTHETIC EXAMPLE 46

(S)-4-(benzyloxycarbonylamino)-1,1-dioxythiochromane-7-carboxylic acid

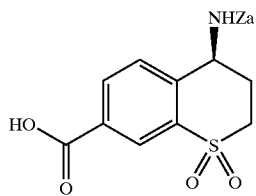

By a similar reaction operation as in Starting Material Synthetic Example 8 using (S)-4-(benzyloxycarbonylamino)-1,1-dioxythiochromane-7-carboxylic acid methyl ester (4.80 g) and 1N sodium hydroxide (24.6 ml), the objective (S)-4-(benzyloxycarbonylamino)-1,1-dioxythiochromane-7-carboxylic acid (4.16 g) was obtained as a colorless amorphous solid.

$^1$H-NMR(400 MHz, DMSO-$d_6$) δ=2.40–2.55(m, 2H), 3.68(br.s, 1H), 3.70–3.80(m, 1H), 5.11(s, 3H), 7.35–7.50(m, 5H), 7.55(br.s, 1H), 8.13(d, J=3 Hz, 1H), 8.23(s, 1H), 13.54(br.s, 1H).

STARTING MATERIAL SYNTHETIC EXAMPLE 47

(S)-4-(benzyloxycarbonylamino)thiochromane-7-carboxylic acid

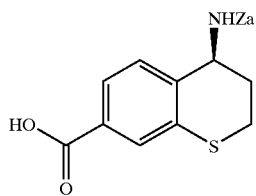

By a similar reaction operation as in Starting Material Synthetic Example 6 using (S)-4-(benzyloxycarbonylamino)thiochromane-7-carboxylic acid methyl ester (3.40 g) and potassium carbonate (2.63 g), the objective (S)-4-(benzyloxycarbonylamino)thiochromane-7-carboxylic acid (3.20 g) was obtained as colorless crystals.

$^1$H-NMR(400 MHz, DMSO-$d_6$) δ=1.95–2.15(m, 2H), 3.00–3.15(m, 2H), 4.81(br.q, J=6 Hz, 1H), 5.09(s, 2H), 7.30–7.40(m, 6H), 7.58(d, J=8 Hz, 1H), 7.60(s, 1H), 7.92(d, J=8 Hz, 1H), 13.02(s, 1H).

STARTING MATERIAL SYNTHETIC EXAMPLE 48

(S)-4-(benzyloxycarbonylamino)-1,1-dioxythiochromane-7-carboxylic acid

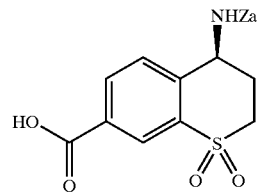

By a similar reaction operation as in Starting Material Synthetic Example 38 using (S)-4-(benzyloxycarbonylamino)thiochromane-7-carboxylic acid (2.20 g) and sodium peroxoborate 4 hydrate (2.93 g), the objective (S)-4-(benzyloxycarbonylamino)-1,1-dioxythiochromane-7-carboxylic acid (2.19 g) was obtained as a colorless amorphous solid.

$^1$H-NMR(400 MHz, DMSO-$d_6$) δ=2.40–2.55(m, 2H), 3.68(br.s, 1H), 3.70–3.80(m, 1H), 5.11(br.s, 3H), 7.35–7.50(m, 6H), 7.55(br.s, 1H), 8.13(d, J=3 Hz, 1H), 8.23(s, 1H), 13.54(br.s, 1H).

STARTING MATERIAL SYNTHETIC EXAMPLE 49

(S)-4-(benzyloxycarbonylamino)-1,1-dioxy-N-(4-pyridyl)thiochromane-7-carboxamide

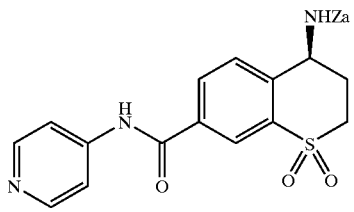

By a similar reaction operation as in Starting Material Synthetic Example 39 using (S)-4-(benzyloxycarbonylamino)-1,1-dioxythiochromane-7-carboxylic acid (1.60 g), 4-aminopyridine (402 mg), triethylamine (1.73 g) and 2-chloro-1-methylpyridinium iodide (3.27 g), the objective (S)-4-(benzyloxycarbonylamino)-1,1-dioxy-N-(4-pyridyl)thiochromane-7-carboxamide (712 mg) was obtained as pale-red crystals.

melting point: 211–213° C. (decomposition).

STARTING MATERIAL SYNTHETIC EXAMPLE 50

(S)-4-(benzyloxycarbonylamino)-1,1-dioxy-N-(4-pyridyl)thiochromane-7-carboxamide

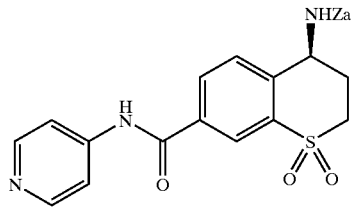

By a similar reaction operation as in Starting Material Synthetic Example 9 using (S)-4-(benzyloxycarbonylamino)-1,1-dioxythiochromane-7-carboxylic acid (2.10 g) and 4-aminopyridine (527 mg), the objective (S)-4-(benzyloxycarbonylamino)-1,1-dioxy-N-(4-pyridyl)thiochromane-7-carboxamide (1.05 g) was obtained as a pale-brown solid.

$^1$H-NMR(400 MHz, DMSO-d$_6$) δ=2.45–2.55(m, 2H), 3.65–3.85(m, 2H), 5.10–5.15(m, 3H), 7.30–7.40(m, 5H), 7.60(d, J=8 Hz, 1H), 7.80(d, J=7 Hz, 2H), 8.10–8.25(m, 2H), 8.43(s, 1H), 8.51(d, J=7 Hz, 2H), 10.87(s, 1H).

STARTING MATERIAL SYNTHETIC EXAMPLE 51

(S)-4-(tert-butoxycarbonylamino)thiochromane-7-carboxylic acid methyl ester

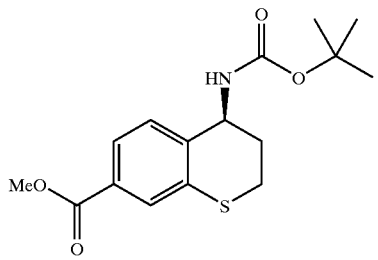

To a tetrahydrofuran (40 ml) solution of (S)-4-aminothiochromane-7-carboxylic acid methyl ester (4.50 g) was added an aqueous solution (20 ml) of potassium carbonate (3.35 g) at 0° C. To this mixed solution was added tetrahydrofuran solution (20 ml) of di-tert-butyldicarbonate (6.18 g) at the same temperature, and the mixture was stirred at room temperature for 4 hrs. Water (100 ml) was added to the reaction mixture and extracted with ethyl acetate. The obtained organic layer was washed with water and saturated brine and dried over anhydrous magnesium sulfate. The solvent in this solution was evaporated and recrystallized from ethyl acetate-hexane to give the objective (S)-4-(tert-butoxycarbonylamino)thiochromane-7-carboxylic acid methyl ester (6.11 g) as colorless crystals.

$^1$H-NMR(400 MHz, DMSO-d$_6$) δ=1.41(s, 9H), 2.00–2.10 (m, 2H), 3.09(t, J=6 Hz, 2H), 3.82(s, 3H), 4.70(br.s, 1H), 7.34(d, J=8 Hz, 1H), 7.48(d, J=8 Hz, 1H), 7.60(s, 2H).

STARTING MATERIAL SYNTHETIC EXAMPLE 52

(S)-4-(tert-butoxycarbonylamino)thiochromane-7-carboxylic acid

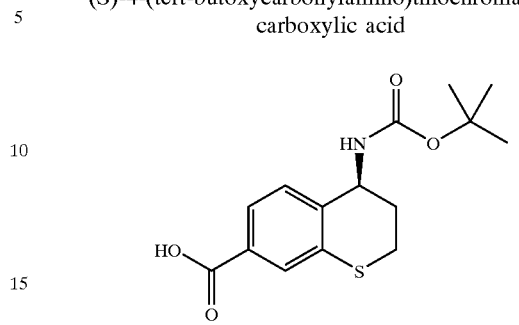

By a similar reaction operation as in Starting Material Synthetic Example 6 using (S)-4-(tert-butoxycarbonylamino)thiochromane-7-carboxylic acid methyl ester (5.75 g) and potassium carbonate (4.91 g), the objective (S)-4-(tert-butoxycarbonylamino)thiochromane-7-carboxylic acid (5.29 g) was obtained as colorless crystals.

$^1$H-NMR(400 MHz, DMSO-d$_6$) δ=1.42(s, 9H), 2.07(br.s, 2H), 3.09(t, J=6 Hz, 2H), 4.72(br.s, 1H), 7.32(d, J=8 Hz, 1H), 7.49(d, J=8 Hz, 1H), 7.59(s, 2H), 13.00(s, 1H).

STARTING MATERIAL SYNTHETIC EXAMPLE 53

(S)-4-(tert-butoxycarbonylamino)-N-(4-pyridyl)thiochromane-7-carboxamide

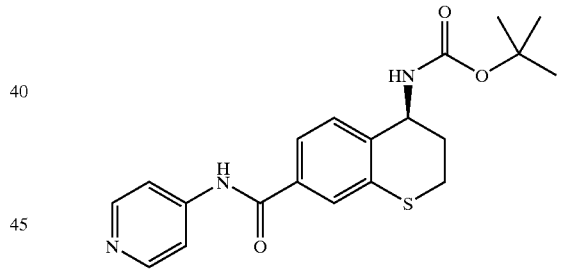

To an acetonitrile (75 ml) solution of (S)-4-(tert-butoxycarbonylamino)thiochromane-7-carboxylic acid (1.00 g) and 4-aminopyridine (335 mg) were added triethylamine (1.35 ml) and 2-chloro-1-methylpyridinium iodide (991 mg), and the mixture was stirred at room temperature overnight. Water was added to the reaction mixture and extracted with ethyl acetate. The obtained organic layer was washed with water and saturated brine and dried over anhydrous magnesium sulfate. The solvent of this solution was evaporated and purified by silica gel column chromatography (chloroform-methanol) to give the objective (S)-4-(tert-butoxycarbonylamino)-N-(4-pyridyl)thiochromane-7-carboxamide (845 mg) as pale yellow crystals.

$^1$H-NMR(400 MHz, DMSO-d$_6$) δ=1.42(s, 9H), 2.08(br.s, 2H), 3.11(br.s, 2H), 4.72(br.s, 1H), 7.35(d, J=8 Hz, 1H), 7.50(d, J=8 Hz, 1H), 7.62(d, J=8 Hz, 1H), 7.68(s, 1H), 7.76(d, J=5 Hz, 2H), 8.46(d, J=5 Hz, 2H), 10.51(s, 1H).

STARTING MATERIAL SYNTHETIC EXAMPLE 54

(S)-4-(tert-butoxycarbonylamino)-N-(1-triphenylmethylpyrazolo[3,4-b]pyridin-4-yl)thiochromane-7-carboxamide

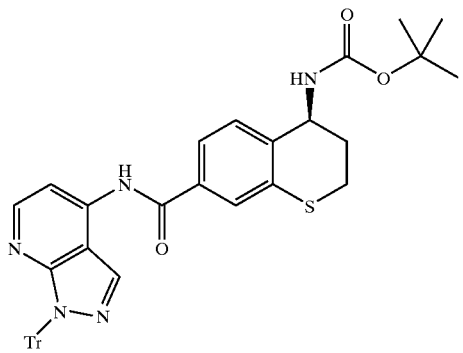

By a similar reaction operation as in Starting Material Synthetic Example 53 using (S)-4-(tert-butoxycarbonylamino)thiochromane-7-carboxylic acid (500 mg), 4-amino-1-triphenylmethylpyrazolo[3,4-b]pyridine (670 mg) synthesized according to a known method and 2-chloro-1-methylpyridinium iodide (496 mg), the objective (S)-4-(tert-butoxycarbonylamino)-N-(1-triphenylmethylpyrazolo[3,4-b]pyridin-4-yl)thiochromane-7-carboxamide (796 mg) was obtained as a pale yellow amorphous solid.

$^1$H-NMR(400 MHz, DMSO-$d_6$) δ=1.42(s, 9H), 2.06(br.s, 2H), 3.10(br.s, 2H), 4.70(br.s, 1H), 7.11(d, J=7 Hz, 6H), 7.30–7.55(m, 13H), 7.75(d, J=5 Hz, 1H), 8.53(d, J=5 Hz, 1H), 8.69(s, 1H), 10.72(s, 1H).

STARTING MATERIAL SYNTHETIC EXAMPLE 55

(S)-4-(tert-butoxycarbonylamino)-1,1-dioxythiochromane-7-carboxylic acid

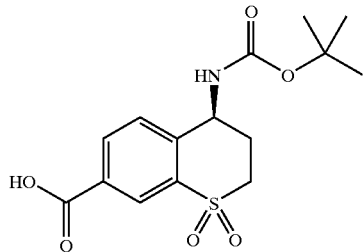

To an aqueous solution (25 ml) of 2KHSO$_5$·KHSO$_4$·K$_2$SO$_4$ (5.98 g) was added a saturated aqueous sodium hydrogencarbonate solution (25 ml) at 0° C., and an acetone solution (50 ml) of (S)-4-(tert-butoxycarbonylamino)thiochromane-7-carboxylic acid (1.00 g) was added dropwise at the same temperature. After the dropwise addition, and the mixture was stirred at room temperature for 4 hr, and 1N hydrochloric acid (100 ml) was added to complete the reaction. This reaction mixture was extracted with ethyl acetate and washed with water and saturated brine. The obtained organic layer was dried over magnesium sulfate and the solvent was evaporated under reduced pressure. The residue was recrystallized from ethyl acetate-hexane to give the objective (S)-4-(tert-butoxycarbonylamino)-1,1-dioxythiochromane-7-carboxylic acid (1.24 g) as colorless crystals.

$^1$H-NMR(400 MHz, DMSO-$d_6$) δ=1.44(s, 9H), 2.44(br.s, 2H), 3.50–3.80(m, 2H), 5.02(q, J=6 Hz, 1H), 7.52(d, J=8 Hz, 1H), 7.72(d, J=8 Hz, 1H), 8.15(d, J=8 Hz, 1H), 8.23(s, 1H), 13.55(br.s, 1H).

STARTING MATERIAL SYNTHETIC EXAMPLE 56

(S)-4-(tert-butoxycarbonylamino)-1,1-dioxy-N-(1-triphenylmethylpyrazolo[3,4-b]pyridin-4-yl)thiochromane-7-carboxamide

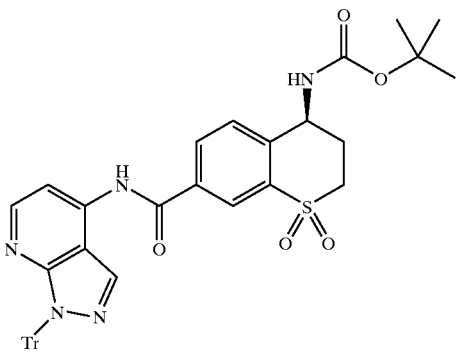

By a similar reaction operation as in Starting Material Synthetic Example 53 using (S)-4-(tert-butoxycarbonylamino)-1,1-dioxythiochromane-7-carboxylic acid (500 mg), 4-amino-1-triphenylmethylpyrazolo[3,4-b]pyridine (608 mg) and 2-chloro-1-methylpyridinium iodide (450 mg), the objective (S)-4-(tert-butoxycarbonylamino)-1,1-dioxy-N-(1-triphenylmethylpyrazolo-[3,4-b]pyridin-4-yl)thiochromane-7-carboxamide (633 mg) was obtained as a pale yellow amorphous solid.

$^1$H-NMR(400 MHz, DMSO-$d_6$) δ=1.44(s, 9H), 2.47(br.s, 2H), 3.71(br.s, 2H), 5.00(br.s, 1H), 7.13(d, J=7 Hz, 6H), 7.35–7.40(m, 9H), 7.52(d, J=7 Hz, 1H), 7.75(d, J=5 Hz, 1H), 7.76(d, J=10 Hz, 1H), 8.11(d, J=7 Hz, 1H), 8.23(s, 1H), 8.57(d, J=5 Hz, 1H), 8.66(s, 1H), 11.01(s, 1H).

STARTING MATERIAL SYNTHETIC EXAMPLE 57

4-azide-1H-pyrrolo[2,3-b]pyridine

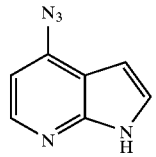

To an N,N-dimethylformamide (150 ml) solution of 4-chloro-1H-pyrrolo[2,3-b]pyridine (16.0 g) obtained by a known method were added sodium azide (10.2 g) and ammonium chloride (8.40 g), and the mixture was stirred at 100° C. for 8 hr. The reaction mixture was allowed to cool to room temperature and water (300 ml) was added and extracted with ethyl acetate. The organic layer was washed with water and saturated brine and dried over anhydrous magnesium sulfate. The solvent was evaporated to give the objective 4-azide-1H-pyrrolo[2,3-b]pyridine (11.3 g) as a brown solid.

¹H-NMR(400 MHz, DMSO-d₆) δ=6.45(d, J=3 Hz, 1H), 6.88(d, J=5 Hz, 1H), 7.45(d, J=4 Hz, 1H), 8.17(d, J=5 Hz, 1H), 11.85(s, 1H).

STARTING MATERIAL SYNTHETIC EXAMPLE 58

4-amino-1-[2-(trimethylsilyl)ethoxymethyl]pyrrolo[2,3-b]pyridine

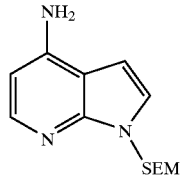

To an N,N-dimethylformamide (75 ml) solution of 4-azide-1H-pyrrolo[2,3-b]pyridine (10.0 g) were added diisopropylethylamine (16.4 ml) and 2-(trimethylsilyl)ethoxymethyl chloride (12.6 g) at 0° C., and the mixture was stirred at room temperature for 5 hr. Then water (300 ml) was added to the reaction mixture and the mixture was extracted with ethyl acetate. The obtained organic layer was washed with water and saturated brine and dried over anhydrous magnesium sulfate. The solvent was evaporated to give a crude product (18.2 g) of 4-azide-1-[2-(trimethylsilyl)-ethoxymethyl]pyrrolo[2,3-b]pyridine.

The obtained crude product of 4-azide-1-[2-(trimethylsilyl)ethoxymethyl]pyrrolo[2,3-b]pyridine was dissolved in isopropyl alcohol (150 ml), and sodium borohydride (2.35 g) was slowly added at room temperature. The reaction mixture was stirred at room temperature for 6 hr and water (200 ml) was added. The mixture was extracted with ethyl acetate and the obtained organic layer was washed with water and saturated brine and dried over anhydrous sodium sulfate. The solvent was evaporated and the residue was purified by silica gel column chromatography and recrystallized from ethyl acetate-hexane to give the objective 4-amino-1-[2-(trimethylsilyl)ethoxymethyl]pyrrolo[2,3-b]pyridine (12.2 g) as pale-brown crystals.

¹H-NMR(400 MHz, DMSO-d₆) δ=−0.09(s, 9H), 0.81(t, J=8 Hz, 2H), 3.47(t, J=8 Hz, 2H), 5.48(s, 2H), 6.19(d, J=5 Hz, 1H), 6.20(s, 2H), 6.56(d, J=4 Hz, 1H), 7.19(d, J=4 Hz,), 7.76(d, J=5 Hz, 1H).

STARTING MATERIAL SYNTHETIC EXAMPLE 59

(S)-4-(benzyloxycarbonylamino)-N-{1-[2-(trimethylsilyl)ethoxymethyl]-pyrrolo[2,3-b]pyridin-4-yl}thiochromane-7-carboxamide

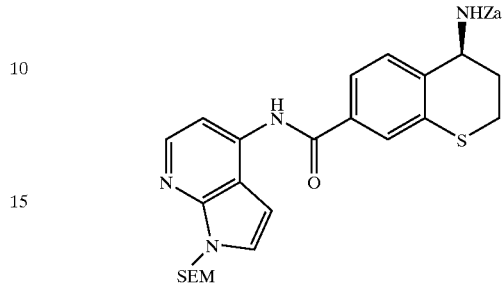

To a tetrahydrofuran solution of 4-amino-1-[2-(trimethylsilyl)ethoxymethyl]pyrrolo[2,3-b]pyridine (1.32 g) was added dropwise n-butyllithium (1.59 M, 3.17 ml) and the mixture was stirred at the same temperature for 15 min. To this solution was added dropwise a tetrahydrofuran solution (20 ml) of (S)-4-(benzyloxycarbonylamino)thiochromane-7-carboxylic acid chloride (4.20 mmol) obtained by a similar reaction step as in Starting Material Synthetic Example 9 at 0° C. The reaction mixture was stirred at room temperature for 5 hr. Water (100 ml) was added and the mixture was extracted with ethyl acetate. The obtained organic layer was washed with water and saturated brine and dried over anhydrous magnesium sulfate. The solvent was evaporated and purified by silica gel column chromatography (hexane-ethyl acetate) to give the objective (S)-4-(benzyloxycarbonylamino)-N-{1-[2-(trimethylsilyl)ethoxymethyl]pyrrolo[2,3-b]pyridin-4-yl}thiochromane-7-carboxamide (1.06 g) as a pale-brown amorphous solid.

¹H-NMR(400 MHz, DMSO-d₆) δ=−0.09(s, 9H), 0.81(t, J=7 Hz, 2H), 2.13(br.s, 2H), 3.14(br.s, 2H), 3.51(t, J=7 Hz, 2H), 4.83(br.s, 1H), 5.11(s, 2H), 5.62(s, 2H), 6.84(s, 1H), 7.35–7.45(m, 6H), 7.54(br.s, 1H), 7.60–7.75(m, 3H), 7.96(d, J=8 Hz, 1H), 8.21(d, J=5 Hz, 1H), 10.42(s, 1H).

STARTING MATERIAL SYNTHETIC EXAMPLE 60

(S)-4-(benzyloxycarbonylamino)-N-(1H-pyrrolo[2,3-b]pyridin-4-yl)thiochromane-7-carboxamide

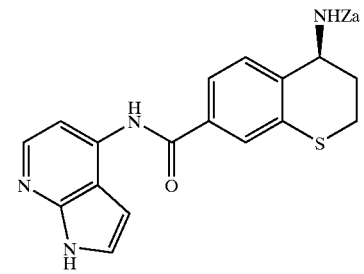

To (S)-4-(benzyloxycarbonylamino)-N-{1-[2-(trimethylsilyl)ethoxymethyl]pyrrolo[2,3-b]pyridin-4-yl}thiochromane-7-carboxamide (1.02 g) was added a 4N hydrochloric acid dioxane solution (30 ml) and the mixture was stirred at room temperature for 6 hr. Water (100 ml) was added to the reaction mixture and potassium carbonate was added until the reaction mixture shows alkalinity. This suspension was stood still at 0° C. for 30 min and the precipitated crystals were collected by filtration to give a crude product (766 mg) of (S)-4-(benzyloxycarbonylamino)-N-(1-hydroxymethylpyrrolo-[2,3-b]pyridin-4-yl)thiochromane-7-carboxamide.

The obtained (S)-4-(benzyloxycarbonylamino)-N-(1-hydroxymethylpyrrolo[2,3-b]pyridin-4-yl)thiochromane-7-carboxamide (766 mg) was dissolved in methanol (10 ml) and tetrahydrofuran (20 ml), and an aqueous solution (30 ml) of sodium acetate (5.00 g) was added. The reaction mixture was stirred under reflux for 5 hr and allowed to return to room temperature. Water (100 ml) was added and the precipitated crystals were collected by filtration to give the objective (S)-4-(benzyloxycarbonylamino)-N-(1H-pyrrolo[2,3-b]pyridin-4-yl)thiochromane-7-carboxamide (504 mg) as a pale yellow solid.

$^1$H-NMR(400 MHz, DMSO-$d_6$) δ=2.23(br.q, J=6 Hz, 2H), 3.20–3.30(m, 2H), 4.93(br.q, J=6 Hz, 1H), 5.20(s, 2H), 6.84(s, 1H), 7.35–7.55(m, 7H), 7.71(d, J=5 Hz, 1H), 7.73(d, J=9 Hz, 1H), 7.80(s, 1H), 8.05(d, J=8 Hz, 1H), 8.24(d, J=5 Hz, 1H), 10.43(s, 1H), 11.69(br.s, 1H).

STARTING MATERIAL SYNTHETIC EXAMPLE 61

(S)-4-(benzyloxycarbonylamino)-1,1-dioxy-N-{1-[2-(trimethylsilyl)-ethoxymethyl]pyrrolo[2,3-b]pyridin-4-yl}thiochromane-7-carboxamide

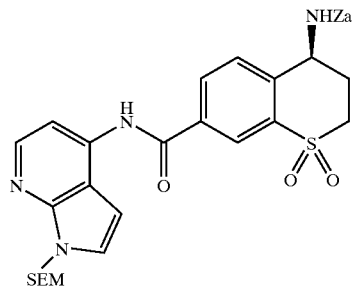

By a similar reaction operation as in Starting Material Synthetic Example 9 using 4-amino-1-[2-(trimethylsilyl)-ethoxymethyl]pyrrolo[2,3-b]pyridine (762 mg) and (S)-4-(benzyloxycarbonylamino)-1,1-dioxythiochromane-7-carboxylic acid (1.09 g), the objective (S)-4-(benzyloxycarbonylamino)-1,1-dioxy-N-{1-[2-(trimethylsilyl)ethoxymethyl]pyrrolo[2,3-b]pyridin-4-yl}thiochromane-7-carboxamide (840 mg) was obtained as a pale yellow amorphous solid.

$^1$H-NMR(400 MHz, DMSO-$d_6$) δ=−0.09(s, 9H), 0.83(t, J=7 Hz, 2H), 2.40–2.50(m, 2H), 3.52(t, J=7 Hz, 2H), 3.60–3.85(m, 2H), 5.14(s, 3H), 5.63(s, 2H), 6.81(s, 1H), 7.35–7.45(m, 5H), 7.50–7.65(m, 2H), 7.67(d, J=4 Hz, 1H), 8.15–8.25(m, 3H), 8.41(s, 1H), 10.79(s, 1H).

STARTING MATERIAL SYNTHETIC EXAMPLE 62

(S)-4-(benzyloxycarbonylamino)-1,1-dioxy-N-(1H-pyrrolo[2,3-b]pyridin-4-yl)thiochromane-7-carboxamide

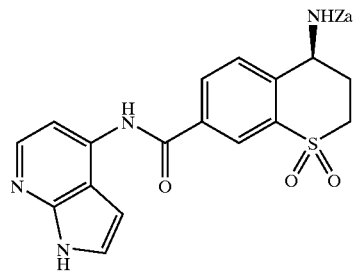

By a similar reaction operation as in Starting Material Synthetic Example 60 using (S)-4-(benzyloxycarbonylamino)-1,1-dioxy-N-{1-[2-(trimethylsilyl)ethoxymethyl]pyrrolo[2,3-b]pyridin-4-yl}thiochromane-7-carboxamide (835 mg), 4N hydrochloric acid dioxane (20 ml) and sodium acetate (5.00 g), the objective (S)-4-(benzyloxycarbonylamino)-1,1-dioxy-N-(1H-pyrrolo[2,3-b]pyridin-4-yl)thiochromane-7-carboxamide (513 mg) was obtained as a pale yellow amorphous solid.

$^1$H-NMR(400 MHz, DMSO-$d_6$) δ=2.45–2.55(m, 2H), 3.60–3.75(m, 2H), 5.13(s, 3H), 6.72(s, 1H), 7.30–7.50(m, 6H), 7.59(d, J=7 Hz, 2H), 8.10–8.25(m, 3H), 8.39(s, 1H), 10.72(s, 1H), 11.64(s, 1H).

STARTING MATERIAL SYNTHETIC EXAMPLE 63

4-hydroxy-8-methylthiochromane-7-carboxylic acid methyl ester

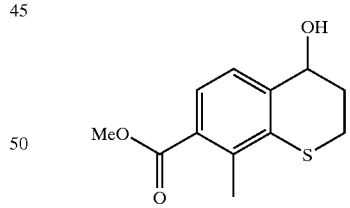

By a similar reaction operation as in Starting Material Synthetic Example 1 using 8-methyl-4-oxythiochromane-7-carboxylic acid methyl ester (3.00 g) synthesized according to a known method (Ger. Offen. DE 19532312 A16 WO 9709327 A1) and sodium borohydride (480 mg), the objective 4-hydroxy-8-methylthiochromane-7-carboxylic acid methyl ester (3.02 g) was obtained as pale yellow crystals.

$^1$H-NMR(400 MHz, DMSO-$d_6$) δ=1.90–2.10(m, 2H), 2.34(s, 3H), 2.95–3.05(m, 1H), 3.10–3.20(m, 1H), 3.81(s, 3H), 4.62(br.s, 1H), 5.51(d, J=5 Hz, 1H), 7.33(d, J=8 Hz, 1H), 7.40(d, J=8 Hz, 1H).

STARTING MATERIAL SYNTHETIC EXAMPLE 64

4-azide-8-methylthiochromane-7-carboxylic acid methyl ester

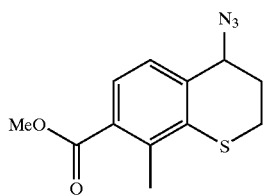

By a similar reaction operation as in Starting Material Synthetic Example 2 using 4-hydroxy-8-methylthiochromane-7-carboxylic acid methyl ester (3.00 g), diphenylphosphoryl azide (6.93 g) and 1,8-diazabicyclo[5.4.0]undecene (3.83 g), a crude product (3.35 g) of the objective 4-azide-8-methylthiochromane-7-carboxylic acid methyl ester was obtained as a pale yellow oil.

$^1$H-NMR(400 MHz, DMSO-d$_6$) δ=1.85–2.00(m, 1H), 2.20–2.30(m, 1H), 2.33(s, 3H), 3.00–3.20(m, 2H), 3.82(s, 3H), 5.03(br.s, 1H), 7.29(d, J=8 Hz, 1H), 7.43(d, J=8 Hz, 1H).

STARTING MATERIAL SYNTHETIC EXAMPLE 65

4-amino-8-methylthiochromane-7-carboxylic acid methyl ester

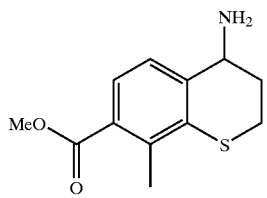

By a similar reaction operation as in Starting Material Synthetic Example 12 using a crude product (3.35 g) of 4-azide-8-methylthiochromane-7-carboxylic acid methyl ester and triphenylphosphine (4.95 g), the objective 4-amino-8-methylthiochromane-7-carboxylic acid methyl ester (2.60 g) was obtained as a yellow oil.

$^1$H-NMR(400 MHz, DMSO-d$_6$) δ=1.85–2.00(m, 2H), 2.33(s, 3H), 2.90–3.00(m, 1H), 3.15–3.25(m, 1H), 3.79(s, 3H), 3.90(t, J=5 Hz, 1H), 7.33(d, J=8 Hz, 1H), 7.37(d, J=8 Hz, 1H).

STARTING MATERIAL SYNTHETIC EXAMPLE 66

4-(tert-butoxycarbonylamino)-8-methylthiochromane-7-carboxylic acid methyl ester

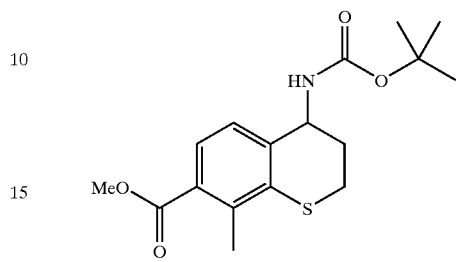

By a similar reaction operation as in Starting Material Synthetic Example 51 using 4-amino-8-methylthiochromane-7-carboxylic acid methyl ester (2.60 g), potassium carbonate (1.80 g) and di-tert-butyldicarbonate (3.36 g), the objective 4-(tert-butoxycarbonylamino)-8-methylthiochromane-7-carboxylic acid methyl ester (2.73 g) was obtained as colorless crystals.

$^1$H-NMR(400 MHz, DMSO-d$_6$) δ=1.42(s, 9H), 2.02(br.s, 2H), 2.34(s, 3H), 3.08(br.t, J=7 Hz, 2H), 3.81(s, 3H), 4.70(br.s, 1H), 7.17(d, J=8 Hz, 1H), 7.40(d, J=8 Hz, 1H), 7.47(d, J=8 Hz, 1H).

STARTING MATERIAL SYNTHETIC EXAMPLE 67

4-(tert-butoxycarbonylamino)-8-methylthiochromane-7-carboxylic acid

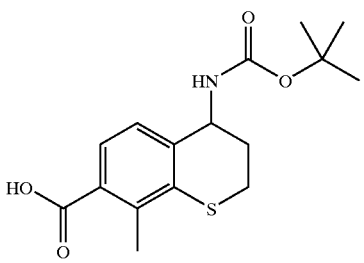

By a similar re action operation as in Starting Material Synthetic Example 6 using 4-(tert-butoxycarbonylamino)-8-methylthiochromane-7-carboxylic acid methyl ester (2.70 g) and potassium carbonate (4.42 g), the objective 4-(tert-butoxycarbonylamino)-8-methylthiochromane-7-carboxylic acid (1.80 g) was obtained as colorless crystals.

$^1$H-NMR(400 MHz, DMSO-d$_6$) δ=1.42(s, 9H), 2.02(br.s, 2H), 2.37(s, 3H), 3.07(br.s, 2H), 4.70(br.s, 1H), 7.15(d, J=8 Hz, 1H), 7.35–7.50(m, 2H), 12.91(s, 1H).

STARTING MATERIAL SYNTHETIC EXAMPLE 68

4-(tert-butoxycarbonylamino)-8-methyl-N-(4-pyridyl)thiochromane-7-carboxamide

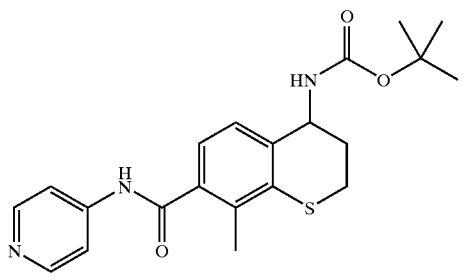

By a similar reaction operation as in Starting Material Synthetic Example 53 using 4-(tert-butoxycarbonylamino)-8-methylthiochromane-7-carboxylic acid (400 mg), 4-aminopyridine (91.9 mg) and 2-chloro-1-methylpyridinium iodide (474 mg), the objective 4-(tert-butoxycarbonylamino)-8-methyl-N-(4-pyridyl)thiochromane-7-carboxamide (1.80 g) was obtained as colorless crystals.

$^1$H-NMR(400 MHz, DMSO-$d_6$) δ=1.42(s, 9H), 2.03(br.s, 2H), 2.19(s, 3H), 3.10(br.s, 2H), 4.71(br.s, 1H), 7.15–7.20 (m, 2H), 7.45(d, J=8 Hz, 1H), 7.67(d, J=6 Hz, 2H), 8.45(d, J=6 Hz, 2H), 10.69(s, 1H).

STARTING MATERIAL SYNTHETIC EXAMPLE 69

(R)-4-hydroxy-8-methylthiochromane-7-carboxylic acid methyl ester

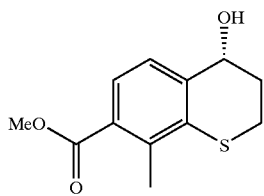

By a similar reaction operation as in Starting Material Synthetic Example 31 using 8-methyl-4-oxythiochromane-7-carboxylic acid methyl ester (22.0 g), (S)-5,5-diphenyl-2-methyl-3,4-propano-1,3,2-oxazaborolidine (1.0 M toluene solution, 9.32 ml) and borane-methyl sulfide complex (2.0 M toluene solution, 93.2 ml), the objective (R)-4-hydroxy-8-methylthiochromane-7-carboxylic acid methyl ester (20.7 g) was obtained as colorless crystals.

$^1$H-NMR(400 MHz, DMSO-$d_6$) δ=1.90–2.10(m, 2H), 2.34(s, 3H), 2.95–3.05(m, 1H), 3.10–3.20(m, 1H), 3.81(s, 3H), 4.62(br.s, 1H), 5.51(d, J=5 Hz, 1H), 7.33(d, J=8 Hz, 1H), 7.40(d, J=8 Hz, 1H).

STARTING MATERIAL SYNTHETIC EXAMPLE 70

(S)-4-azide-8-methylthiochromane-7-carboxylic acid methyl ester

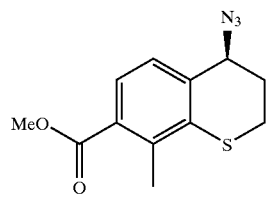

By a similar reaction operation as in Starting Material Synthetic Example 2 using (R)-4-hydroxy-8-methylthiochromane-7-carboxylic acid methyl ester (5.00 g), diphenylphosphoryl azide (11.6 g) and 1,8-diazabicyclo[5.4.0]undecene (6.41 g), a crude product (7.81 g) of the objective (S)-4-azide-8-methylthiochromane-7-carboxylic acid methyl ester was obtained as a pale yellow oil.

$^1$H-NMR(400 MHz, DMSO-$d_6$) δ=1.85–2.00(m, 1H), 2.20–2.30(m, 1H), 2.33(s, 3H), 3.00–3.20(m, 2H), -3.82(s, 3H), 5.03(br.s, 1H), 7.29(d, J=8 Hz, 1H), 7.43(d, J=8 Hz, 1H).

STARTING MATERIAL SYNTHETIC EXAMPLE 71

(S)-4-amino-8-methylthiochromane-7-carboxylic acid methyl ester

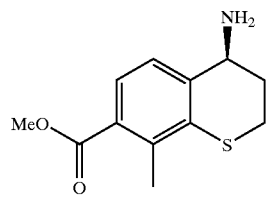

By a similar reaction operation as in Starting Material Synthetic Example 12 using a crude product (7.81 g) of (S)-4-azide-8-methylthiochromane-7-carboxylic acid methyl ester and triphenylphosphine (8.25 g), the objective (S)-4-amino-8-methylthiochromane-7-carboxylic acid methyl ester (4.53 g) was obtained as a yellow oil.

$^1$H-NMR(400 MHz, DMSO-$d_6$) δ=1.85–2.00(m, 2H), 2.33(s, 3H), 2.90–3.00(m, 1H), 3.15–3.25(m, 1H), 3.79(s, 3H), 3.90(t, J=5 Hz, 1H), 7.33(d, J=8 Hz, 1H), 7.37(d, J=8 Hz, 1H).

STARTING MATERIAL SYNTHETIC EXAMPLE 72

(S)-4-(tert-butoxycarbonylamino)-8-methylthiochromane-7-carboxylic acid methyl ester

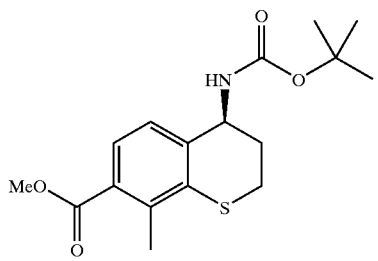

By a similar reaction operation as in Starting Material Synthetic Example 51 using (S)-4-amino-8-methylthiochromane-7-carboxylic acid methyl ester (4.50 g), potassium carbonate (3.14 g) and di-tert-butyldicarbonate (5.80 g), the objective (S)-4-(tert-butoxycarbonylamino)-8-methylthiochromane-7-carboxylic acid methyl ester (5.04 g) was obtained as colorless crystals.

$^1$H-NMR(400 MHz, DMSO-d$_6$) δ=1.42(s, 9H), 2.02(br.s, 2H), 2.34(s, 3H), 3.08(br.t, J=7 Hz, 2H), 3.81(s, 3H), 4.70 (br.s, 1H), 7.17(d, J=8 Hz, 1H), 7.40(d, J=8 Hz, 1H), 7.47(d, J=8 Hz, 1H).

STARTING MATERIAL SYNTHETIC EXAMPLE 73

(S)-4-(tert-butoxycarbonylamino)-8-methylthiochromane-7-carboxylic acid

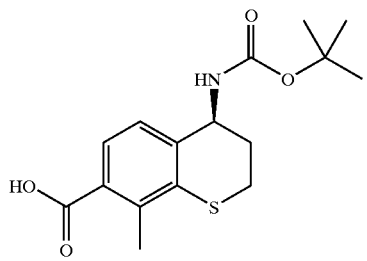

By a similar reaction operation as in Starting Material Synthetic Example 6 using (S)-4-(tert-butoxycarbonylamino)-8-methylthiochromane-7-carboxylic acid methyl ester (5.00 g) and potassium carbonate (6.13 g), the objective (S)-4-(tert-butoxycarbonylamino)-8-methylthiochromane-7-carboxylic acid (4.06 g) was obtained as a colorless amorphous solid.

$^1$H-NMR(400 MHz, DMSO-d$_6$) δ=1.42(s, 9H), 2.02(br.s, 2H), 2.37(s, 3H), 3.07(br.s, 2H), 4.70(br.s, 1H), 7.15(d, J=8 Hz, 1H), 7.35–7.50(m, 2H), 12.91(s, 1H).

STARTING MATERIAL SYNTHETIC EXAMPLE 74

(S)-4-(tert-butoxycarbonylamino)-8-methyl-N-(4-pyridyl)thiochromane-7-carboxamide

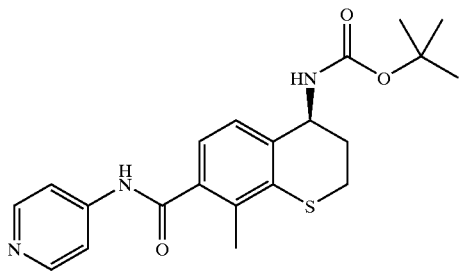

By a similar reaction operation as in Starting Material Synthetic Example 53 using (S)-4-(tert-butoxycarbonylamino)-8-methylthiochromane-7-carboxylic acid (2.00 g), 4-aminopyridine (582 mg) and 2-chloro-1-methylpyridinium iodide (2.37 g), the objective (S)-4-(tert-butoxycarbonylamino)-8-methyl-N-(4-pyridyl) thiochromane-7-carboxamide (1.86 g) was obtained as colorless crystals.

$^1$H-NMR(400 MHz, DMSO-d$_6$) δ=1.43(s, 9H), 2.04(br.s, 2H), 2.21(s, 3H), 3.11(br.s, 2H), 4.72(br.s, 1H), 7.15–7.20 (m, 2H), 7.47(d, J=8 Hz, 1H), 7.69(d, J=6 Hz, 2H), 8.46(d, J=6 Hz, 2H), 10.71(s, 1H).

STARTING MATERIAL SYNTHETIC EXAMPLE 75

(S)-4-(tert-butoxycarbonylamino)-8-methyl-1,1-dioxythiochromane-7-carboxylic acid

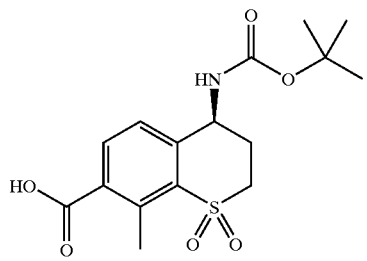

By a similar reaction operation as in Starting Material Synthetic Example 55 using (S)-4-(tert-butoxycarbonylamino)-8-methylthiochromane-7-carboxylic acid (2.00 g) and 2KHSO$_5$.KHSO$_4$.K$_2$SO$_4$ (11.4 g), the objective (S)-4-(tert-butoxycarbonylamino)-8-methyl 1,1-dioxythiochromane-7-carboxylic acid (2.27 g) was obtained as colorless crystals.

$^1$H-NMR(400 MHz, DMSO-d$_6$) δ=1.43(s, 9H), 2.35(br.s, 2H), 2.75(s, 3H), 3.67(br.s, 2H), 4.92(br.q, J=6 Hz, 1H), 7.31(d, J=8 Hz, 1H), 7.71(d, J=9 Hz, 1H), 7.83(d, J=8 Hz, 1H), 13.40(br.s, 1H).

STARTING MATERIAL SYNTHETIC EXAMPLE 76

(S)-4-(tert-butoxycarbonylamino)-8-methyl-1,1-dioxy-N-(4-pyridyl)thiochromane-7-carboxamide

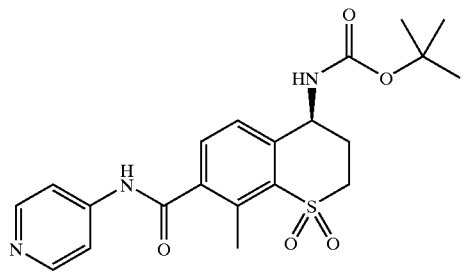

By a similar reaction operation as in Starting Material Synthetic Example 53 using (S)-4-(tert-butoxycarbonylamino)-8-methyl-1,1-dioxythiochromane-7-carboxylic acid (1.50 g), 4-aminopyridine (398 mg) and 2-chloro-1-methylpyridinium iodide (1.40 g), the objective (S)-4-(tert-butoxycarbonylamino)-8-methyl-1,1-dioxy-N-(4-pyridyl)thiochromane-7-carboxamide (735 mg) was obtained as colorless crystals.

$^1$H-NMR(400 MHz, DMSO-$d_6$) δ=1.44(s, 9H), 2.37(br.s, 2H), 2.67(s, 3H), 3.65–3.75(m, 2H), 4.96(br.q, J=6 Hz, 1H), 7.34(d, J=8 Hz, 1H), 7.65–7.70(m, 3H), 7.77(d, J=9 Hz, 1H), 8.49(d, J=6 Hz, 1H), 10.90(s, 1H).

STARTING MATERIAL SYNTHETIC EXAMPLE 77

(S)-4-(tert-butoxycarbonylamino)-8-methyl-1,1-dioxy-N-(1-triphenylmethylpyrazolo[3,4-b]pyridin-4-yl)thiochromane-7-carboxamide

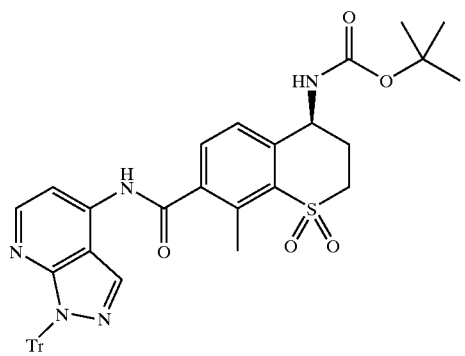

By a similar reaction operation as in Starting Material Synthetic Example 53 using (S)-4-(tert-butoxycarbonylamino)-8-methyl-1,1-dioxythiochromane-7-carboxylic acid (100 mg), 4-amino-1-triphenylmethylpyrazolo[3,4-b]pyridine (106 mg) and 2-chloro-1-methylpyridinium iodide (89.9 mg), the objective (S)-4-(tert-butoxycarbonylamino)-8-methyl-1,1-dioxy-N-(1-triphenylmethylpyrazolo[3,4-b]pyridin-4-yl)thiochromane-7-carboxamide (145 mg) was obtained as a pale yellow amorphous solid.

$^1$H-NMR(400 MHz, DMSO-$d_6$) δ=1.42(s, 9H), 2.34(br.s, 2H), 2.59(s, 3H), 3.68(br.s, 2H), 4.91(br.s, 1H), 7.09(d, J=6 Hz, 6H), 7.30(d, J=8 Hz, 1H), 7.33–7.40(m, 9H), 7.63(d, J=8 Hz, 1H), 7.73(d, J=8 Hz, 1H), 7.95(d, J=4 Hz, 1H), 8.54(d, J=5 Hz, 1H), 8.63(s, 1H), 11.07(s, 1H).

STARTING MATERIAL SYNTHETIC EXAMPLE 78

4-hydroxy-6-methylthiochromane-7-carboxylic acid methyl ester

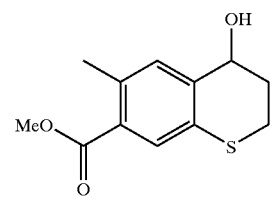

By a similar reaction operation as in Starting Material Synthetic Example 1 using 6-methyl-4-oxythiochromane-7-carboxylic acid methyl ester (3.00 g) synthesized according to a known method and sodium borohydride (480 mg), the objective 4-hydroxy-6-methyl-thiochromane-7-carboxylic acid methyl ester (3.03 g) was obtained as pale yellow crystals.

$^1$H-NMR(400 MHz, CDCl$_3$) δ=2.05–2.15(m, 2H), 2.30–2.40(m, 1H), 2.53(s, 3H), 2.85–2.95(m, 1H), 3.25–3.35(m, 1H), 3.88(s, 3H), 4.79(br.s, 1H), 7.24(s, 1H), 7.71(s, 1H).

STARTING MATERIAL SYNTHETIC EXAMPLE 79

4-azide-6-methylthiochromane-7-carboxylic acid methyl ester

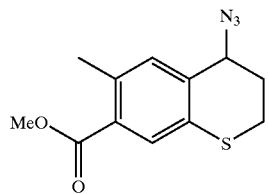

By a similar reaction operation as in Starting Material Synthetic Example 2 using 4-hydroxy-6-methylthiochromane-7-carboxylic acid methyl ester (3.00 g), diphenylphosphoryl azide (6.93 g) and 1,8-diazabicyclo[5.4.0]undecene (3.83 g), a crude product (5.05 g) of the objective 4-azide-6-methylthiochromane-7-carboxylic acid methyl ester was obtained as a pale yellow oil.

$^1$H-NMR(400 MHz, CDCl$_3$) δ=2.00–2.15(m, 1H), 2.30–2.35(m, 1H), 2.52(s, 3H), 2.80–2.90(m, 1H), 3.25–3.35(m, 1H), 3.86(s, 3H), 4.60(br.s, 1H), 7.07(s, 1H), 7.71(s, 1H).

STARTING MATERIAL SYNTHETIC EXAMPLE 80

4-amino-6-methylthiochromane-7-carboxylic acid methyl ester

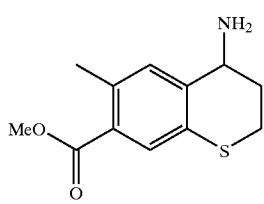

By a similar reaction operation as in Starting Material Synthetic Example 12 using a crude product (5.05 g) of 4-azide-6-methylthiochromane-7-carboxylic acid methyl ester and triphenylphosphine (4.95 g), the objective 4-amino-6-methylthiochromane-7-carboxylic acid methyl ester (2.26 g) was obtained as a yellow oil.

$^1$H-NMR(400 MHz, CDCl$_3$) δ=1.51(s, 2H), 2.05–2.15(m, 2H), 2.50(s, 3H), 2.90–3.00(m, 1H), 3.15–3.25.(m, 1H), 3.84(s, 3H), 4.00(t, J=4 Hz, 1H), 7.17(s, 1H), 7.68(s, 1H).

STARTING MATERIAL SYNTHETIC EXAMPLE 81

4-(tert-butoxycarbonylamino)-6-methylthiochromane-7-carboxylic acid methyl ester

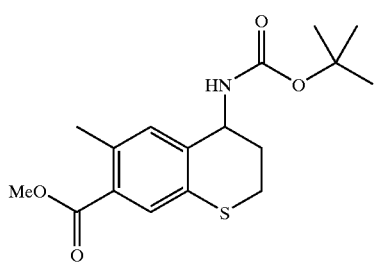

By a similar reaction operation as in Starting Material Synthetic Example 51 using 4-amino-6-methylthiochromane-7-carboxylic acid methyl ester (2.25 g), potassium carbonate (1.57 g) and di-tert-butyldicarbonate (2.90 g), the objective 4-(tert-butoxycarbonylamino)-6-methylthiochromane-7-carboxylic acid methyl ester (2.86 g) was obtained as colorless crystals.

$^1$H-NMR(400 MHz, DMSO-d$_6$) δ=1.43(s, 9H), 2.05(br.t, J=6 Hz, 2H), 2.41(s, 3H), 3.07(t, J=6 Hz, 2H), 3.80(s, 3H), 4.66(br.s, 1H), 7.13(s, 1H), 7.45(d, J=7 Hz, 1H), 7.50(s, 1H).

STARTING MATERIAL SYNTHETIC EXAMPLE 82

4-(tert-butoxycarbonylamino)-6-methylthiochromane-7-carboxylic acid

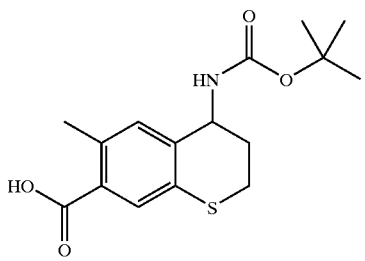

By a similar reaction operation as in Starting Material Synthetic Example 6 using 4-(tert-butoxycarbonylamino)-6-methylthiochromane-7-carboxylic acid methyl ester (2.80 g) and potassium carbonate (3.44 g), the objective 4-(tert-butoxycarbonylamino)-6-methylthiochromane-7-carboxylic acid (2.41 g) was obtained as colorless crystals.

$^1$H-NMR(400 MHz, DMSO-d$_6$) δ=1.43(s, 9H), 2.04(br.s, 2H), 2.42(s, 3H), 3.06(br.s, 2H), 4.66(br.s, 1H), 7.11(s, 1H), 7.44(d, J=9 Hz, 1H), 7.49(s, 1H), 12.86(s, 1H).

STARTING MATERIAL SYNTHETIC EXAMPLE 83

4-(tert-butoxycarbonylamino)-6-methyl-N-(4-pyridyl)thiochromane-7-carboxamide

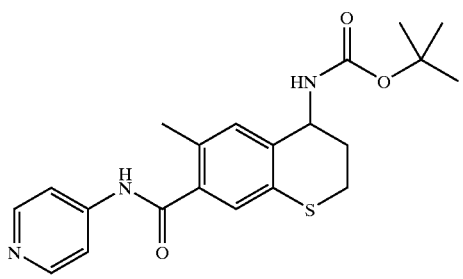

By a similar reaction operation as in Starting Material Synthetic Example 53 using 4-(tert-butoxycarbonylamino)-6-methylthiochromane-7-carboxylic acid (1.00 g), 4-aminopyridine (321 mg) and 2-chloro-1-methylpyridinium iodide (949 mg), the objective 4-(tert-butoxycarbonylamino)-6-methyl-N-(4-pyridyl)thiochromane-7-carboxamide (834 mg) was obtained as colorless crystals.

$^1$H-NMR(400 MHz, DMSO-d$_6$) δ=1.44(s, 9H), 2.06(br.s, 2H), 2.29(s, 3H), 3.08(br.s, 2H), 4.67(br.s, 1H), 7.14(s, 1H), 7.20(s, 1H), 7.46(d, J=8 Hz, 1H), 7.69(d, J=6 Hz, 2H), 8.46(d, J=6 Hz, 2H), 10.65(s, 1H).

STARTING MATERIAL SYNTHETIC EXAMPLE 84

4-(tert-butoxycarbonylamino)-6-methyl-1,1-dioxythiochromane-7-carboxylic acid

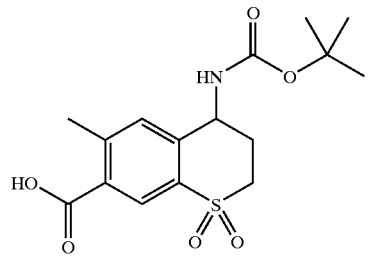

By a similar reaction operation as in Starting Material Synthetic Example 55 using 4-(tert-butoxycarbonylamino)-6-methylthiochromane-7-carboxylic acid (1.00 g) and 2KHSO$_5$·KHSO$_4$·K$_2$SO$_4$ (5.72 g) the objective 4-(tert-butoxycarbonylamino)-6-methyl-1,1-dioxythiochromane-7-carboxylic acid (1.03 g) was obtained as colorless crystals.

$^1$H-NMR(400 MHz, DMSO-d$_6$) δ=1.44(s, 9H), 2.41(br.s, 2H), 2.57(s, 3H), 3.55–3.75(m, 2H), 4.96(br.s, 1H), 7.28(s, 1H), 7.68(d, J=9 Hz, 1H), 8.14(s, 1H), 13.37(br.s, 1H).

STARTING MATERIAL SYNTHETIC EXAMPLE 85

4-(tert-butoxycarbonylamino)-6-methyl-1,1-dioxy-N-(4-pyridyl)thiochromane-7-carboxamide

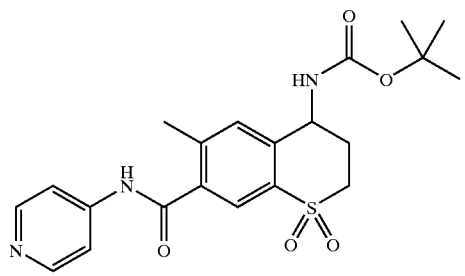

By a similar reaction operation as in Starting Material Synthetic Example 53 using 4-(tert-butoxycarbonylamino)-6-methyl-1,1-dioxythiochromane-7-carboxylic acid (950 mg), 4-aminopyridine (277 mg) and 2-chloro-1-methylpyridinium iodide (820 mg), the objective 4-(tert-butoxycarbonylamino)-6-methyl-1,1-dioxy-N-(4-pyridyl)thiochromane-7-carboxamide (708 mg) was obtained as colorless crystals.

$^1$H-NMR(400 MHz, DMSO-d$_6$) δ=1.45(s, 9H), 2.40–2.55 (m, 2H), 2.43(s, 3H), 3.66(br.s, 2H), 4.95(br.s, 1H), 7.31(s, 1H), 7.65–7.75(m, 3H), 7.83(s, 1H), 8.49(d, J=5 Hz, 2H), 10.91(s, 1H).

STARTING MATERIAL SYNTHETIC EXAMPLE 86

(R)-4-hydroxy-6-methylthiochromane-7-carboxylic acid methyl ester

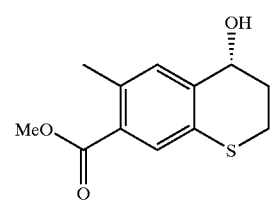

By a similar reaction operation as in Starting Material Synthetic Example 31 using 4-oxy-6-methylthiochromane-7-carboxylic acid methyl ester (9.90 g), (S)-5,5-diphenyl-2-methyl-3,4-propano-1,3,2-oxazaborolidine(1.0 M toluene solution, 4.19 ml) and borane-methyl sulfide complex (2.0 M toluene solution, 31.4 ml), the objective (R)-4-hydroxy-6-methylthiochromane-7-carboxylic acid methyl ester (8.20 g) was obtained as colorless crystals.

$^1$H-NMR(400 MHz, DMSO-d$_6$) δ=1.90–2.10(m, 2H), 2.44(s, 3H), 2.95–3.05(m, 1H), 3.10–3.20(m, 1H), 3.80(s, 3H), 4.59(br.s, 1H), 5.51(d, J=5 Hz, 1H), 7.32(s, 1H), 7.49(s, 1H).

STARTING MATERIAL SYNTHETIC EXAMPLE 87

(S)-4-azide-6-methylthiochromane-7-carboxylic acid methyl ester

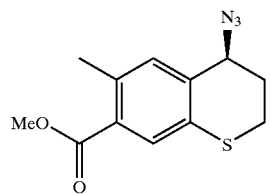

By a similar reaction operation as in Starting Material Synthetic Example 2 using (R)-4-hydroxy-6-methylthiochromane-7-carboxylic acid methyl ester (8.00 g), diphenylphosphoryl azide (18.5 g) and 1,8-diazabicyclo[5.4.0]undecene (10.2 g), a crude product (10.6 g) of the objective (S)-4-azide-6-methylthiochromane-7-carboxylic acid methyl ester was obtained as a yellow oil.

$^1$H-NMR(400 MHz, CDCl$_3$) δ=2.00–2.10(m, 1H), 2.25–2.35(m, 1H), 2.52(s, 3H), 2.80–2.90(m, 1H), 3.20–3.30(m, 1H), 3.86(s, 3H), 4.60(br.s, 1H), 7.07(s, 1H), 7.71(s, 1H).

STARTING MATERIAL SYNTHETIC EXAMPLE 88

(S)-4-amino-6-methylthiochromane-7-carboxylic acid methyl ester

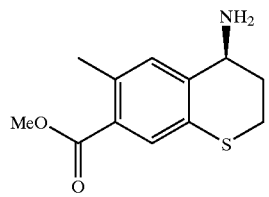

By a similar reaction operation as in Starting Material Synthetic Example 12 using a crude product (10.6 g) of (S)-4-azide-6-methylthiochromane-7-carboxylic acid methyl ester and triphenylphosphine (13.2 g), the objective (S)-4-amino-6-methylthiochromane-7-carboxylic acid methyl ester (8.12 g) was obtained as a yellow oil.

$^1$H-NMR(400 MHz, CDCl$_3$) δ=1.56(s, 2H), 2.05–2.15(m, 2H), 2.53(s, 3H), 2.90–3.00(m, 1H), 3.20–3.30(m, 1H), 3.86(s, 3H), 4.02(t, J=4 Hz, 1H), 7.19(s, 1H), 7.70(s, 1H).

STARTING MATERIAL SYNTHETIC EXAMPLE 89

(S)-4-(tert-butoxycarbonylamino)-6-methylthiochromane-7-carboxylic acid methyl ester

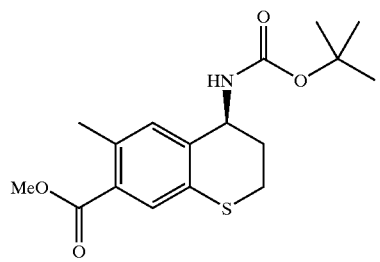

By a similar reaction operation as in Starting Material Synthetic Example 51 using (S)-4-amino-6-methylthiochromane-7-carboxylic acid methyl ester (8.12 g), potassium carbonate (5.68 g) and di-tert-butyldicarbonate (10.5 g), the objective (S)-4-(tert-butoxycarbonylamino)-6-methylthiochromane-7-carboxylic acid methyl ester (8.23 g) was obtained as colorless crystals.

$^1$H-NMR(400 MHz, DMSO-d$_6$) δ=1.41(s, 9H), 2.03(br.s, 2H), 2.40(s, 3H), 3.06(br.s, 2H), 3.78(s, 3H), 4.65(br.s, 1H), 7.12(s, 1H), 7.44(d, J=8 Hz, 1H), 7.49(s, 1H).

STARTING MATERIAL SYNTHETIC EXAMPLE 90

(S)-4-(tert-butoxycarbonylamino)-6-methylthiochromane-7-carboxylic acid

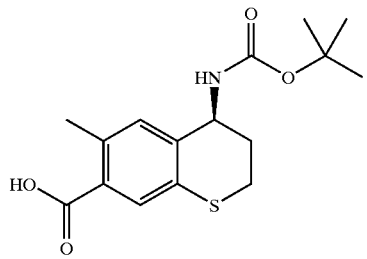

By a similar reaction operation as in Starting Material Synthetic Example 6 using (S)-4-(tert-butoxycarbonylamino)-6-methylthiochromane-7-carboxylic acid methyl ester (8.10 g) and potassium carbonate (9.94 g), the objective (S)-4-(tert-butoxycarbonylamino)-6-methylthiochromane-7-carboxylic acid (6.05 g) was obtained as colorless crystals.

$^1$H-NMR(400 MHz, DMSO-d$_6$) δ=1.42(s, 9H), 2.03(br.s, 2H), 2.41(s, 3H), 3.05(br.s, 2H), 4.65(br.s, 1H), 7.09(s, 1H), 7.42(d, J=6 Hz, 1H), 7.48(s, 1H), 12.85(br.s, 1H).

STARTING MATERIAL SYNTHETIC EXAMPLE 91

(S)-4-(tert-butoxycarbonylamino)-6-methyl-N-(4-pyridyl)thiochromane-7-carboxamide

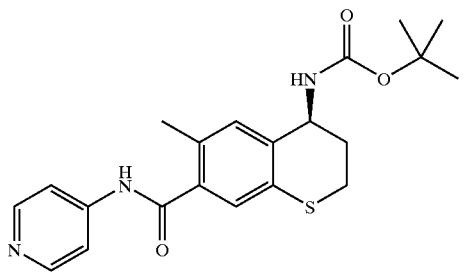

By a similar reaction operation as in Starting Material Synthetic Example 53 using (S)-4-(tert-butoxycarbonylamino)-6-methylthiochromane-7-carboxylic acid (1.00 g), 4-aminopyridine (321 mg) and 2-chloro-1-methylpyridinium iodide (949 mg), the objective (S)-4-(tert-butoxycarbonylamino)-6-methyl-N-(4-pyridyl)thiochromane-7-carboxamide (1.08 g) was obtained as a pale-brown amorphous solid.

$^1$H-NMR(400 MHz, DMSO-d$_6$) δ=1.43(s, 9H), 2.05(br.s, 2H), 2.28(s, 3H), 3.07(br.s, 2H), 4.65(br.s, 1H), 7.13(s, 1H), 7.19(s, 1H), 7.45(d, J=8 Hz, 1H), 7.68(d, J=6 Hz, 2H), 8.44(d, J=6 Hz, 2H), 10.64(s, 1H).

STARTING MATERIAL SYNTHETIC EXAMPLE 92

(S)-4-(tert-butoxycarbonylamino)-6-methyl-1,1-dioxythiochromane-7-carboxylic acid

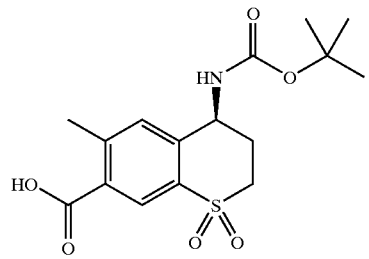

By a similar reaction operation as in Starting Material Synthetic Example 55 using (S)-4-(tert-butoxycarbonylamino)-6-methylthiochromane-7-carboxylic acid (2.00 g) and $2KHSO_5 \cdot KHSO_4 \cdot K_2SO_4$ (11.4 g), the objective (S)-4-(tert-butoxycarbonylamino)-6-methyl-1,1-dioxythiochromane-7-carboxylic acid (2.24 g) was obtained as colorless crystals.

$^1$H-NMR(400 MHz, DMSO-$d_6$) δ=1.44(s, 9H), 2.40(br.s, 2H), 2.57(s, 3H), 3.55–3.75(m, 2H), 4.95(br.s, 1H), 7.28(s, 1H), 7.67(d, J=9 Hz, 1H), 8.14(s, 1H), 13.35(br.s, 1H).

STARTING MATERIAL SYNTHETIC EXAMPLE 93

(S)-4-(tert-butoxycarbonylamino)-6-methyl-1,1-dioxy-N-(4-pyridyl)thiochromane-7-carboxamide

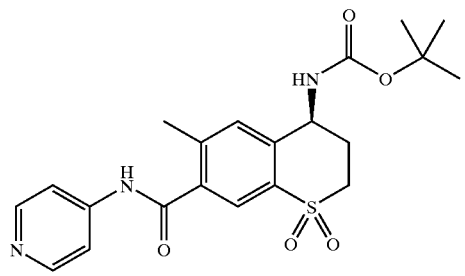

By a similar reaction operation as in Starting Material Synthetic Example 53 using (S)-4-(tert-butoxycarbonylamino)-6-methyl-1,1-dioxythiochromane-7-carboxylic acid (750 mg), 4-aminopyridine (218 mg) and 2-chloro-1-methylpyridinium iodide (646 mg), the objective (S)-4-(tert-butoxycarbonylamino)-6-methyl-1,1-dioxy-N-(4-pyridyl)thiochromane-7-carboxamide (836 mg) was obtained as pale yellow crystals.

$^1$H-NMR(400 MHz, DMSO-$d_6$) δ=1.44(s, 9H), 2.40–2.50 (m, 2H), 2.42(s, 3H), 3.67(br.s, 2H), 4.95(br.s, 1H), 7.30(s, 1H), 7.65–7.75(m, 3H), 7.82(s, 1H), 8.48(d, J=6 Hz, 2H), 10.90(s, 1H).

STARTING MATERIAL SYNTHETIC EXAMPLE 94

(S)-4-(tert-butoxycarbonylamino)-6-methyl-N-(1-triphenylmethylpyrazolo[3,4-b]pyridin-4-yl) thiochromane-7-carboxamide

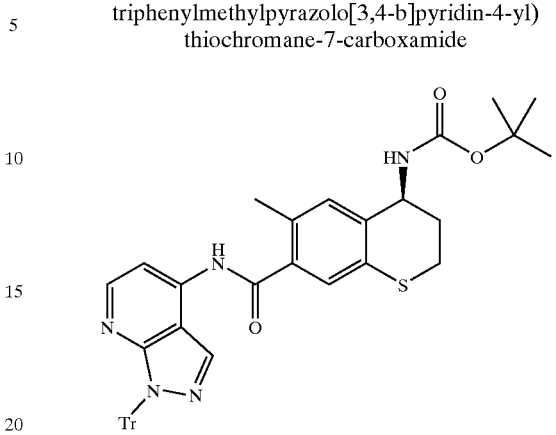

By a similar reaction operation as in Starting Material Synthetic Example 53 using (S)-4-(tert-butoxycarbonylamino)-6-methylthiochromane-7-carboxylic acid (500 mg), 4-amino-1-triphenylmethylpyrazolo[3,4-b]pyridine (641 mg) and 2-chloro-1-methylpyridinium iodide (474 mg), the objective (S)-4-(tert-butoxycarbonylamino)-6-methyl-N-(1-triphenylmethylpyrazolo[3,4-b]pyridin-4-yl) thiochromane-7-carboxamide (767 mg) was obtained as a pale yellow amorphous solid.

$^1$H-NMR(400 MHz, DMSO-$d_6$) δ=1.42(s, 9H), 1.95–2.05 (m, 2H), 2.23(s, 3H), 3.05(br.s, 2H), 4.64(br.s, 1H), 7.05–7.15(m, 8H), 7.35–7.45(m, 10H), 7.88(d, J=5 Hz, 1H), 8.51(d, J=5 Hz, 1H), 8.68(s, 1H), 10.84(s, 1H).

STARTING MATERIAL SYNTHETIC EXAMPLE 95

(S)-4-(tert-butoxycarbonylamino)-6-methyl-1,1-dioxy-N-(1-triphenylmethylpyrazolo[3,4-b]pyridin-4-yl)thiochromane-7-carboxamide

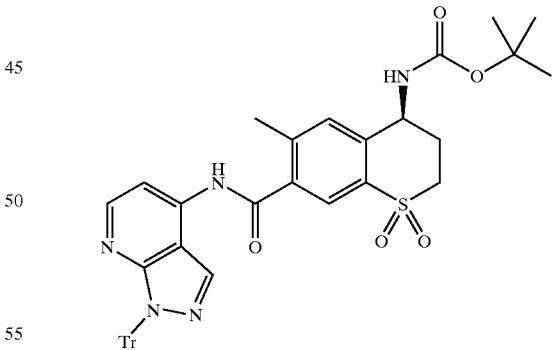

By a similar reaction operation as in Starting Material Synthetic Example 53 using (S)-4-(tert-butoxycarbonylamino)-6-methyl-1,1-dioxythiochromane-7-carboxylic acid (500 mg), 4-amino-1-triphenylmethylpyrazolo[3,4-b]pyridine (530 mg) and 2-chloro-1-methylpyridinium iodide (431 mg), the objective (S)-4-(tert-butoxycarbonylamino)-6-methyl-1,1-dioxy-N-(1-triphenylmethylpyrazolo[3,4-b]pyridin-4-yl) thiochromane-7-carboxamide (706 mg) was obtained as a pale yellow amorphous solid.

¹H-NMR(400 MHz, DMSO-d₆) δ=1.43(s, 9H), 2.30–2.40 (m, 2H), 2.36(s, 3H), 3.64(br.s, 2H), 4.91(br.s, 1H), 7.05–7.15(m, 6H), 7.28(s, 1H), 7.30–7.40(m, 9H), 7.69(d, J=8 Hz, 1H), 7.78(s, 1H), 7.88(d, J=5 Hz, 1H), 8.54(d, J=5 Hz, 1H), 8.63(s, 1H), 11.94(s, 1H).

STARTING MATERIAL SYNTHETIC EXAMPLE 96

(S)-4-(benzyloxycarbonylamino)-6-methylthiochromane-7-carboxylic acid methyl ester

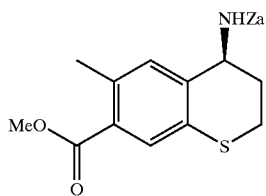

By a similar reaction operation as in Starting Material Synthetic Example 4 using (S)-4-amino-6-methylthiochromane-7-carboxylic acid methyl ester (1.20 g) and benzyloxycarbonyl chloride (0.87 ml), the objective (S)-4-(benzyloxycarbonylamino)-6-methylthiochromane-7-carboxylic acid methyl ester (1.74 g) was obtained as colorless crystals.

¹H-NMR(400 MHz, DMSO-d₆) δ=2.08(br.s, 2H), 2.39(s, 3H), 3.06(br.s, 2H), 3.78(s, 3H), 4.74(br.q, J=7 Hz, 1H), 5.07(d, J=18 Hz, 1H), 5.10(d, J=18 Hz, 1H), 7.14(s, 1H), 7.25–7.40(m, 5H), 7.49(s, 1H), 7.89(d, J=9 Hz, 1H).

STARTING MATERIAL SYNTHETIC EXAMPLE 97

(S)-4-(benzyloxycarbonylamino)-6-methylthiochromane-7-carboxylic acid

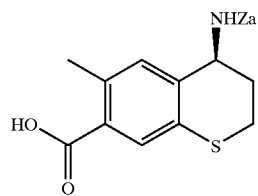

By a similar reaction operation as in Starting Material Synthetic Example 6 using (S)-4-(benzyloxycarbonylamino)-6-methylthiochromane-7-carboxylic acid methyl ester (1.70 g) and potassium carbonate (1.26 g), the objective (S)-4-(benzyloxycarbonylamino)-6-methylthiochromane-7-carboxylic acid (1.54 g) was obtained as colorless crystals.

¹H-NMR(400 MHz, DMSO-d₆) δ=2.05–2.10(m, 2H), 2.39(s, 3H), 3.00–3.10(m, 2H), 4.74(br.q, J=6 Hz, 1H), 5.07(d, J=18 Hz, 1H), 5.10(d, J=18 Hz, 1H), 7.11(s, 1H), 7.25–7.40(m, 5H), 7.49(s, 1H), 7.88(d, J=9 Hz, 1H), 12.86(s, 1H).

STARTING MATERIAL SYNTHETIC EXAMPLE 98

(S)-4-(benzyloxycarbonylamino)-6-methyl-1,1-dioxythiochromane-7-carboxylic acid

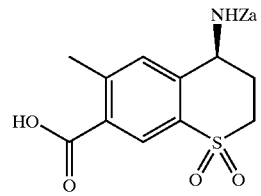

By a similar reaction operation as in Starting Material Synthetic Example 55 using (S)-4-(benzyloxycarbonylamino)-6-methylthiochromane-7-carboxylic acid (750 mg) and 2KHSO₅.KHSO₄.K₂SO₄ (3.87 g), the objective (S)-4-(benzyloxycarbonylamino)-6-methyl-1,1-dioxythiochromane-7-carboxylic acid (765 mg) was obtained as a colorless amorphous solid.

¹H-NMR(400 MHz, DMSO-d₆) δ=2.35–2.50(m, 2H), 2.54(s, 3H), 3.55–3.80(m, 2H), 5.01(br.s, 1H), 5.11(s, 2H), 7.29(s, 1H), 7.30–7.40(m, 5H), 8.08(d, J=9 Hz, 1H), 8.14(s, 1H), 13.38(br.s, 1H).

STARTING MATERIAL SYNTHETIC EXAMPLE 99

(S)-4-(benzyloxycarbonylamino)-6-methyl-1,1-dioxy-N-{1-[2-(trimethylsilyl)ethoxymethyl]pyrrolo[2,3-b]pyridin-4-yl}thiochromane-7-carboxamide

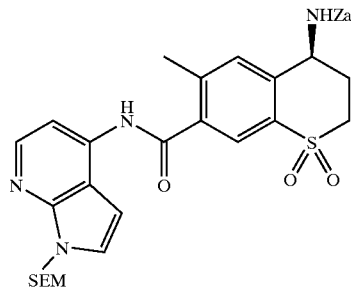

By a similar reaction operation as in Starting Material Synthetic Example 9 using 4-amino-1-[2-(trimethylsilyl)ethoxymethyl]pyrrolo[2,3-b]pyridine (472 mg) and (S)-4-(benzyloxycarbonylamino)-6-methyl-1,1-dioxythiochromane-7-carboxylic acid (700 mg), a crude product (839 mg) of the objective (S)-4-(benzyloxycarbonylamino)-6-methyl-1,1-dioxy-N-{1-[2-(trimethylsilyl)ethoxymethyl]pyrrolo[2,3-b]pyridin-4-yl}thiochromane-7-carboxamide was obtained as a pale-brown amorphous solid.

¹H-NMR(400 MHz, DMSO-d₆) δ=−0.09(s, 9H), 0.75–0.85(m, 2H), 2.40–2.50(m, 2H), 2.50(s, 3H), 3.40–3.55(m, 2H), 3.55–3.75(m, 2H), 5.00–5.20(m, 3H), 5.61(s, 2H), 6.85(s, 1H), 7.35–7.45(m, 5H), 7.54(d, J=3 Hz, 1H), 7.80–7.90(m, 2H), 8.10–8.25(m, 3H), 10.82(s, 1H).

STARTING MATERIAL SYNTHETIC EXAMPLE 100

(S)-4-(benzyloxycarbonylamino)-6-methyl-1,1-dioxy-N-(1H-pyrrolo[2,3-b]pyridin-4-yl)thiochromane-7-carboxamide

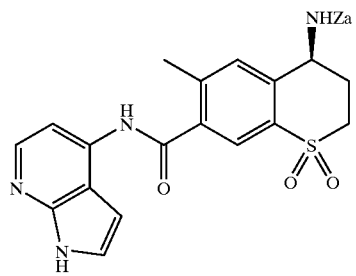

By a similar reaction operation as in Starting Material Synthetic Example 60 using a crude product (839 mg) of (S)-4-(benzyloxycarbonylamino)-6-methyl-1,1-dioxy-N-{1-[2-(trimethylsilyl)ethoxymethyl]pyrrolo[2,3-b]pyridin-4-yl}thiochromane-7-carboxamide, 4N hydrochloric acid dioxane (20 ml) and sodium acetate (5.00 g), the objective (S)-4-(benzyloxycarbonylamino)-6-methyl-1,1-dioxy-N-(1H-pyrrolo[2,3-b]pyridin-4-yl)thiochromane-7-carboxamide (407 mg) was obtained as colorless crystals.

$^1$H-NMR(400 MHz, DMSO-d$_6$) δ=2.40–2.50(m, 2H), 2.41(s, 3H), 3.65–3.70(m, 2H), 5.04(q, J=6 Hz, 1H), 5.13(s, 2H), 6.76(s, 1H), 7.30–7.42(m, 7H), 7.78(d, J=5 Hz, 1H), 7.80(s, 1H), 8.15(d, J=6 Hz, 2H), 10.73(s, 1H), 11.62(s, 1H).

STARTING MATERIAL SYNTHETIC EXAMPLE 101

6-chloro-4-hydroxythiochromane-7-carboxylic acid methyl ester

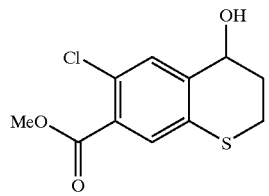

By a similar reaction operation as in Starting Material Synthetic Example 1 using 6-chloro-4-oxythiochromane-7-carboxylic acid methyl ester (1.00 g) synthesized according to a known method and sodium borohydride (147 mg), the objective 6-chloro-4-hydroxythiochromane-7-carboxylic acid methyl ester (750 mg) was obtained as a pale yellow oil.

$^1$H-NMR(400 MHz, DMSO-d$_6$) δ=1.95–2.05(m, 2H), 3.00–3.10(m, 1H), 3.10–3.20(m, 1H), 3.82(s, 3H), 4.61(br.q, J=5 Hz, 1H), 5.69(d, J=5 Hz, 1H), 7.50(s, 1H), 7.52(s, 1H).

STARTING MATERIAL SYNTHETIC EXAMPLE 102

4-azide-6-chlorothiochromane-7-carboxylic acid methyl ester

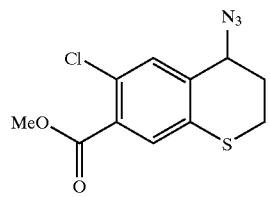

By a similar reaction operation as in Starting Material Synthetic Example 2 using 6-chloro-4-hydroxythiochromane-7-carboxylic acid methyl ester (750 mg), diphenylphosphoryl azide (1.60 g) and 1,8-diazabicyclo[5.4.0]undecene (885 mg), a crude product (513 mg) of the objective 4-azide-6-chlorothiochromane-7-carboxylic acid methyl ester was obtained as a yellow oil.

$^1$H-NMR(400 MHz, DMSO-d$_6$) δ=1.95–2.05(m, 1H), 2.20–2.30(m, 1H), 3.00–3.10(m, 1H), 3.10–3.20(m, 1H), 3.83(s, 3H), 5.03(t, J=2 Hz, 1H), 7.58(s, 1H), 7.63(s, 1H).

STARTING MATERIAL SYNTHETIC EXAMPLE 103

4-amino-6-chlorothiochromane-7-carboxylic acid methyl ester

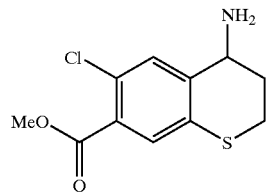

By a similar reaction operation as in Starting Material Synthetic Example 12 using a crude product (513 mg) of 4-azide-6-chlorothiochromane-7-carboxylic acid methyl ester and triphenylphosphine (1.14 g), the objective 4-amino-6-chlorothiochromane-7-carboxylic acid methyl ester (415 mg) was obtained as a yellow oil.

$^1$H-NMR(400 MHz, DMSO-d$_6$) δ=1.85–1.95(m, 1H), 1.95–2.05(m, 1H), 2.05(s, 2H), 2.95–3.05(m, 1H), 3.10–3.20(m, 1H), 3.81(s, 3H), 3.82–3.86(m, 1H), 7.47(s, 1H), 7.63(s, 1H).

STARTING MATERIAL SYNTHETIC EXAMPLE 104

4-(tert-butoxycarbonylamino)-6-chlorothiochromane-7-carboxylic acid methyl ester

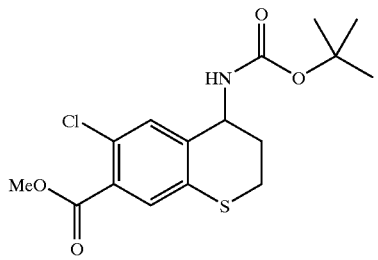

By a similar reaction operation as in Starting Material Synthetic Example 51 using 4-amino-6-chlorothiochromane-7-carboxylic acid methyl ester (400 mg), potassium carbonate (257 mg) and di-tert-butyldicarbonate (473 mg), the objective 4-(tert-butoxycarbonylamino)-6-chlorothiochromane-7-carboxylic acid methyl ester (726 mg) was obtained as colorless crystals.

$^1$H-NMR(400 MHz, DMSO-$d_6$) δ=1.42(s, 9H), 1.95–2.10 (m, 2H), 3.00–3.20(m, 2H), 3.82(s, 3H), 4.67(br.s, 1H), 7.30(s, 1H), 7.51(s, 1H), 7.53(d, J=8 Hz, 1H).

STARTING MATERIAL SYNTHETIC EXAMPLE 105

4-(tert-butoxycarbonylamino)-6-chlorothiochromane-7-carboxylic acid

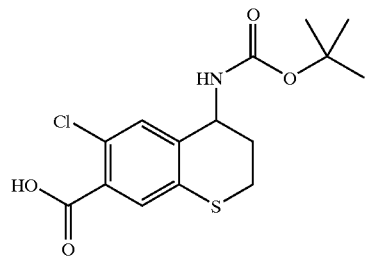

By a similar reaction operation as in Starting Material Synthetic Example 6 using 4-(tert-butoxycarbonylamino)-6-chlorothiochromane-7-carboxylic acid methyl ester (700 mg) and potassium carbonate (541 mg), the objective 4-(tert-butoxycarbonylamino)-6-chlorothiochromane-7-carboxylic acid (424 mg) was obtained as colorless crystals.

$^1$H-NMR(400 MHz, DMSO-$d_6$) δ=1.42(s, 9H), 1.95–2.10 (m, 2H), 3.05–3.15(m, 2H), 4.66(br.s, 1H), 7.27(s, 1H), 7.47(s, 1H), 7.52(d, J=8 Hz, 1H), 13.39(s, 1H).

STARTING MATERIAL SYNTHETIC EXAMPLE 106

4-(tert-butoxycarbonylamino)-6-chloro-N-(4-pyridyl)thiochromane-7-carboxamide

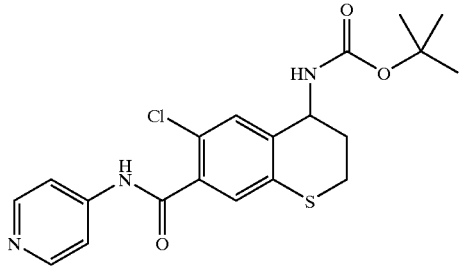

By a similar reaction operation as in Starting Material Synthetic Example 53 using 4-(tert-butoxycarbonylamino)-6-chlorothiochromane-7-carboxylic acid (200 mg), 4-aminopyridine (54.7 mg) and 2-chloro-1-methylpyridinium iodide (178 mg), the objective 4-(tert-butoxycarbonylamino)-6-chloro-N-(4-pyridyl) thiochromane-7-carboxamide (254 mg) was obtained as a colorless amorphous solid.

$^1$H-NMR(400 MHz, DMSO-$d_6$) δ=1.43(s, 9H), 1.95–2.15 (m, 2H), 3.12(br.s, 2H), 4.68(br.s, 1H), 7.30(s, 1H), 7.35(s, 1H), 7.57(d, J=8 Hz, 1H), 7.65(d, J=6 Hz, 2H), 8.47(d, J=6 Hz, 2H), 10.85(s, 1H).

STARTING MATERIAL SYNTHETIC EXAMPLE 107

4-(tert-butoxycarbonylamino)-6-chloro-1,1-dioxythiochromane-7-carboxylic acid

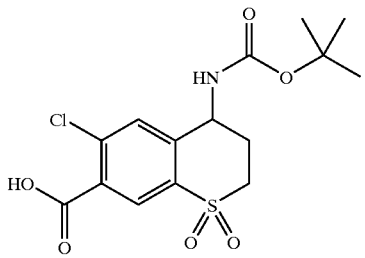

By a similar reaction operation as in Starting Material Synthetic Example 55 using 4-(tert-butoxycarbonylamino)-6-chlorothiochromane-7-carboxylic acid (175 mg) and 2KHSO$_5$.KHSO$_4$.K$_2$SO$_4$ (931 mg) the objective 4-(tert-butoxycarbonylamino)-6-chloro-1,1-dioxythiochromane-7-carboxylic acid (180 mg) was obtained as colorless crystals.

$^1$H-NMR(400 MHz, DMSO-$d_6$) δ=1.43(s, 9H), 2.41(br.s, 2H), 3.60–3.80(m, 2H), 4.96(br.q, J=6 Hz, 1H), 7.46(s, 1H), 7.74(d, J=9 Hz, 1H), 8.12(s, 1H), 13.91(br.s, 1H).

STARTING MATERIAL SYNTHETIC EXAMPLE 108

4-(tert-butoxycarbonylamino)-6-chloro-1,1-dioxy-N-(4-pyridyl)thiochromane-7-carboxamide

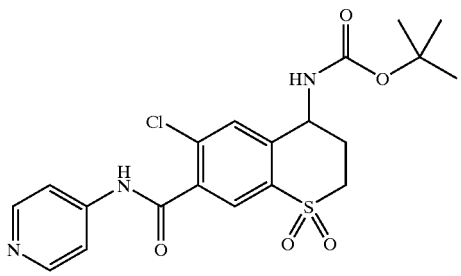

By a similar reaction operation as in Starting Material Synthetic Example 53 using 4-(tert-butoxycarbonylamino)-6-chloro-1,1-dioxythiochromane-7-carboxylic acid (180 mg), 4-aminopyridine (45.1 mg) and 2-chloro-1-methylpyridinium iodide (147 mg), the objective 4-(tert-butoxycarbonylamino)-6-chloro-1,1-dioxy-N-(4-pyridyl)thiochromane-7-carboxamide (191 mg) was obtained as colorless crystals.

$^1$H-NMR(400 MHz, DMSO-d$_6$) δ=1.44(s, 9H), 2.40–2.50 (m, 2H), 3.65–3.80(m, 2H), 4.99(br.q, J=6 Hz, 1H), 7.48(s, 1H), 7.6.5(d, J=6 Hz, 2H), 7.81(d, J=9 Hz, 1H), 8.00(s, 1H), 8.49(d, J=6 Hz, 2H), 11.07(s, 1H).

STARTING MATERIAL SYNTHETIC EXAMPLE 109

(R)-6-chloro-4-hydroxythiochromane-7-carboxylic acid methyl ester

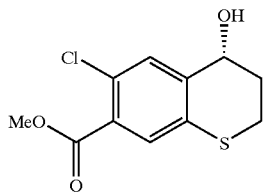

By a similar reaction operation as in Starting Material Synthetic Example 31 using 6-chloro-4-oxythiochromane-7-carboxylic acid methyl ester (5.00 g), (S)-5,5-diphenyl-2-methyl-3,4-propano-1,3,2-oxazaborolidine (1.0 M toluene solution, 1.95 ml) and borane-methyl sulfide complex (2.0 M toluene solution, 14.6 ml), the objective (R)-6-chloro-4-hydroxythiochromane-7-carboxylic acid methyl ester (3.82 g) was obtained as colorless crystals.

$^1$H-NMR(400 MHz, DMSO-d$_6$) δ=1.95–2.05(m, 2H), 3.00–3.10(m, 1H), 3–0.10–3.20(m, 1H), 3.82(s, 3H), 4.61 (br.q, J=5 Hz, 1H), 5.68(d, J=5 Hz, 1H), 7.50(s, 1H), 7.52(s, 1H).

STARTING MATERIAL SYNTHETIC EXAMPLE 110

(S)-4-azide-6-chlorothiochromane-7-carboxylic acid methyl ester

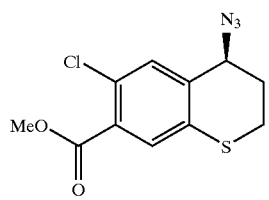

By a similar reaction operation as in Starting Material Synthetic Example 2 using (R)-6-chloro-4-hydroxythiochromane-7-carboxylic acid methyl ester (3.50 g), diphenylphosphoryl azide (7.43 g) and 1,8-diazabicyclo [5.4.0]undecene (4.10 g), a crude product (1.32 g) of the objective (S)-4-azide-6-chlorothiochromane-7-carboxylic acid methyl ester was obtained as a yellow oil.

$^1$H-NMR(400 MHz, DMSO-d$_6$) δ=1.90–2.05(m, 1H), 2.20–2.30(m, 1H), 3.00–3.10(m, 1H), 3.10–3.20(m, 1H), 3.83(s, 3H), 5.04(br.s, 1H), 7.59(s, 1H), 7.63(s, 1H).

STARTING MATERIAL SYNTHETIC EXAMPLE 111

(S)-4-amino-6-chlorothiochromane-7-carboxylic acid methyl ester

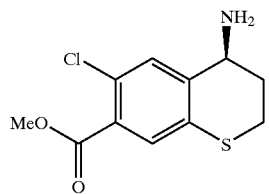

By a similar reaction operation as in Starting Material Synthetic Example 12 using a crude product (1.30 g) of (S)-4-azide-6-chlorothiochromane-7-carboxylic acid methyl ester and triphenylphosphine (1.80 g), the objective (S)-4-amino-6-chlorothiochromane-7-carboxylic acid methyl ester (1.01 g) was obtained as a yellow oil.

$^1$H-NMR(400 MHz, DMSO-d$_6$) δ=1.85–1.95(m, 1H), 1.95–2.05(m, 1H), 2.04(s, 2H), 2.95–3.05(m, 1H), 3.10–3.20(m, 1H), 3.81(s, 3H), 3.81–3.85(m, 1H), 7.47(s, 1H), 7.63(s, 1H).

STARTING MATERIAL SYNTHETIC EXAMPLE 112

(S)-4-(tert-butoxycarbonylamino)-6-chlorothiochromane-7-carboxylic acid methyl ester

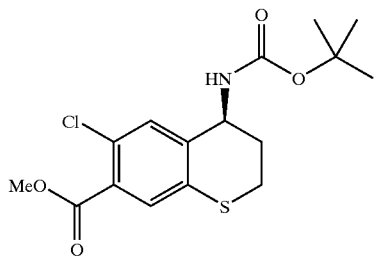

By a similar reaction operation as in Starting Material Synthetic Example 51 using (S)-4-amino-6-chlorothiochromane-7-carboxylic acid methyl ester (1.00 g), potassium carbonate (643 mg) and di-tert-butyldicarbonate (1.18 g), the objective (S)-4-(tert-butoxycarbonylamino)-6-chlorothiochromane-7-carboxylic acid methyl ester (1.18 g) was obtained as colorless crystals.

$^1$H-NMR(400 MHz, DMSO-d$_6$) δ=1.42(s, 9H), 1.95–2.15 (m, 2H), 3.05–3.15(m, 2H), 3.82(s, 3H), 4.67(br.s, 1H), 7.29(s, 1H), 7.51(s, 1H), 7.53(d, J=8 Hz, 1H).

STARTING MATERIAL SYNTHETIC EXAMPLE 113

(S)-4-(tert-butoxycarbonylamino)-6-chlorothiochromane-7-carboxylic acid

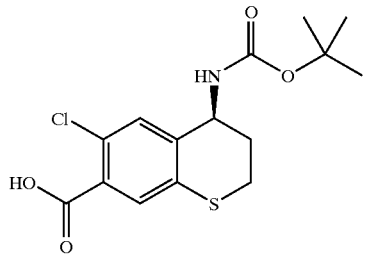

By a similar reaction operation as in Starting Material Synthetic Example 6 using (S)-4-(tert-butoxycarbonylamino)-6-chlorothiochromane-7-carboxylic acid methyl ester (1.10 g) and potassium carbonate (847 mg), the objective (S)-4-(tert-butoxycarbonylamino)-6-chlorothiochromane-7-carboxylic acid (921 mg) was obtained as colorless crystals.

$^1$H-NMR(400 MHz, DMSO-d$_6$) δ=1.42(s, 9H), 1.95–2.10 (m, 2H), 3.05–3.15(m, 2H), 4.66(br.s, 1H), 7.27(s, 1H), 7.48(s, 1H), 7.51(d, J=8 Hz, 1H), 13.40(br.s, 1H).

STARTING MATERIAL SYNTHETIC EXAMPLE 114

(S)-4-(tert-butoxycarbonylamino)-6-chloro-N-(4-pyridyl)thiochromane-7-carboxamide

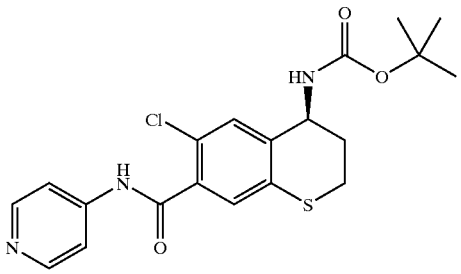

By a similar reaction operation as in Starting Material Synthetic Example 53 using (S)-4-(tert-butoxycarbonylamino)-6-chlorothiochromane-7-carboxylic acid (250 mg), 4-aminopyridine (68.4 mg) and 2-chloro-1-methylpyridinium iodide (222 mg), the objective (S)-4-(tert-butoxycarbonylamino)-6-chloro-N-(4-pyridyl) thiochromane-7-carboxamide (317 mg) was obtained as a colorless amorphous solid.

$^1$H-NMR(400 MHz, DMSO-d$_6$) δ=1.43(s, 9H), 1.95–2.10 (m, 2H), 3.12(br.s, 2H), 4.68(br.s, 1H), 7.30(s, 1H) 7.35(s, 1H), 7.56(d, J=8 Hz, 1H), 7.65(d, J=6 Hz, 2H), 8.47(d, J=6 Hz, 2H), 10.85(s, 1H).

STARTING MATERIAL SYNTHETIC EXAMPLE 115

(S)-4-(tert-butoxycarbonylamino)-6-chloro-1,1-dioxythiochromane-7-carboxylic acid

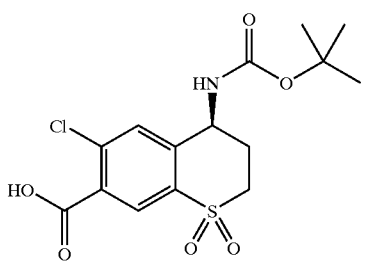

By a similar reaction operation as in Starting Material Synthetic Example 55 using (S)-4-(tert-butoxycarbonylamino)-6-chlorothiochromane-7-carboxylic acid (450 mg) and 2KHSO$_5$.KHSO$_4$.K$_2$SO$_4$ (2.42 g), the objective (S)-4-(tert-butoxycarbonylamino)-6-chloro-1,1-dioxythiochromane-7-carboxylic acid (476 mg) was obtained as colorless crystals.

$^1$H-NMR(400 MHz, DMSO-d$_6$) δ=1.43(s, 9H), 2.40–2.50 (m, 2H), 3.65–3.85(m, 2H), 4.97(br.q, J=7 Hz, 1H), 7.45(s, 1H), 7.74(d, J=9 Hz, 1H), 8.12(s, 1H), 13.91(br.s, 1H).

STARTING MATERIAL SYNTHETIC EXAMPLE 116

(S)-4-(tert-butoxycarbonylamino)-6-chloro-1,1-dioxy-N-(4-pyridyl)thiochromane-7-carboxamide

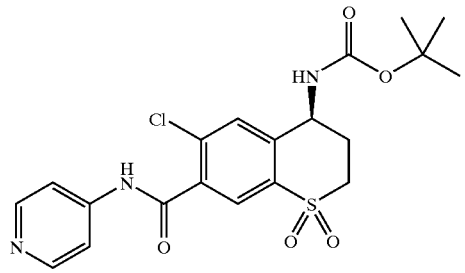

By a similar reaction operation as in Starting Material Synthetic Example 53 using (S)-4-(tert-butoxycarbonylamino)-6-chloro-1,1-dioxythiochromane-7-carboxylic acid (250 mg), 4-aminopyridine (62.6 mg) and 2-chloro-1-methylpyridinium iodide (203 mg), the objective (S)-4-(tert-butoxycarbonylamino)-6-chloro-1,1-dioxy-N-(4-pyridyl)thiochromane-7-carboxamide (276 mg) was obtained as colorless crystals.

$^1$H-NMR(400 MHz, DMSO-$d_6$) δ=1.44(s, 9H), 2.40–2.55 (m, 2H), 3.65–3.85(m, 2H), 4.99(br.q, J=6 Hz, 1H), 7.48(s, 1H), 7.65(d, J=6 Hz, 2H), 7.81(d, J=9 Hz, 1H), 8.00(s, 1H), 8.49(d, J=6 Hz, 2H), 11.07(s, 1H).

STARTING MATERIAL SYNTHETIC EXAMPLE 117

(S)-4-(tert-butoxycarbonylamino)-6-chloro-N-(1-triphenylmethylpyrazolo[3,4-b]pyridin-4-yl)thiochromane-7-carboxamide

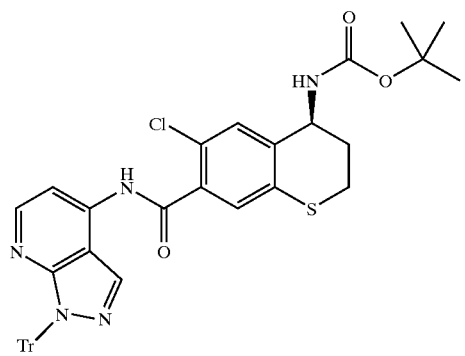

By a similar reaction operation as in Starting Material Synthetic Example 53 using (S)-4-(tert-butoxycarbonylamino)-6-chloro-thiochromane-7-carboxylic acid (150 mg), 4-amino-1-triphenylmethylpyrazolo[3,4-b]pyridine (163 mg) and 2-chloro-1-methylpyridinium iodide (133 mg), the objective (S)-4-(tert-butoxycarbonylamino)-6-chloro-N-(1-triphenylmethylpyrazolo[3,4-b]pyridin-4-yl)thiochromane-7-carboxamide (262 mg) was obtained as a pale yellow amorphous solid.

$^1$H-NMR(400 MHz, DMSO-$d_6$) δ=1.43(s, 9H), 1.95–2.15 (m, 2H), 3.10(br.s, 2H), 4.65(br.s, 1H), 7.05–7.15(m, 6H), 7.27(s, 1H), 7.34(s, 1H), 7.34–7.40(m, 9H), 7.53(d, J=8 Hz, 1H), 7.87(d, J=5 Hz, 1H), 8.53(d, J=5 Hz, 1H), 8.64(s, 1H), 11.02(s, 1H).

STARTING MATERIAL SYNTHETIC EXAMPLE 118

(S)-4-(tert-butoxycarbonylamino)-6-chloro-1,1-dioxy-N-(1-triphenylmethylpyrazolo[3,4-b]pyridin-4-yl)thiochromane-7-carboxamide

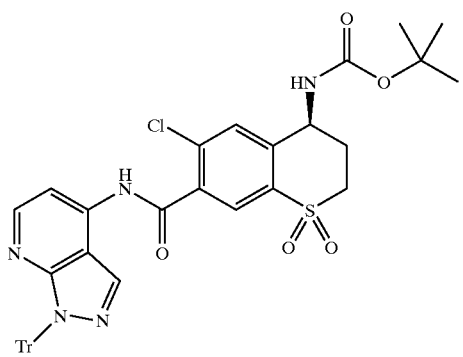

By a similar reaction operation as in Starting Material Synthetic Example 53 using (S)-4-(tert-butoxycarbonylamino)-6-chloro-1,1-dioxythiochromane-7-carboxylic acid (150 mg), 4-amino-1-triphenylmethylpyrazolo[3,4-b]pyridine (150 mg) and 2-chloro-1-methylpyridinium iodide (122 mg), the objective (S)-4-(tert-butoxycarbonylamino)-6-chloro-1,1-dioxy-N-(1-triphenylmethylpyrazolo[3,4-b]pyridin-4-yl)thiochromane-7-carboxamide (176 mg) was obtained as a pale yellow amorphous solid.

$^1$H-NMR(400 MHz, DMSO-$d_6$) δ=1.43(s, 9H), 2.40–2.50 (m, 2H), 3.65–3.80(m, 2H), 4.96(br.q, J=6 Hz, 1H), 7.05–7.15(m, 6H), 7.35–7.40(m, 9H), 7.46(s, 1H), 7.79(d, J=9 Hz, 1H), 7.88(d, J=4 Hz, 1H), 8.02(s, 1H), 8.56(d, J=4 Hz, 1H), 8.59(s, 1H), 11.22(s, 1H).

STARTING MATERIAL SYNTHETIC EXAMPLE 119

(S)-4-(benzyloxycarbonylamino)-6-chlorothiochromane-7-carboxylic acid methyl ester

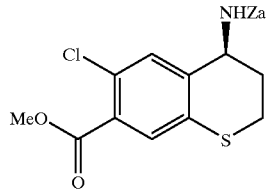

By a similar reaction operation as in Starting Material Synthetic Example 4 using (S)-4-amino-6-chlorothiochromane-7-carboxylic acid methyl ester (450 mg) and benzyloxycarbonyl chloride (0.31 ml), the objective (S)-4-(benzyloxycarbonylamino)-6-chlorothiochromane-7-carboxylic acid methyl ester (478 mg) was obtained as colorless crystals.

$^1$H-NMR(400 MHz, DMSO-$d_6$) δ=2.05–2.15(m, 2H), 3.05–3.20(m, 2H), 3.82(s, 3H), 4.77(br.q, J=7 Hz, 1H), 5.08(d, J=16 Hz, 1H), 5.11(d, J=16 Hz, 1H), 7.25–7.40(m, 6H), 7.52(s, 1H), 7.95(d, J=9 Hz, 1H).

STARTING MATERIAL SYNTHETIC EXAMPLE 120

(S)-4-(benzyloxycarbonylamino)-6-chlorothiochromane-7-carboxylic acid

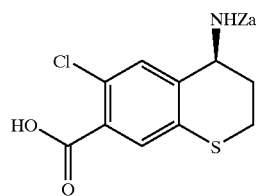

By a similar reaction operation as in Starting Material Synthetic Example 6 using (S)-4-(benzyloxycarbonylamino)-6-chlorothiochromane-7-carboxylic acid methyl ester (450 mg) and potassium carbonate (317 mg), the objective (S)-4-(benzyloxycarbonylamino)-6-chlorothiochromane-7-carboxylic acid (425 mg) was obtained as colorless crystals.

$^1$H-NMR(400 MHz, DMSO-$d_6$) δ=2.00–2.10(m, 2H), 3.00–3.15(m, 2H), 4.76(br.q, J=7 Hz, 1H), 5.08(d, J=13 Hz, 1H), 5.11(d, J=13 Hz, 1H), 7.30–7.40(m, 6H), 7.48(s, 1H), 7.94(d, J=9 Hz, 1H), 13.41(s, 1H).

STARTING MATERIAL SYNTHETIC EXAMPLE 121

(S)-4-(benzyloxycarbonylamino)-6-chloro-1,1-dioxythiochromane-7-carboxylic acid

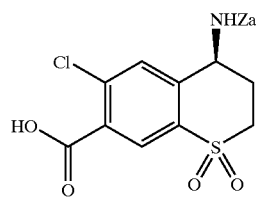

By a similar reaction operation as in Starting Material Synthetic Example 55 using (S)-4-(benzyloxycarbonylamino)-6-chlorothiochromane-7-carboxylic acid (400 mg) and 2KHSO$_5$.KHSO$_4$.K$_2$SO$_4$ (1.96 g), the objective (S)-4-(benzyloxycarbonylamino)-6-chloro-1,1-dioxythiochromane-7-carboxylic acid (379 mg) was obtained as colorless crystals.

$^1$H-NMR(400 MHz, DMSO-$d_6$) δ=2.40–2.50(m, 2H), 3.60–3.70(m, 1H), 3.70–3.80(m, 1H), 5.00–5.15(m, 3H), 7.30–7.40(m, 6H), 7.50(s, 1H), 8.12(s, 1H), 8.14(d, J=10 Hz, 1H), 13.92(br.s, 1H).

STARTING MATERIAL SYNTHETIC EXAMPLE 122

(S)-4-(benzyloxycarbonylamino)-6-chloro-1,1-dioxy-N-{1-[2-(trimethylsilyl)ethoxymethyl]pyrrolo[2,3-b]pyridin-4-yl}thiochromane-7-carboxamide

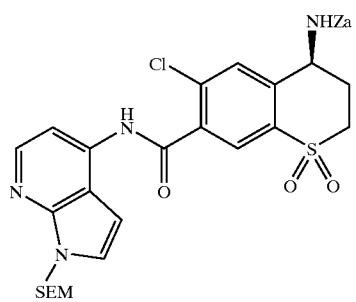

By a similar reaction operation as in Starting Material Synthetic Example 9 using 4-amino-1-[2-(trimethylsilyl)-ethoxymethyl]pyrrolo[2,3-b]pyridine (224 mg) and (S)-4-(benzyloxycarbonylamino)-6-chloro-1,1-dioxythiochromane-7-carboxylic acid (350 mg), a crude product (298 mg) of the objective (S)-4-(benzyloxycarbonylamino)-6-chloro-1,1-dioxy-N-{1-[2-(trimethylsilyl)ethoxymethyl]pyrrolo[2,3-b]pyridin-4-yl}thiochromane-7-carboxamide was obtained as a colorless amorphous solid.

$^1$H-NMR(400 MHz, DMSO-$d_6$) δ=–0.09(s, 9H), 0.82(t, J=8 Hz, 2H), 2.40–2.50(m, 2H), 3.51(t, J=8 Hz, 2H), 3.70–3.90(m, 2H), 5.00–5.15(m, 3H), 5.62(s, 2H), 6.85(d, J=3 Hz, 1H), 7.30–7.40(m, 5H), 7.55(s, 1H), 7.90(d, J=5 Hz, 1H), 8.02(s, 1H), 8.24(d, J=5 Hz, 2H), 10.96(s, 1H).

STARTING MATERIAL SYNTHETIC EXAMPLE 123

(S)-4-(benzyloxycarbonylamino)-6-chloro-1,1-dioxy-N-(1H-pyrrolo[2,3-b]pyridin-4-yl)thiochromane-7-carboxamide

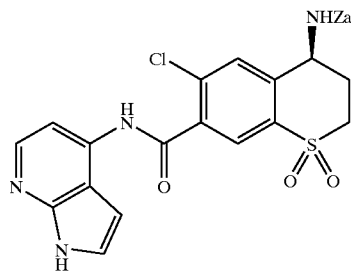

By a similar reaction operation as in Starting Material Synthetic Example 60 using a crude product (290 mg) of (S)-4-(benzyloxycarbonylamino)-6-chloro-1,1-dioxy-N-{1-[2-(trimethylsilyl)ethoxymethyl]pyrrolo[2,3-b]pyridin-4-yl}thiochromane-7-carboxamide, 4N hydrochloric acid dioxane (15 ml) and sodium acetate (3.00 g), the objective (S)-4-(benzyloxycarbonylamino)-6-chloro-1,1-dioxy-N-(1H-pyrrolo[2,3-b]pyridin-4-yl)thiochromane-7-carboxamide (136 mg) was obtained as a colorless amorphous solid.

$^1$H-NMR(400 MHz, DMSO-$d_6$) δ=2.45–2.55(m, 2H), 3.60–3.85(m, 2H), 5.00–5.15(m, 1H), 5.13(s, 2H), 6.75(s,

1H), 7.30–7.40(m, 6H), 7.53(s, 1H), 7.83(d, J=5 Hz, 1H), 7.98(s, 1H), 8.16(d, J=5 Hz, 1H), 8.23(d, J=9 Hz, 1H), 10.87(s, 1H), 11.65(s, 1H).

STARTING MATERIAL SYNTHETIC EXAMPLE 124

4-hydroxy-6-methoxythiochromane-7-carboxylic acid methyl ester

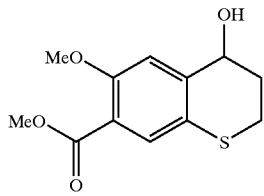

By a similar reaction operation as in Starting Material Synthetic Example 1 using 6-methoxy-4-oxythiochromane-7-carboxylic acid methyl ester (1.50 g) synthesized according to a known method and sodium borohydride (595 mg), the objective 4-hydroxy-6-methoxythiochromane-7-carboxylic acid methyl ester (1.16 g) was obtained as pale yellow crystals.

$^1$H-NMR(400 MHz, DMSO-d$_6$) δ=1.95–2.10(m, 2H), 2.90–3.05(m, 1H), 3.05–3.15(m, 1H), 3.76(s, 3H), 3.78(s, 3H), 4.59(br.s, 1H), 5.58(d, J=5 Hz, 1H), 7.20(s, 1H), 7.32(s, 1H).

STARTING MATERIAL SYNTHETIC EXAMPLE 125

4-azide-6-methoxythiochromane-7-carboxylic acid methyl ester

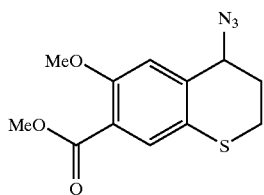

By a similar reaction operation as in Starting Material Synthetic Example 2 using 4-hydroxy-6-methoxythiochromane-7-carboxylic acid methyl ester (1.10 g), diphenylphosphoryl azide (2.38 g) and 1,8-diazabicyclo[5.4.0]undecene (1.31 g), a crude product (1.12 g) of the objective 4-azide-6-methoxythiochromane-7-carboxylic acid methyl ester was obtained as a pale yellow oil.

$^1$H-NMR(400 MHz, DMSO-d$_6$) δ=1.90–2.10(m, 1H), 2.25–2.35(m, 1H), 2.95–3.05(m, 1H), 3.10–3.20(m, 1H), 3.78(s, 3H), 3.81(s, 3H), 5.00(br.s, 1H), 7.23(s, 1H), 7.40(s, 1H).

STARTING MATERIAL SYNTHETIC EXAMPLE 126

4-amino-6-methoxythiochromane-7-carboxylic acid methyl ester

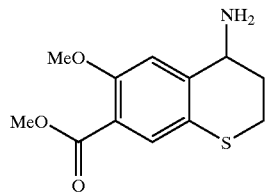

By a similar reaction operation as in Starting Material Synthetic Example 12 using a crude product (1.10 g) of 4-azide-6-methoxythiochromane-7-carboxylic acid methyl ester and triphenylphosphine (1.55 g), the objective 4-amino-6-methoxythiochromane-7-carboxylic acid methyl ester (718 mg) was obtained as yellow crystals.

$^1$H-NMR(400 MHz, DMSO-d$_6$) δ=1.90–2.00(m, 1H), 2.00–2.10(m, 3H), 2.90–3.00(m, 1H), 3.10–3.20(m, 1H), 3.75(s, 3H), 3.79(s, 3H), 3.86(t, J=5 Hz, 1H), 7.27(s, 1H), 7.31(s, 1H).

STARTING MATERIAL SYNTHETIC EXAMPLE 127

4-(tert-butoxycarbonylamino)-6-methoxythiochromane-7-carboxylic acid methyl ester

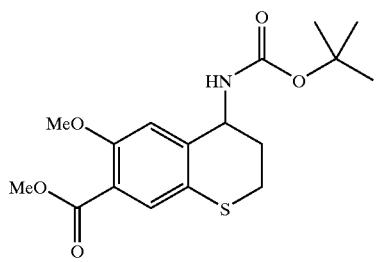

By a similar reaction operation as in Starting Material Synthetic Example 51 using 4-amino-6-methoxythiochromane-7-carboxylic acid methyl ester (700 mg), potassium carbonate (535 mg) and di-tert-butyldicarbonate (725 mg), the objective 4-(tert-butoxycarbonylamino)-6-methoxythiochromane-7-carboxylic acid methyl ester (827 mg) was obtained as colorless crystals.

$^1$H-NMR(400 MHz, DMSO-d$_6$) δ=1.42(s, 9H), 1.95–2.15(m, 2H), 2.95–3.15(m, 2H), 3.72(s, 3H), 3.75(s, 3H), 4.67(br.s, 1H), 6.98(s, 1H), 7.33(s, 1H), 7.51(d, J=9 Hz, 1H).

STARTING MATERIAL SYNTHETIC EXAMPLE 128

4-(tert-butoxycarbonylamino)-6-methoxythiochromane-7-carboxylic acid

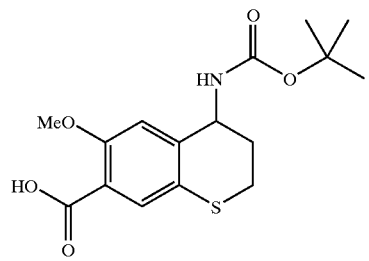

By a similar reaction operation as in Starting Material Synthetic Example 6 using 4-(tert-butoxycarbonylamino)-6-methoxythiochromane-7-carboxylic acid methyl ester (800 mg) and potassium carbonate (627 mg), the objective 4-(tert-butoxycarbonylamino)-6-methoxythiochromane-7-carboxylic acid (722 mg) was obtained as colorless crystals.

$^1$H-NMR(400 MHz, DMSO-d$_6$) δ=1.42(s, 9H), 1.95–2.15 (m, 2H), 2.95–3.10(m, 2H), 3.72(s, 3H), 4.66(br.s, 1H), 6.96(s, 1H), 7.30(s, 1H), 7.50(d, J=8 Hz, 1H), 12.67(s, 1H).

STARTING MATERIAL SYNTHETIC EXAMPLE 129

4-(tert-butoxycarbonylamino)-6-methoxy-N-(4-pyridyl)thiochromane-7-carboxamide

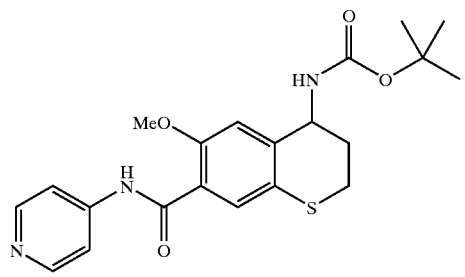

By a similar reaction operation as in Starting Material Synthetic Example 53 using 4-(tert-butoxycarbonylamino)-6-methoxythiochromane-7-carboxylic acid (300 mg), 4-aminopyridine (83.3 mg) and 2-chloro-1-methylpyridinium iodide (271 mg), the objective 4-(tert-butoxycarbonylamino)-6-methoxy-N-(4-pyridyl)thiochromane-7-carboxamide (352 mg) as a pale-red amorphous solid.

$^1$H-NMR(400 MHz, DMSO-d$_6$) δ=1.45(s, 9H), 1.95–2.20 (m, 2H), 3.00–3.15(m, 2H), 3.81(s, 3H), 4.69(br.s, 1H), 7.04(s, 1H), 7.30(s, 1H), 7.54(d, J=9 Hz, 1H), 7.69(d, J=5 Hz, 2H), 8.46(d, J=5 Hz, 2H), 10.43(s, 1H).

STARTING MATERIAL SYNTHETIC EXAMPLE 130

4-(tert-butoxycarbonylamino)-6-methoxy-1,1-dioxythiochromane-7-carboxylic acid

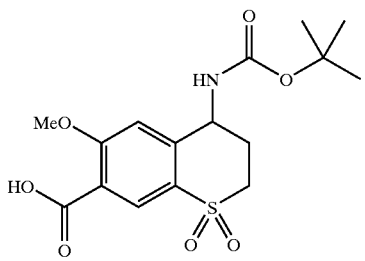

By a similar reaction operation as in Starting Material Synthetic Example 55 using 4-(tert-butoxycarbonylamino)-6-methoxythiochromane-7-carboxylic acid (300 mg) and 2KHSO$_5$.KHSO$_4$.K$_2$SO$_4$ (1.63 g), the objective 4-(tert-butoxycarbonylamino)-6-methoxy-1,1-dioxythiochromane-7-carboxylic acid (271 mg) was obtained as colorless crystals.

$^1$H-NMR(400 MHz, DMSO-d$_6$) δ=1.44(s, 9H), 2.40–2.50 (m, 2H), 3.63(br.s, 2H), 3.84(s, 3H), 4.93(br.q, J=6 Hz, 1H), 7.04(s, 1H), 7.76(d, J=8 Hz, 1H), 7.99(s, 1H), 13.17(br.s, 1H).

STARTING MATERIAL SYNTHETIC EXAMPLE 131

4-(tert-butoxycarbonylamino)-6-methoxy-1,1-dioxy-N-(4-pyridyl)thiochromane-7-carboxamide

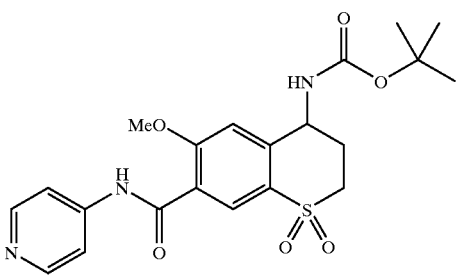

By a similar reaction operation as in Starting Material Synthetic Example 53 using 4-(tert-butoxycarbonylamino)-6-methoxy-1,1-dioxythiochromane-7-carboxylic acid (250 mg), 4-aminopyridine (63.4 mg) and 2-chloro-1-methylpyridinium iodide (206 mg), the objective 4-(tert-butoxycarbonylamino)-6-methoxy-1,1-dioxy-N-(4-pyridyl)thiochromane-7-carboxamide (135 mg) was obtained as a pale-brown amorphous solid.

$^1$H-NMR(400 MHz, DMSO-d$_6$) δ=1.45(s, 9H), 2.40–2.50 (m, 2H), 3.66(br.t, J=6 Hz, 2H), 3.90(s, 3H), 4.98(br.q, J=6 Hz, 1H), 7.09(s, 1H), 7.69(d, J=6 Hz, 2H), 7.81(d, J=9 Hz, 1H), 7.91(s, 1H), 8.48(d, J=6 Hz, 2H), 10.59(s, 1H).

STARTING MATERIAL SYNTHETIC EXAMPLE 132

(R)-4-hydroxy-6-methoxythiochromane-7-carboxylic acid methyl ester

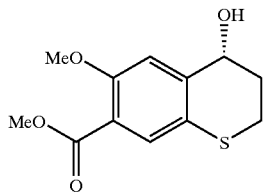

By a similar reaction operation as in Starting Material Synthetic Example 31 using 6-methoxy-4-oxythiochromane-7-carboxylic acid methyl ester (2.50 g), (S)-5,5-diphenyl-2-methyl-3,4-propano-1,3,2-oxazaborolidine (1.0 M toluene solution, 0.992 ml) and borane-methyl sulfide complex (2.0 M toluene solution, 14.9 ml), the objective (R)-4-hydroxy-6-methoxythiochromane-7-carboxylic acid methyl ester (2.14 g) was obtained as colorless crystals.

$^1$H-NMR(400 MHz, DMSO-d$_6$) δ=1.90–2.10(m, 2H), 2.90–3.05(m, 1H), 3.05–3.15(m, 1H), 3.75(s, 3H), 3.78(s, 3H), 4.58(br.s, 1H), 5.57(d, J=5 Hz, 1H), 7.19(s, 1H), 7.32(s, 1H).

STARTING MATERIAL SYNTHETIC EXAMPLE 133

(S)-4-azide-6-methoxythiochromane-7-carboxylic acid methyl ester

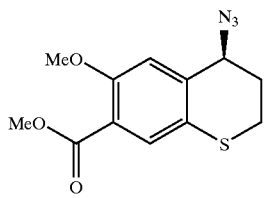

By a similar reaction operation as in Starting Material Synthetic Example 2 using (R)-4-hydroxy-6-methoxythiochromane-7-carboxylic acid methyl ester (2.00 g), diphenylphosphoryl azide (4.33 g) and 1,8-diazabicyclo[5.4.0]undecene (2.39 g), a crude product (2.07 g) of the objective (S)-4-azide-6-methoxythiochromane-7-carboxylic acid methyl ester was obtained as a pale yellow oil.

$^1$H-NMR(400 MHz, DMSO-d$_6$) δ=1.95–2.05(m, 1H), 2.20–2.35(m, 1H), 2.95–3.05(m, 1H), 3.05–3.20(m, 1H), 3.76(s, 3H), 3.79(s, 3H), 4.98(t, J=4 Hz, 1H), 7.21(s, 1H) 7.38(s, 1H).

STARTING MATERIAL SYNTHETIC EXAMPLE 134

(S)-4-amino-6-methoxythiochromane-7-carboxylic acid methyl ester

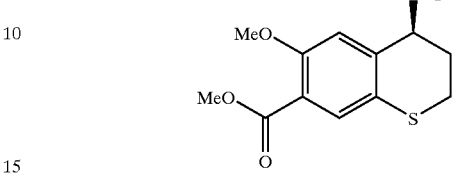

By a similar reaction operation as in Starting Material Synthetic Example 12 using a crude product (2.07 g) of (S)-4-azide-6-methoxythiochromane-7-carboxylic acid methyl ester and triphenylphosphine (3.07 g), the objective (S)-4-amino-6-methoxythiochromane-7-carboxylic acid methyl ester (1.84 g) was obtained as yellow crystals.

$^1$H-NMR(400 MHz, DMSO-d$_6$) δ=1.80–1.95(m, 1H), 1.95–2.10(m, 3H), 2.85–3.00(m, 1H), 3.10–3.20(m, 1H), 3.75(s, 3H), 3.79(s, 3H), 3.83–3.88(m, 1H), 7.27(s, 1H), 7.31(s, 1H).

STARTING MATERIAL SYNTHETIC EXAMPLE 135

(S)-4-(tert-butoxycarbonylamino)-6-methoxythiochromane-7-carboxylic acid methyl ester

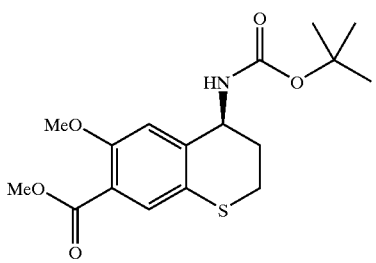

By a similar reaction operation as in Starting Material Synthetic Example 51 using (S)-4-amino-6-methoxythiochromane-7-carboxylic acid methyl ester (1.10 g), potassium carbonate (840 mg) and di-tert-butyldicarbonate (1.14 g), the objective (S)-4-(tert-butoxycarbonylamino)-6-methoxythiochromane-7-carboxylic acid methyl ester (1.23 g) was obtained as colorless crystals.

$^1$H-NMR(400 MHz, DMSO-d$_6$) δ=1.43(s, 9H), 1.95–2.15(m, 2H), 3.00–3.10(m, 2H), 3.73(s, 3H), 3.76(s, 3H), 4.67(br.s, 1H), 7.00(s, 1H), 7.34(s, 1H), 7.52(d, J=8 Hz, 1H).

STARTING MATERIAL SYNTHETIC EXAMPLE 136

(S)-4-(tert-butoxycarbonylamino)-6-methoxythiochromane-7-carboxylic acid

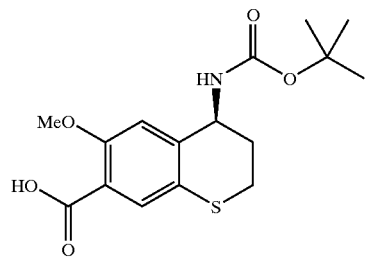

By a similar reaction operation as in Starting Material Synthetic Example 6 using (S)-4-(tert-butoxycarbonylamino)-6-methoxythiochromane-7-carboxylic acid methyl ester (1.10 g) and potassium carbonate (861 mg), the objective (S)-4-(tert-butoxycarbonylamino)-6-methoxythiochromane-7-carboxylic acid (1.01 g) was obtained as colorless crystals.

$^1$H-NMR(400 MHz, DMSO-d$_6$) δ=1.43(s, 9H), 1.95–2.15 (m, 2H), 2.95–3.10(m, 2H), 3.73(s, 3H), 4.67(br.s, 1H), 6.97(s, 1H), 7.32(s, 1H), 7.51(d, J=8 Hz, 1H), 12.68(s, 1H).

STARTING MATERIAL SYNTHETIC EXAMPLE 137

(S)-4-(tert-butoxycarbonylamino)-6-methoxy-N-(4-pyridyl)thiochromane-7-carboxamide

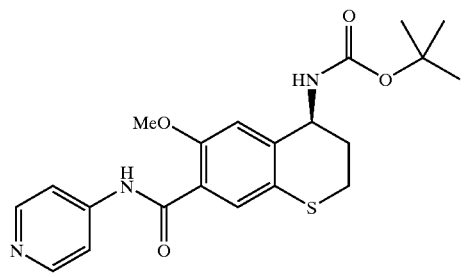

By a similar reaction operation as in Starting Material Synthetic Example 53 using (S)-4-(tert-butoxycarbonylamino)-6-methoxythiochromane-7-carboxylic acid (300 mg), 4-aminopyridine (83.3 mg) and 2-chloro-1-methylpyridinium iodide (271 mg), the objective (S)-4-(tert-butoxycarbonylamino)-6-methoxy-N-(4-pyridyl)thiochromane-7-carboxamide (274 mg) was obtained as a pale-red amorphous solid.

$^1$H-NMR(400 MHz, DMSO-d$_6$) δ=1.45(s, 9H), 1.95–2.20 (m, 2H), 2.95–3.15(m, 2H), 3.81(s, 3H), 4.69(br.s, 1H), 7.04(s, 1H), 7.30(s, 1H), 7.54(d, J=8 Hz, 1H), 7.69(d, J=6 Hz, 2H), 8.46(d, J=6 Hz, 2H), 10.43(s, 1H).

STARTING MATERIAL SYNTHETIC EXAMPLE 138

(S)-4-(tert-butoxycarbonylamino)-6-methoxy-1,1-dioxythiochromane-7-carboxylic acid

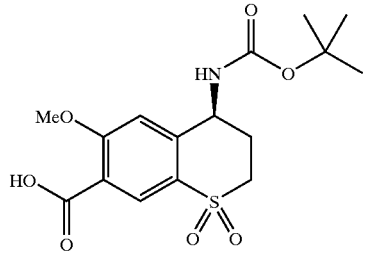

By a similar reaction operation as in Starting Material Synthetic Example 55 using (S)-4-(tert-butoxycarbonylamino)-6-methoxythiochromane-7-carboxylic acid (400 mg) and 2KHSO$_5$.KHSO$_4$.K$_2$SO$_4$ (2.18 g), the objective (S)-4-(tert-butoxycarbonylamino)-6-methoxy-1,1-dioxythiochromane-7-carboxylic acid (376 mg) was obtained as colorless crystals.

$^1$H-NMR(400 MHz, DMSO-d$_6$) δ=1.43(s, 9H), 2.40–2.50 (m, 2H), 3.55–3.65(m, 2H), 3.83(s, 3H), 4.91(br.q, J=6 Hz, 1H), 7.03(s, 1H), 7.75(d, J=8 Hz, 1H), 7.97(s, 1H), 13.16 (br.s, 1H).

STARTING MATERIAL SYNTHETIC EXAMPLE 139

(S)-4-(tert-butoxycarbonylamino)-6-methoxy-1,1-dioxy-N-(4-pyridyl)thiochromane-7-carboxamide

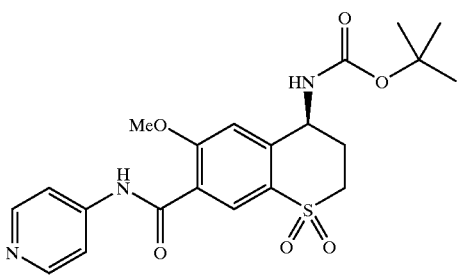

By a similar reaction operation as in Starting Material Synthetic Example 53 using (S)-4-(tert-butoxycarbonylamino)-6-methoxy-1,1-dioxythiochromane-7-carboxylic acid (300 mg), 4-aminopyridine (82.8 mg) and 2-chloro-1-methylpyridinium iodide (269 mg), the objective (S)-4-(tert-butoxycarbonylamino)-6-methoxy-1,1-dioxy-N-(4-pyridyl)thiochromane-7-carboxamide (335 mg) was obtained as a pale yellow amorphous solid.

$^1$H-NMR(400 MHz, DMSO-d$_6$) δ=1.44(s, 9H), 2.40–2.50 (m, 2H), 3.65(br.t, J=6 Hz, 2H), 3.88(s, 3H), 4.96(br.q, J=6 Hz, 1H), 7.08(s, 1H), 7.68(d, J=6 Hz, 2H), 7.80(d, J=9 Hz, 1H), 7.90(s, 1H), 8.47(d, J=6 Hz, 2H), 10.58(s, 1H).

EXAMPLE 1

4-amino-N-(4-pyridyl)thiochromane-7-carboxamide 1,1-dioxide 1HCl 2H$_2$O

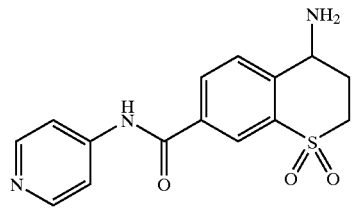

To a mixed solution of 4-(benzyloxycarbonylamino)-1,1-dioxy-N-(4-pyridyl)thiochromane-7-carboxamide (2.00 g) obtained in Starting Material Synthetic Example 7 in methanol (100 ml)-dioxane (50 ml) was added 4N hydrochloric acid dioxane solution (2 ml) and 10% palladium carbon (2.00 g) and hydrogenation was carried out at room temperature for 24 hr. The reaction mixture was passed through celite and the solvent was evaporated under reduced pressure. The obtained residue was recrystallized from methanol-ethyl acetate to give crude crystals (1.03 g) of the objective 4-amino-N-(4-pyridyl)thiochromane-7-carboxamide 1,1-dioxide. The crystals were further purified as follows. The crude crystals (1.00 g) were dissolved in methanol (30 ml) and water (20 ml), and ethyl acetate (about 100 ml) was added. The mixture was stood overnight at 0° C. and the precipitated crystals were collected by filtration and dried to give the objective 4-amino-N-(4-pyridyl)thiochromane-7-carboxamide 1,1-dioxide 1HCl 2H$_2$O (788 mg) as colorless crystals.

melting point: >230° C. (decomposition).

$^1$H-NMR(400 MHz, DMSO-d$_6$) δ=2.55–2.65(m, 1H), 2.75–2.85(m, 1H), 3.75–3.80(m, 1H), 3.80–3.92(m, AH), 4.89(t, J=5 Hz, 1H), 8.08(d, J=8 Hz, 1H), 8.11(d, J=5 Hz, 2H), 8.42(d, J=8 Hz, 1H), 8.49(s, 1H), 8.65(d, J=5 Hz, 2H), 9.06(br.s, 3H), 11.49(s, 1H).

EXAMPLE 2

4-amino-N-(4-pyridyl)thiochromane-7-carboxamide 2HCl

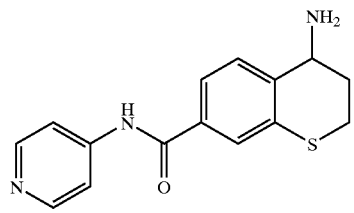

To a solution of 4-(benzyloxycarbonylamino)-N-(4-pyridyl)thiochromane-7-carboxamide (1.20 g) obtained in Starting Material Synthetic Example 9 in trifluoroacetic acid (20 ml) were added methanesulfonic acid (5 ml) and thioanisole (2 ml) under ice-cooling. The mixture was stirred at room temperature for 30 min. Water (200 ml) was added to the reaction mixture and the aqueous layer was washed with diethyl ether. 1N Sodium hydroxide was added to this aqueous layer until the pH became 12 and the mixture was extracted with ethyl acetate. The obtained organic layer was washed with water and saturated brine, and dried over magnesium sulfate. The dehydrated solvent was evaporated under reduced pressure and the obtained residue was recrystallized from methanol-ethyl acetate to give crude crystals of 4-amino-N-(4-pyridyl)thiochromane-7-carboxamide. The crude crystals were dissolved in methanol (30 ml) and 4N hydrochloric acid dioxane solution (923 µl) was added. The mixture was stirred at room temperature for 30 min and an insoluble component was removed. The resulting solution was subjected to recrystallization from water-methanol-ethyl acetate-isopropyl alcohol. The precipitated crystals were collected by filtration and dried to give the objective 4-amino-N-(4-pyridyl)thiochromane-7-carboxamide 2HCl (261 mg) as colorless crystals.

melting point: >280° C. (decomposition).

$^1$H-NMR(400 MHz, DMSO-d$_6$) δ=2.15–2.30(m, 1H), 2.30–2.55(m, 1H), 3.10–3.20(m, 1H), 3.20–3.30(m, 1H), 4.62(br.s, 1H), 7.73(d, J=8 Hz, 1H), 7.82(d, J=8 Hz, 1H), 7.88(s, 1H), 8.38(d, J=7 Hz, 2H), 8.75(d, J=7 Hz, 2H), 8.82 (br.s, 3H), 11.75(s, 1H).

EXAMPLE 3

5-amino-N-(4-pyridyl)-5,6,7,8-tetrahydronaphthalene-2-carboxamide 2HCl 1/4 H$_2$O

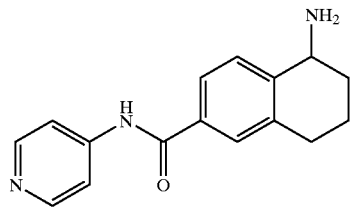

By a similar reaction operation as in Example 1 using 5-(benzyloxycarbonylamino)-N-(4-pyridyl)-5,6,7,8-tetrahydronaphthalene-2-carboxamide (500 mg) obtained in Starting Material Synthetic Example 15 and 10% palladium carbon (250 mg), the objective 5-amino-N-(4-pyridyl)-5,6,7,8-tetrahydronaphthalene-2-carboxamide 2HCl 1/4H$_2$O (298 mg) was obtained as colorless crystals.

melting point: >280° C. (decomposition).

$^1$H-NMR(400 MHz, DMSO-d$_6$) δ=1.75–1.80(m, 1H), 1.93–2.00(m, 2H), 2.00–2.15(m, 1H), 2.75–2.95(m, 2H), 4.50(d, J=5 Hz, 1H), 7.80(d, J=8 Hz, 1H), 7.96(s, 1H), 7.98(d, J=8 Hz, 1H), 8.45(d, J=7 Hz, 2H), 8.72(br.s, 3H), 8.75(d, J=7 Hz, 2H), 11.89(s, 1H).

EXAMPLE 4

5-amino-N-(4-pyridyl)-2,3,4,5-tetrahydro-1-benzothiepine-8-carboxamide 1,1-dioxide 2HCl 1H$_2$O

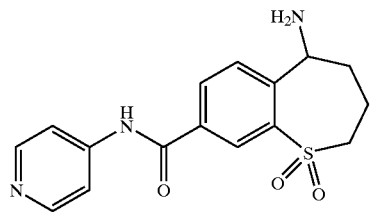

By a similar reaction operation as in Example 1 using 5-(benzyloxycarbonylamino)-1,1-dioxy-N-(4-pyridyl)-2,3, 4,5-tetrahydro-1-benzothiepine-8-carboxamide (1.50 g) obtained in Starting Material Synthetic Example 24 and 10% palladium carbon (500 mg), the objective 5-amino-N-(4-pyridyl)-2,3,4,5-tetrahydro-1-benzothiepine-8-carboxamide 1,1-dioxide 2HCl 1H$_2$O (1.21 g) was obtained as colorless crystals.

melting point: 262–265° C. (decomposition).

$^1$H-NMR(400 MHz, DMSO-d$_6$) δ=1.70–1.80(m, 2H), 2.10–2.35(m, 3H), 3.50–3.75(m, 2H), 5.07(br.s, 1H), 7.80(d, J=8 Hz, 1H), 8.43(d, J=8 Hz, 2H), 8.56(s, 1H), 8.65(d, J=8 Hz, 1H), 8.79(d, J=8 Hz, 2H), 9.17(br.s, 3H), 12.18(s, 1H).

EXAMPLE 5

4-amino-N-(4-pyridyl)chromane-7-carboxamide 2HCl 1/2 H$_2$O

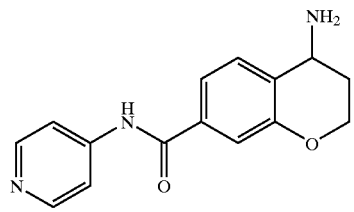

By a similar reaction operation as in Example 1 using 4-(benzyloxycarbonylamino)-N-(4-pyridyl)chromane-7-carboxamide (2.0 g) obtained in Starting Material Synthetic Example 30 and 10% palladium carbon (1.00 g), the objective 4-amino-N-(4-pyridyl)chromane-7-carboxamide 2HCl 1/2 H$_2$O (0.63 g) was obtained as colorless crystals.

melting point: >280° C.

$^1$H-NMR(400 MHz, DMSO-d$_6$) δ=2.15–2.25(m, 1H), 2.25–2.35(m, 1H), 4.1–4.2(m, 1H), 4.3–4.4(m, 1H), 4.55–4.65(m, 1H), 7.57(s, 1H), 7.67(d, J=8 Hz, 1H), 7.79(d, J=7 Hz, 1H), 8.32(d, J=6 Hz, 2H), 8.72(d, J=6 Hz, 2H), 8.91(br.s, 3H), 11.58(br.s, 1H).

EXAMPLE 6

(R)-4-amino-N-(4-pyridyl)thiochromane-7-carboxamide 1,1-dioxide 2HCl 5/3 H$_2$O

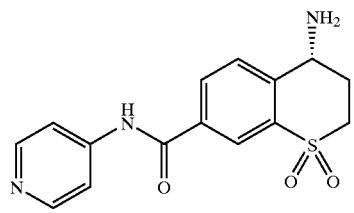

To a mixed solution of (R)-4-(benzyloxycarbonylamino)-1,1-dioxy-N-(4-pyridyl)thiochromane-7-carboxamide. (1.20 g) obtained in Starting Material Synthetic Example 39 in methanol (100 ml)-N,N-dimethylformamide (100 ml) were added 4N hydrochloric acid dioxane solution (2 ml) and 10% palladium carbon (600 mg) and the mixture was hydrogenated (30 pressure) at room temperature for 7 hr. The reaction mixture was passed through Celite and the solvent was evaporated under reduced pressure. The obtained residue was recrystallized twice from water-methanol-ethyl acetate to give the objective (R)-4-amino-N-(4-pyridyl)thiochromane-7-carboxamide 1,1-dioxide 2HCl 5/3 H$_2$O (763 mg) was obtained as colorless crystals.

melting point: >275° C. (decomposition).

optical rotation [α]$_D^{23}$=−3.7 (c=1.00, H$_2$O).

$^1$H-NMR(400 MHz, DMSO-d$_6$) δ=2.55–2.70(m, 1H), 2.75–2.85(m, 1H), 3.75–3.85(m, 1H), 3.85–3.95(m, 1H), 4.89(br.s, 1H), 8.10–8.15(m, 1H), 8.30–8.45(m, 2H), 8.51(br.s, 2H), 8.79(d, J=8 Hz, 2H), 9.14(br.s, 3H), 11.98(br.s, 1H).

EXAMPLE 7

(R)-4-amino-N-(4-pyridyl)thiochromane-7-carboxamide 1,1-dioxide 2HCl 3/2 H$_2$O

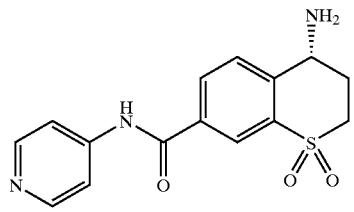

To a mixed solution of (R)-4-(benzyloxycarbonylamino)-1,1-dioxy-N-(4-pyridyl)thiochromane-7-carboxamide (2.50 g) obtained in Starting Material Synthetic Example 40 in methanol (50 ml)-N,N-dimethylformamide (80 ml) were added 4N hydrochloric acid dioxane solution (1 ml) and 10% palladium carbon (2.00 g) and the mixture was hydrogenated (30 pressure) at room temperature for 7 hr. The reaction mixture was passed through Celite and the solvent was evaporated under reduced pressure. The obtained residue was recrystallized twice from water-methanol-ethyl acetate to give the objective (R)-4-amino-N-(4-pyridyl)thiochromane-7-carboxamide 1,1-dioxide 2HCl 3/2 H$_2$O (879 mg) as colorless crystals.

melting point: >250° C. (decomposition).

optical rotation [α]$_D^{23}$=−7.2 (c=0.98, H$_2$O).

$^1$H-NMR(400 MHz, DMSO-d$_6$) δ=2.65–2.75(m, 1H), 2.75–2.85(m, 1H), 3.75–3.85(m, 1H), 3.90–4.00(m, 1H), 4.91(br.s, 1H), 8.13(d, J=8 Hz, 1H), 8.40(d, J=7 Hz, 2H), 8.50(d, J=8 Hz, 1H), 8.51(s, 1H), 8.80(d, J=7 Hz, 2H), 9.16(br.s, 3H), 12.01(s, 1H).

EXAMPLE 8

(S)-4-amino-N-(4-pyridyl)thiochromane-7-carboxamide 1,1-dioxide 2HCl 5/3 H$_2$O

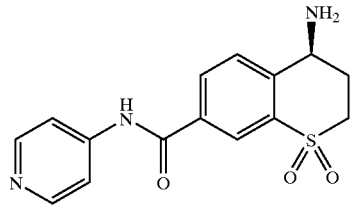

By a similar reaction operation as in Example 6 using (S)-4-(benzyloxycarbonylamino)-1,1-dioxy-N-(4-pyridyl)thiochromane-7-carboxamide (675 mg) obtained in Starting Material Synthetic Example 49 and 10% palladium carbon (600 mg), the objective (S)-4-amino-N-(4-pyridyl)thiochromane-7-carboxamide 1,1-dioxide 2HCl 5/3 H$_2$O (517 mg) was obtained as colorless crystals.

melting point: >275° C. (decomposition).

optical rotation $[\alpha]_D^{23}$=+3.4 (c=0.95, H$_2$O).

$^1$H-NMR(400 MHz, DMSO-d$_6$) δ=2.55–2.70(m, 1H), 2.75–2.85(m, 1H), 3.75–3.85(m, 1H), 3.85–3.95(m, 1H), 4.89(br.s, 1H), 8.10–8.15(m, 1H), 8.30–8.45(m, 2H), 8.51 (br.s, 2H), 8.79(d, J=8 Hz, 2H), 9.14(br.s, 3H), 11.98(br.s, 1H).

EXAMPLE 9

(S)-4-amino-N-(4-pyridyl)thiochromane-7-carboxamide 1,1-dioxide 2HCl 3/2 H$_2$O

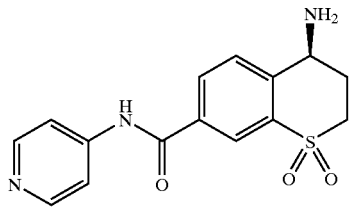

By a similar reaction operation as in Example 7 using (S)-4-(benzyloxycarbonylamino)-1,1-dioxy-N-(4-pyridyl) thiochromane-7-carboxamide (900 mg) obtained in Starting Material Synthetic Example 50 and 10% palladium carbon (1.00 g), the objective (S)-4-amino-N-(4-pyridyl) thiochromane-7-carboxamide 1,1-dioxide 2HCl 3/2 H$_2$O (256 mg) was obtained as colorless crystals.

melting point: >250° C. (decomposition).

optical rotation $[\alpha]_D^{23}$=+7.3 (c=0.31, H$_2$O).

$^1$H-NMR(400 MHz, DMSO-d$_6$) δ=2.65–2.75(m, 1H), 2.75–2.85(m, 1H), 3.75–3.85(m, 1H), 3.90–4.00(m, 1H), 4.91(br.s, 1H), 8.13(d, J=8 Hz, 1H), 8.40(d, J=7 Hz, 2H), 8.50(d, J=8 Hz, 1H), 8.51(s, 1H), 8.80(d, J=7 Hz, 2H), 9.16(br.s, 3H), 12.01(s, 1H).

EXAMPLE 10

(S)-4-amino-N-(4-pyridyl)thiochromane-7-carboxamide 2HCl 4/5H$_2$O

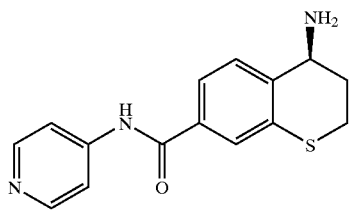

To (S)-4-(tert-butoxycarbonylamino)-N-(4-pyridyl) thiochromane-7-carboxamide (833 mg) obtained in Starting Material Synthetic Example 53 was added 4N dioxane solution (30 ml), and the mixture was stirred at room temperature for 2 hr. Ethyl acetate (200 ml) was added to the reaction mixture and the mixture was stood at 0° C. for 30 min and the precipitated crystals were collected by filtration. The obtained crystals were recrystallized from water-methanol-ethyl acetate to give the objective (S)-4-amino-N-(4-pyridyl)thiochromane-7-carboxamide 2HCl 4/5 H$_2$O (753 mg) as colorless crystals.

melting point: >260° C. (decomposition).

optical rotation $[\alpha]_D^{23}$=−60.6 (c=1.0, H$_2$O).

$^1$H-NMR(400 MHz, DMSO-d$_6$) δ=2.20–2.35(m, 1H), 2.40–2.55(m, 1H), 3.10–3.20(m, 1H), 3.20–3.30(m, 1H), 4.63(br.s, 1H), 7.76(d, J=8 Hz, 1H), 7.84(d, J=8 Hz, 1H), 7.90(s, 1H), 8.41(d, J=7 Hz, 2H), 8.77(d, J=7 Hz, 2H), 8.86(br.s, 3H), 11.80(s, 1H).

EXAMPLE 11

(S)-4-amino-N-(1H-pyrazolo[3,4-b]pyridin-4-yl) thiochromane-7-carboxamide 2HCl 5/3 H$_2$O

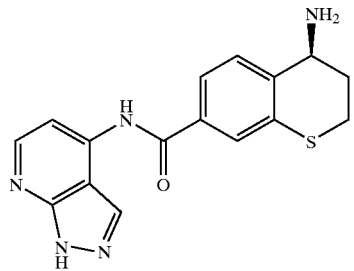

By a similar reaction operation as in Example 10 using (S)-4-(tert-butoxycarbonylamino)-N-(1-triphenylmethylpyrazolo[3,4-b]pyridin-4-yl)thiochromane-7-carboxamide (787 mg) obtained in Starting Material Synthetic Example 54 and 4N dioxane solution (25 ml), the objective (S)-4-amino-N-(1H-pyrazolo[3,4-b]pyridin-4-yl) thiochromane-7-carboxamide 2HCl 5/3 H$_2$O (348 mg) was obtained as pale yellow crystals.

melting point: >260° C. (decomposition).

optical rotation $[\alpha]_D^{23}$=−56.9 (c=1.0, H$_2$O).

$^1$H-NMR(400 MHz, DMSO-d$_6$) δ=2.26(t, J=11 Hz, 1H), 2.50–2.60(m, 1H), 3.16(br.s, 1H), 3.31(t, J=11 Hz, 1H), 4.63(br.s, 1H), 7.77(br.s, 2H), 7.85(s, 1H), 7.88(br.s, 1H), 8.60(br.s, 1H), 8.77(br.s, 1H), 8.90(br.s, 3H), 11.40(br.s, 1H).

EXAMPLE 12

(S)-4-amino-N-(1H-pyrazolo[3,4-b]pyridin-4-yl) thiochromane-7-carboxamide 1,1-dioxide 2HCl 2H$_2$O

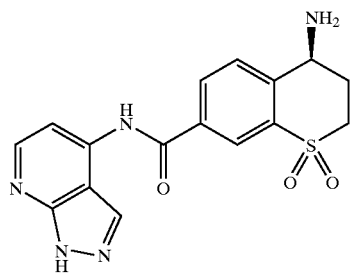

By a similar reaction operation as in Example 10 using (S)-4-(tert-butoxycarbonylamino)-1,1-dioxy-N-(1-triphenylmethylpyrazolo[3,4-b]pyridin-4-yl)thiochromane-7-carboxamide (630 mg) obtained in Starting Material Synthetic Example 56 and 4N dioxane solution (20 ml), the objective (S)-4-amino-N-(1H-pyrazolo[3,4-b]pyridin-4-yl) thiochromane-7-carboxamide 1,1-dioxide 2HCl 2H$_2$O (289 mg) was obtained as pale yellow crystals.

melting point: >265° C. (decomposition).

optical rotation $[\alpha]_D^{23}$=+4.14 (c=1.0, H$_2$O).

$^1$H-NMR(400 MHz, DMSO-d$_6$) δ=2.67(br.s, 1H), 2.80 (br.s, 1H), 3.70–4.00(m, 2H), 4.90(br.s, 1H), 7.79(br.s, 1H), 8.11(m, 1H), 8.42(d, J=8 Hz, 1H), 8.47(s, 1H), 8.50–8.75(m, 2H), 9.17(br.s, 3H), 11.56(br.s, 1H).

EXAMPLE 13

(S)-4-amino-N-(1H-pyrrolo[2,3-b]pyridin-4-yl)thiochromane-7-carboxamide 2HBr 4/5H$_2$O

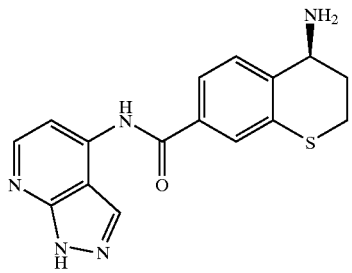

To (S)-4-(benzyloxycarbonylamino)-N-(1H-pyrrolo[2,3-b]pyridin-4-yl)thiochromane-7-carboxamide (500 mg) obtained in Starting Material Synthetic Example 60 was added 30% hydrobromic acid acetic acid solution (20 ml) and the mixture was stirred at room temperature for 4 hr. Ethyl acetate (200 ml) was added to the reaction mixture and stood at 0° C. for 30 min. The precipitated crystals were collected by filtration and the obtained crystals were recrystallized from water-methanol-ethyl acetate to give the objective (S)-4-amino-N-(1H-pyrrolo[2,3-b]pyridin-4-yl)thiochromane-7-carboxamide 2HBr 4/5H$_2$O (316 mg) as colorless crystals.

melting point: >250° C. (decomposition).

optical rotation $[\alpha]_D^{23}$=48.5 (c=0.5, H$_2$O).

$^1$H-NMR(400 MHz, DMSO-d$_6$) δ=2.24(br.t, J=13 Hz, 1H), 2.30–2.50(m, 1H), 3.05–3.30(m, 2H), 4.68(br.s, 1H), 7.15(s, 1H), 7.61(s, 1H), 7.65(d, J=8 Hz, 1H), 7.74(d, J=8 Hz, 1H), 7.81(s, 1H), 8.07(d, J=7 Hz, 1H), 8.41(d, J=6 Hz, 1H), 8.52(br.s, 3H), 11.06(s, 1H), 12.56(br.s, 1H).

EXAMPLE 14

(S)-4-amino-N-(1H-pyrrolo[2,3-b]pyridin-4-yl)thiochromane-7-carboxamide 1,1-dioxide 2HBr 2H$_2$O

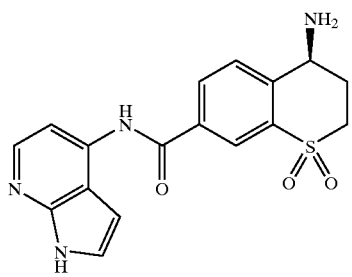

By a similar reaction operation as in Example 13 using (S)-4-(benzyloxycarbonylamino)-1,1-dioxy-N-(1H-pyrrolo[2,3-b]pyridin-4-yl)thiochromane-7-carboxamide (500 mg) obtained in Starting Material Synthetic Example 62 and 30% hydrobromic acid acetic acid solution (20 ml), the objective (S)-4-amino-N-(1H-pyrrolo[2,3-b]pyridin-4-yl)thiochromane-7-carboxamide 1,1-dioxide 2HBr 2H$_2$O (325 mg) was obtained as colorless crystals.

melting point: >240° C. (decomposition).

optical rotation $[\alpha]_D^{23}$=+$^{3.9}$ (c=1.0, H$_2$O).

$^1$H-NMR(400 MHz, DMSO-d$_6$) δ=2.60–2.70(m, 1H), 2.70–2.80(m, 1H), 3.75–3.85(m, 2H), 4.97(br.s, 1H), 7.13(s, 1H), 7.64(s, 1H), 7.95–8.08(m, 2H), 8.35–8.45(m, 2H), 8.49(s, 1H), 8.77(br.s, 3H), 11.35(br.s, 1H), 12.58(br.s, 1H).

EXAMPLE 15

4-amino-8-methyl-N-(4-pyridyl)thiochromane-7-carboxamide 2HCl 1H$_2$O

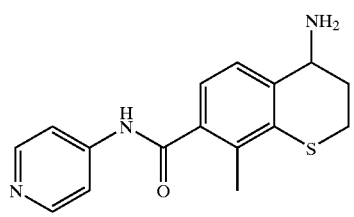

By a similar reaction operation as in Example 10 using 4-(tert-butoxycarbonylamino)-8-methyl-N-(4-pyridyl)thiochromane-7-carboxamide (400 mg) obtained in Starting Material Synthetic Example 68 and 4N hydrochloric acid dioxane solution (10 ml), the objective 4-amino-8-methyl-N-(4-pyridyl)thiochromane-7-carboxamide 2HCl 1H$_2$O (311 mg) was obtained as colorless crystals.

melting point: >250° C. (decomposition).

$^1$H-NMR(400 MHz, DMSO-d$_6$) δ=2.15–2.20(m, 1H), 2.24(s, 3H), 2.50–2.60(m, 1H), 3.15–3.30(m, 2H), 4.61(br.s, 1H), 7.34(d, J=7 Hz, 1H), 7.53(d, J=7 Hz, 1H), 8.22(d, J=6 Hz, 2H), 8.75(d, J=6 Hz, 2H), 8.79(s, 3H), 11.87(br.s, 1H).

EXAMPLE 16

(S)-4-amino-8-methyl-N-(4-pyridyl)thiochromane-7-carboxamide 2HCl

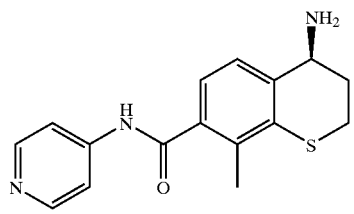

By a similar reaction operation as in Example 10 using (S)-4-(tert-butoxycarbonylamino)-8-methyl-N-(4-pyridyl)thiochromane-7-carboxamide (1.87 g) obtained in Starting Material Synthetic Example 74 and 4N hydrochloric acid dioxane solution (50 ml), the objective (S)-4-amino-8-methyl-N-(4-pyridyl)thiochromane-7-carboxamide 2HCl (1.44 g) was obtained as colorless crystals.

melting point: >250° C. (decomposition).

optical rotation $[\alpha]_D^{23}$=−47.2 (c=1.0, H$_2$O).

$^1$H-NMR(400 MHz, DMSO-d$_6$) δ=2.15–2.20(m, 1H), 2.25(s, 3H), 2.50–2.60(m, 1H), 3.15–3.30(m, 2H), 4.61(br.s, 1H), 7.36(d, J=8 Hz, 1H), 7.57(d, J=8 Hz, 1H), 8.26(d, J=7 Hz, 2H), 8.77(d, J=7 Hz, 2H), 8.87(s, 3H), 11.95(s, 1H).

EXAMPLE 17

(S)-4-amino-8-methyl-N-(4-pyridyl)thiochromane-7-carboxamide 1,1-dioxide 2HCl 3/2H$_2$O

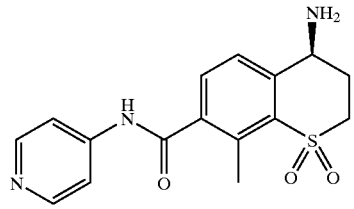

By a similar reaction operation as in Example 10 using (S)-4-(tert-butoxycarbonylamino)-8-methyl-1,1-dioxy-N-(4-pyridyl)thiochromane-7-carboxamide (733 mg) obtained in Starting Material Synthetic Example 76 and 4N hydrochloric acid dioxane solution (30 ml), the objective (S)-4-amino-8-methyl-N-(4-pyridyl)thiochromane-7-carboxamide 1,1-dioxide 2HCl 3/2 H$_2$O (489 mg) was obtained as colorless crystals.

melting point: >280° C. (decomposition).

optical rotation $[\alpha]_D^{23}$=+10.8 (c=1.0, H$_2$O).

$^1$H-NMR(400 MHz, DMSO-d$_6$) δ=2.51(s, 3H), 2.55–2.70 (m, 2H), 3.76(br.t, J=10 Hz, 1H), 3.97(br.t, J=10 Hz, 1H), 4.85(br.s, 1H), 7.89(s, 2H), 8.25(d, J=7 Hz, 2H), 8.79(d, J=7 Hz, 2H), 9.18(s, 3H), 12.15(s, 1H).

EXAMPLE 18

(S)-4-amino-8-methyl-N-(1H-pyrazolo[3,4-b]pyridin-4-yl)thiochromane-7-carboxamide 1,1-dioxide 2HCl 2H$_2$O

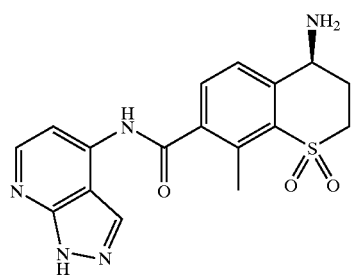

By a similar reaction operation as in Example 10 using (S)-4-(tert-butoxycarbonylamino)-8-methyl-1,1-dioxy-N-(1-triphenylmethylpyrazolo[3,4-b]pyridin-4-yl)thiochromane-7-carboxamide (140 mg) obtained in Starting Material Synthetic Example 77 and 4N dioxane solution (10 ml), the objective (S)-4-amino-8-methyl-N-(1H-pyrazolo[3,4-b]pyridin-4-yl)thiochromane-7-carboxamide 1,1-dioxide 2HCl 2H$_2$O (72 mg) was obtained as pale yellow crystals.

melting point: >250° C. (decomposition).

$^1$H-NMR(400 MHz, DMSO-d$_6$) δ=2.50–2.70(m, 2H), 2.69(s, 3H), 3.50–3.85(m, 2H), 4.85(br.s, 1H), 7.80–8.00(m, 3H), 8.56(br.s, 2H), 9.15(br.s, 3H), 11.63(br.s, 1H).

EXAMPLE 19

4-amino-6-methyl-N-(4-pyridyl)thiochromane-7-carboxamide 2HCl 3/2 H$_2$O

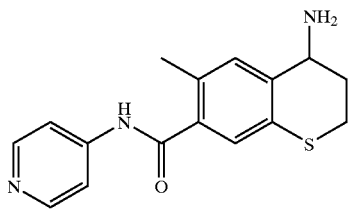

By a similar reaction operation as in Example 10 using 4-(tert-butoxycarbonylamino)-6-methyl-N-(4-pyridyl)thiochromane-7-carboxamide (800 mg) obtained in Starting Material Synthetic Example 83 and 4N hydrochloric acid dioxane solution (20 ml), the objective 4-amino-6-methyl-N-(4-pyridyl)thiochromane-7-carboxamide 2HCl 3/2 H$_2$O (706 mg) was obtained as pale yellow crystals.

melting point: >260° C. (decomposition).

$^1$H-NMR(400 MHz, DMSO-d$_6$) δ=2.21(br.t, J=8 Hz, 1H), 2.35(s, 3H), 2.40–2.55(m, 1H), 3.05–3.15(m, 1H), 3.25–3.35(m, 1H), 4.56(br.s, 1H), 7.46(s, 1H), 7.56(br.s, 1H), 8.25(d, J=7 Hz, 2H), 8.76(d, J=7 Hz, 2H), 8.83(br.s, 3H), 11.81(br.s, 1H).

EXAMPLE 20

4-amino-6-methyl-N-(4-pyridyl)thiochromane-7-carboxamide 1,1-dioxide 2HCl 2H$_2$O

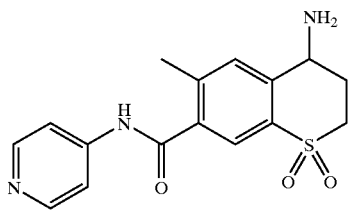

By a similar reaction operation as in Example 10 using 4-(tert-butoxycarbonylamino)-6-methyl-1,1-dioxy-N-(4-pyridyl)thiochromane-7-carboxamide (650 mg) obtained in Starting Material Synthetic Example 85 and 4N hydrochloric acid dioxane solution (10 ml), the objective 4-amino-6-methyl-N-(4-pyridyl)thiochromane-7-carboxamide 1,1-dioxide 2HCl 2H$_2$O (515 mg) was obtained as pale yellow crystals.

melting point: >280° C. (decomposition).

$^1$H-NMR(400 MHz, DMSO-d$_6$) δ=2.51(s, 3H), 2.65–2.85 (m, 2H), 3.73(br.t, J=8 Hz, 1H), 3.97(br.t, J=8 Hz, 1H), 4.84(br.s, 1H), 8.00(s, 1H), 8.09(s, 1H), 8.26(d, J=7 Hz, 2H), 8.79(d, J=7 Hz, 2H), 9.26(br.s, 3H), 12.12(br.s, 1H).

EXAMPLE 21

(S)-4-amino-6-methyl-N-(4-pyridyl)thiochromane-7-carboxamide 2HCl 1/5H₂O

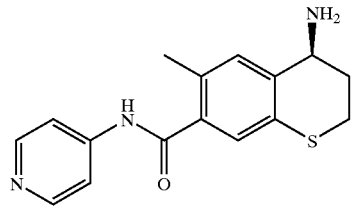

By a similar reaction operation as in Example 10 using (S)-4-(tert-butoxycarbonylamino)-6-methyl-N-(4-pyridyl)thiochromane-7-carboxamide (1.00 g) obtained in Starting Material Synthetic Example 91 and 4N hydrochloric acid dioxane solution (20 ml), the objective (S)-4-amino-6-methyl-N-(4-pyridyl)thiochromane-7-carboxamide 2HCl 1/5H₂O (720 mg) was obtained as pale yellow crystals.

melting point: >260° C. (decomposition).

optical rotation $[\alpha]_D^{23}$=−52.7 (c=1.0, H₂O).

¹H-NMR(400 MHz, DMSO-d₆) δ=2.20(br.t, J=8 Hz, 1H), 2.34(s, 3H), 2.40–2.50(m, 1H), 3.05–3.15(m, 1H), 3.20–3.40(m, 1H), 4.54(br.s, 1H), 7.44(s, 1H), 7.56(s, 1H), 8.23(d, J=7 Hz, 2H), 8.74(d, J=7 Hz, 2H), 8.80(br.s, 3H), 11.78(br.s, 1H).

EXAMPLE 22

(S)-4-amino-6-methyl-N-(4-pyridyl)thiochromane-7-carboxamide 1,1-dioxide 2HCl 5/4 H₂O

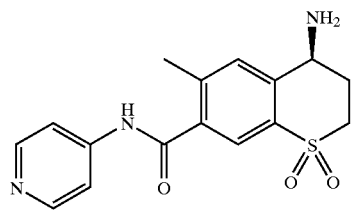

By a similar reaction operation as in Example 10 using (S)-4-(tert-butoxycarbonylamino)-6-methyl-1,1-dioxy-N-(4-pyridyl)thiochromane-7-carboxamide (696 mg) obtained in Starting Material Synthetic Example 93 and 4N hydrochloric acid dioxane solution (20 ml), the objective (S)-4-amino-6-methyl-N-(4-pyridyl)thiochromane-7-carboxamide 1,1-dioxide 2HCl 5/4 H₂O (379 mg) was obtained as colorless crystals.

melting point: >280° C. (decomposition).

optical rotation $[\alpha]_D^{23}$=+3.21 (c=1.0, H₂O).

¹H-NMR(400 MHz, DMSO-d₆) δ=2.50(s, 3H), 2.60–2.70 (m, 1H), 2.70–2.80(m, 1H), 3.65–3.75(m, 1H), 3.88–3.98 (m, 1H), 4.83(br.s, 1H), 7.94(s, 1H), 8.09(s, 1H), 8.22(d, J=7 Hz, 2H), 8.77(d, J=7 Hz, 2H), 9.13(br.s, 3H), 12.01(s, 1H).

EXAMPLE 23

(S)-4-amino-6-methyl-N-(1H-pyrazolo[3,4-b]pyridin-4-yl)thiochromane-7-carboxamide 2HCl 1H₂O

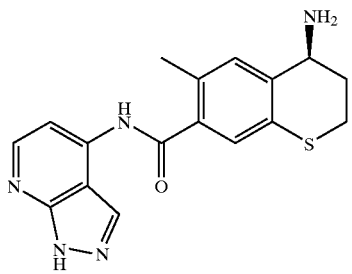

By a similar reaction operation as in Example 10 using (S)-4-(tert-butoxycarbonylamino)-6-methyl-N-(1-triphenylmethylpyrazolo[3,4-b]pyridin-4-yl)thiochromane-7-carboxamide (700 mg) obtained in Starting Material Synthetic Example 94 and 4N dioxane solution (20 ml), the objective (S)-4-amino-6-methyl-N-(1H-pyrazolo[3,4-b]pyridin-4-yl)thiochromane-7-carboxamide 2HCl 1H₂O (308 mg) was obtained as pale yellow crystals.

melting point: >260° C. (decomposition).

optical rotation $[\alpha]_D^{23}$=−54.5 (c=1.0, H₂O).

¹H-NMR(400 MHz, DMSO-d₆) δ=2.19(br.t, J=10 Hz, 1H), 2.34(s, 3H), 2.40–2.50(m, 1H), 3.10(br.t, J=10 Hz, 1H), 3.29(t, J=10 Hz, 1H), 4.55(br.s, 1H), 7.40(s, 1H), 7.54(s, 1H), 7.92(d, J=4 Hz, 1H), 8.54(br.s, 1H), 8.66(br.s, 1H), 8.78(br.s, 3H), 11.43(br.s, 1H).

EXAMPLE 24

(S)-4-amino-6-methyl-N-(1H-pyrazolo[3,4-b]pyridin-4-yl)thiochromane-7-carboxamide 1,1-dioxide 2HCl 2H₂O

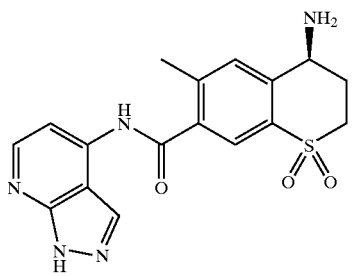

By a similar reaction operation as in Example 10 using (S)-4-(tert-butoxycarbonylamino)-6-methyl-1,1-dioxy-N-(1-triphenylmethylpyrazolo[3,4-b]pyridin-4-yl)thiochromane-7-carboxamide (610 mg) obtained in Starting Material Synthetic Example 95 and 4N dioxane solution (20 ml), the objective (S)-4-amino-6-methyl-N-(1H-pyrazolo[3,4-b]pyridin-4-yl)thiochromane-7-carboxamide 1,1-dioxide 2HCl 2H₂O (330 mg) was obtained as pale yellow crystals.

melting point: >260° C. (decomposition).

optical rotation $[\alpha]_D^{23}$=+30.8 (c=1.0, H₂O).

¹H-NMR(400 MHz, DMSO-d₆) δ=2.50(s, 3H), 2.67(br.s, 1H), 2.78(br.s, 1H), 3.60–3.80(m, 2H), 4.84(br.s, 1H), 7.85–7.95(m, 2H), 8.04(s, 1H), 8.55(br.s, 2H), 9.10(br.s, 3H), 11.58(br.s, 1H).

EXAMPLE 25

(S)-4-amino-6-methyl-N-(1H-pyrrolo[2,3-b]pyridin-4-yl)thiochromane-7-carboxamide 1,1-dioxide 2HBr 3H$_2$O

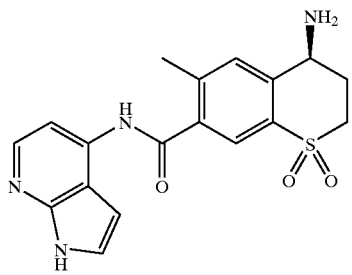

By a similar reaction operation as in Example 13 using (S)-4-(benzyloxycarbonylamino)-6-methyl-1,1-dioxy-N-(1H-pyrrolo[2,3-b]pyridin-4-yl)thiochromane-7-carboxamide (400 mg) obtained in Starting Material Synthetic Example 100 and 30% hydrobromic acid acetic acid solution (20 ml), the objective (S)-4-amino-6-methyl-N-(1H-pyrrolo[2,3-b]pyridin-4-yl)thiochromane-7-carboxamide 1,1-dioxide 2HBr 3H$_2$O (298 mg) was obtained as colorless crystals.

melting point: >240° C. (decomposition).

$^1$H-NMR(400 MHz, DMSO-d$_6$) δ=2.50(s, 3H), 2.55–2.65 (m, 1H), 2.70–2.80(m, 1H), 3.75(t, J=9 Hz, 1H), 3.84(t, J=9 Hz, 1H), 4.90(br.s, 1H), 7.11(br.s, 1H), 7.60(s, 1H), 7.81(d, J=4 Hz, 1H), 8.07(s, 1H), 8.20(br.s, 1H), 8.42(br.s, 1H), 8.72(br.s, 3H), 11.46(br.s, 1H), 12.54(br.s, 1H).

EXAMPLE 26

4-amino-6-chloro-N-(4-pyridyl)thiochromane-7-carboxamide 2HCl 1/3 H$_2$O

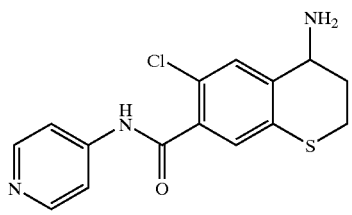

By a similar reaction operation as in Example 10 using 4-(tert-butoxycarbonylamino)-6-chloro-N-(4-pyridyl)thiochromane-7-carboxamide (250 mg) obtained in Starting Material Synthetic Example 106 and 4N hydrochloric acid dioxane solution (15 ml), the objective 4-amino-6-chloro-N-(4-pyridyl)thiochromane-7-carboxamide 2HCl 1/3 H$_2$O (157 mg) was obtained as pale yellow crystals.

melting point: >270° C. (decomposition).

$^1$H-NMR(400 MHz, DMSO-d$_6$) δ=2.19(br.t, J=11 Hz, 1H), 2.40–2.50(m, 1H), 3.10–3.15(m, 1H), 3.30(br.t, J=11 Hz, 1H), 4.62(br.s, 1H), 7.58(s, 1H), 7.83(s, 1H), 8.19(d, J=6 Hz, 2H), 8.76(d, J=6 Hz, 2H), 8.90(br.s, 3H), 12.07(s, 1H).

EXAMPLE 27

4-amino-6-chloro-N-(4-pyridyl)thiochromane-7-carboxamide 1,1-dioxide 2HCl

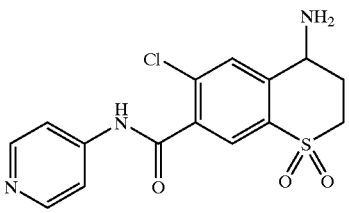

By a similar reaction operation as in Example 10 using 4-(tert-butoxycarbonylamino)-6-chloro-1,1-dioxy-N-(4-pyridyl)thiochromane-7-carboxamide (180 mg) obtained in Starting Material Synthetic Example 108 and 4N hydrochloric acid dioxane solution (20 ml); the objective 4-amino-6-chloro-N-(4-pyridyl)thiochromane-7-carboxamide 1,1-dioxide 2HCl (109 mg) was obtained as colorless crystals.

melting point: >280° C. (decomposition).

$^1$H-NMR(400 MHz, DMSO-d$_6$) δ=2.60–2.70(m, 1H), 2.70–2.80(m, 1H), 3.78(br.t, J=10 Hz, 1H), 3.98(br.t, J=10 Hz, 1H), 4.89(br.s, 1H), 8.16(d, J=7 Hz, 2H), 8.25(s, 1H), 8.28(s, 1H), 8.78(d, J=7 Hz, 2H), 9.20(br.s, 3H), 12.22(s, 1H).

EXAMPLE 28

(S)-4-amino-6-chloro-N-(4-pyridyl)thiochromane-7-carboxamide 2HCl

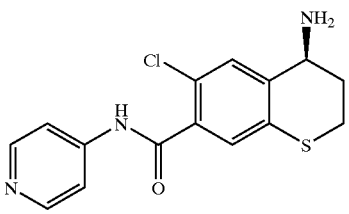

By a similar reaction operation as in Example 10 using (S)-4-(tert-butoxycarbonylamino)-6-chloro-N-(4-pyridyl)thiochromane-7-carboxamide (300 mg) obtained in Starting Material Synthetic Example 114 and 4N hydrochloric acid dioxane solution (20 ml), the objective (S)-4-amino-6-chloro-N-(4-pyridyl)thiochromane-7-carboxamide 2HCl (174 mg) was obtained as pale yellow crystals.

melting point: >270° C. (decomposition).

optical rotation $[\alpha]_D^{23}$=−42.3 (c=0.5, H$_2$O).

$^1$H-NMR(400 MHz, DMSO-d$_6$) δ=2.20(br.t, J=11 Hz, 1H), 2.40–2.50(m, 1H), 3.10–3.18(m, 1H), 3.31(br.t, J=11 Hz, 1H), 4.62(br.s, 1H), 7.58(s, 1H), 7.85(s, 1H), 8.20(d, J=6 Hz, 2H), 8.77(d, J=6 Hz, 2H), 8.95(br.s, 3H), 12.10(s, 1H).

EXAMPLE 29

(S)-4-amino-6-chloro-N-(4-pyridyl)thiochromane-7-carboxamide 1,1-dioxide 2HCl

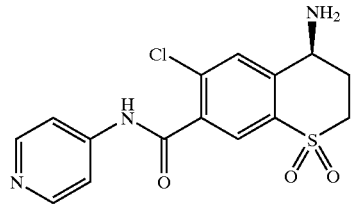

By a similar reaction operation as in Example 10 using (S)-4-(tert-butoxycarbonylamino)-6-chloro-1,1-dioxy-N-(4-pyridyl)thiochromane-7-carboxamide (270 mg) obtained in Starting Material Synthetic Example 116 and 4N hydrochloric acid dioxane solution (20 ml), the objective (S)-4-amino-6-chloro-N-(4-pyridyl)thiochromane-7-carboxamide 1,1-dioxide 2HCl (156 mg) was obtained as colorless crystals.

melting point: >280° C. (decomposition).

optical rotation $[\alpha]_D^{23}$=+11.3 (c=0.5, H$_2$O).

$^1$H-NMR(400 MHz, DMSO-d$_6$) δ=2.60–2.70(m, 1H), 2.70–2.80(m, 1H), 3.80(br.t, J=10 Hz, 1H), 3.97(br.t, J=10 Hz, 1H), 4.89(br.s, 1H), 8.15(d, J=6 Hz, 2H), 8.24(s, 1H), 8.29(s, 1H), 8.77(d, J=6 Hz, 2H), 9.17(br.s, 3H), 12.19(s, 1H).

EXAMPLE 30

(S)-4-amino-6-chloro-N-(1H-pyrazolo[3,4-b]pyridin-4-yl)thiochromane-7-carboxamide 2HCl

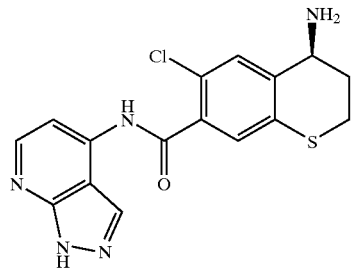

By a similar reaction operation as in Example 10 using (S)-4-(tert-butoxycarbonylamino)-6-chloro-N-(1-triphenylmethylpyrazolo[3,4-b]pyridin-4-yl)thiochromane-7-carboxamide (250 mg) obtained in Starting Material Synthetic Example 117 and 4N dioxane solution (20 ml), the objective (S)-4-amino-6-chloro-N-(1H-pyrazolo[3,4-b]pyridin-4-yl)thiochromane-7-carboxamide 2HCl (111 mg) was obtained as a yellow amorphous solid.

melting point: >240° C. (decomposition).

$^1$H-NMR(400 MHz, DMSO-d$_6$) δ=2.15–2.25(m, 1H), 2.40–2.50(m, 1H), 3.10–3.20(m, 1H), 3.29(br.t, J=11 Hz, 1H), 4.64(br.s, 1H), 7.56(s, 1H), 7.78(s, 1H), 7.87(d, J=4 Hz, 1H), 8.49(br.s, 2H), 8.70–8.90(m, 4H), 11.41(br.s, 1H).

EXAMPLE 31

(S)-4-amino-6-chloro-N-(1H-pyrazolo[3,4-b]pyridin-4-yl)thiochromane-7-carboxamide 1,1-dioxide 2HCl

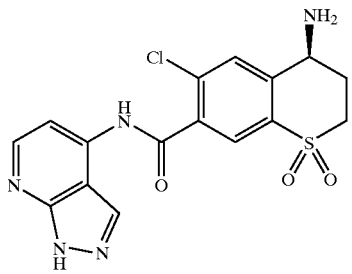

By a similar reaction operation as in Example 10 using (S)-4-(tert-butoxycarbonylamino)-6-chloro-1,1-dioxy-N-(1-triphenylmethylpyrazolo[3,4-b]pyridin-4-yl)thiochromane-7-carboxamide (159 mg) obtained in Starting Material Synthetic Example 118 and 4N dioxane solution (20 ml), the objective (S)-4-amino-6-chloro-N-(1H-pyrazolo[3,4-b]pyridin-4-yl)thiochromane-7-carboxamide 1,1-dioxide 2HCl (54.8 mg) was obtained as a yellow amorphous solid.

melting point: >250° C. (decomposition).

$^1$H-NMR(400 MHz, DMSO-d$_6$) δ=2.60–2.90(m, 2H), 3.78(br.t, J=10 Hz, 1H), 3.99(br.t, J=10 Hz, 1H), 4.91(br.s, 1H), 7.90(d, J=5 Hz, 1H), 8.24(s, 2H), 8.54(br.s, 2H), 9.19(br.s, 4H), 11.72(br.s, 1H).

EXAMPLE 32

(S)-4-amino-6-chloro-N-(1H-pyrrolo[2,3-b]pyridin-4-yl)thiochromane-7-carboxamide 1,1-dioxide 2HBr 3/2 H$_2$O

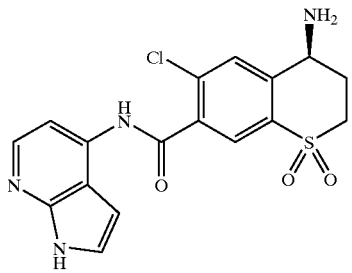

By a similar reaction operation as in Example 13 using (S)-4-(benzyloxycarbonylamino)-6-chloro-1,1-dioxy-N-(1H-pyrrolo[2,3-b]pyridin-4-yl)thiochromane-7-carboxamide (130 mg) obtained in Starting Material Synthetic Example 123 and 30% hydrobromic acid acetic acid solution (15 ml), the objective (S)-4-amino-6-chloro-N-(1H-pyrrolo[2,3-b]pyridin-4-yl)thiochromane-7-carboxamide 1,1-dioxide 2HBr 3/2 H$_2$O (41 mg) was obtained as a colorless amorphous solid.

melting point: >240° C. (decomposition).

$^1$H-NMR(400 MHz, DMSO-d$_6$) δ=2.57–2.67(m, 1H), 2.70–2.80(m, 1H), 3.75–3.90(m, 2H), 4.95(br.s, 1H), 7.03 (br.s, 1H), 7.59(s, 1H), 8.07(d, J=5 Hz, 1H), 8.08–8.20(m, 1H), 8.27(d, J=5 Hz, 1H), 8.72(br.s, 3H), 11.53(br.s, 1H), 12.50(br.s, 1H).

EXAMPLE 33

4-amino-6-methoxy-N-(4-pyridyl)thiochromane-7-carboxamide 2HCl 1H₂O

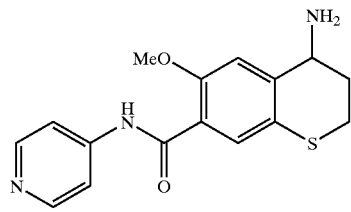

By a similar reaction operation as in Example 10 using 4-(tert-butoxycarbonylamino)-6-methoxy-N-(4-pyridyl)thiochromane-7-carboxamide (350 mg) obtained in Starting Material Synthetic Example 129 and 4N hydrochloric acid dioxane solution (20 ml), the objective 4-amino-6-methoxy-N-(4-pyridyl)thiochromane-7-carboxamide 2HCl 1H₂O (296 mg) was obtained as pale yellow crystals.

melting point: >220° C. (decomposition).

$^1$H-NMR(400 MHz, DMSO-d$_6$) δ=2.20–2.30(m, 1H), 2.40–2.50(m, 1H), 3.00–3.10(m, 1H), 3.15–3.25(m, 1H), 3.90(s, 3H), 4.61(br.s, 1H), 7.39(s, 1H), 7.62(s, 1H), 8.22(d, J=6 Hz, 2H), 8.75(d, J=6 Hz, 2H), 8.94(br.s, 3H), 11.55(s, 1H).

EXAMPLE 34

4-amino-6-methoxy-N-(4-pyridyl)thiochromane-7-carboxamide 1,1-dioxide 2HCl 2H₂O

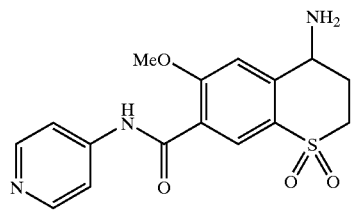

By a similar reaction operation as in Example 10 using 4-(tert-butoxycarbonylamino)-6-methoxy-1,1-dioxy-N-(4-pyridyl)thiochromane-7-carboxamide (130 mg) obtained in Starting Material Synthetic Example 131 and 4N hydrochloric acid dioxane solution (10 ml), the objective 4-amino-6-methoxy-N-(4-pyridyl)thiochromane-7-carboxamide 1,1-dioxide 2HCl 2H₂O (76 mg) was obtained as colorless crystals.

melting point: >240° C. (decomposition).

$^1$H-NMR(400 MHz, DMSO-d$_6$) δ=2.60–2.70(m, 1H), 2.70–2.80(m, 1H), 3.70(br.t, J=11 Hz, 1H), 3.85(br.t, J=11 Hz, 1H), 4.00(s, 3H), 4.86(br.s, 1H), 7.85(br.s, 1H), 8.05(s, 1H), 8.18(d, J=7 Hz, 2H), 8.75(d, J=7 Hz, 2H), 9.15(br.s, 3H), 11.66(br.s, 1H).

EXAMPLE 35

(S)-4-amino-6-methoxy-N-(4-pyridyl)thiochromane-7-carboxamide 2HCl 1H₂O

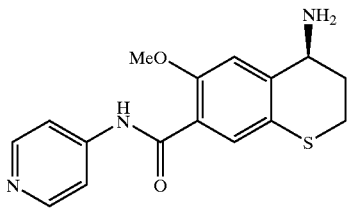

By a similar reaction operation as in Example 10 using (S)-4-(tert-butoxycarbonylamino)-6-methoxy-N-(4-pyridyl)thiochromane-7-carboxamide (250 mg) obtained in Starting Material Synthetic Example 137 and 4N hydrochloric acid dioxane solution (20 ml), the objective (S)-4-amino-6-methoxy-N-(4-pyridyl)thiochromane-7-carboxamide 2HCl 1H₂O (197 mg) was obtained as pale yellow crystals.

melting point: >220° C. (decomposition).

optical rotation $[\alpha]_D^{23}$=−16.5 (c=0.5, H₂O).

$^1$H-NMR(400 MHz, DMSO-d$_6$) δ=2.20–2.30(m, 1H), 2.40–2.50(m, 1H), 3.00–3.10(m, 1H), 3.20–3.30(m, 1H), 3.89(s, 3H), 4.59(br.s, 1H), 7.37(s, 1H), 7.64(br.s, 1H), 8.21(d, J=7 Hz, 2H), 8.74(d, J=7 Hz, 2H), 8.99(br.s, 3H), 11.58(br.s, 1H).

EXAMPLE 36

(S)-4-amino-6-methoxy-N-(4-pyridyl)thiochromane-7-carboxamide 1,1-dioxide 2HCl 2H₂O

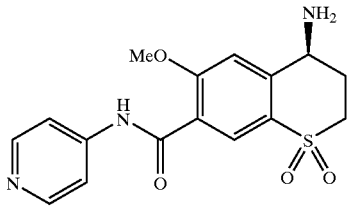

By a similar reaction operation as in Example 10 using (S)-4-(tert-butoxycarbonylamino)-6-methoxy-1,1-dioxy-N-(4-pyridyl)thiochromane-7-carboxamide (130 mg) obtained in Starting Material Synthetic Example 139 and 4N hydrochloric acid dioxane solution (10 ml), the objective (S)-4-amino-6-methoxy-N-(4-pyridyl)thiochromane-7-carboxamide 1,1-dioxide 2HCl 2H₂O (88 mg) was obtained as colorless crystals.

melting point: >240° C. (decomposition).

optical rotation $[\alpha]_D^{23}$=+23.3 (c=0.5, H₂O).

$^1$H-NMR(400 MHz, DMSO-d$_6$) δ=2.60–2.70(m, 1H), 2.70–2.80(m, 1H), 3.69(br.t, J=12 Hz, 1H), 3.85(br.t, J=12 Hz, 1H), 4.00(s, 3H), 4.85(br.s, 1H), 7.84(br.s, 1H), 8.05(s, 1H), 8.17(d, J=6 Hz, 2H), 8.74(d, J=6 Hz, 2H), 9.12(br.s, 3H), 11.64(br.s, 1H).

FORMULATION EXAMPLE 1

Tablets

| | |
|---|---|
| Inventive compound | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The inventive compound, lactose, corn-starch and crystalline cellulose were mixed, kneaded with polyvinylpyrrolidone K30 paste solution and passed through a 20-mesh sieve for granulation. After drying at 50° C. for 2 hrs, the granules were passed through a 24-mesh sieve, and talc and magnesium stearate were added. Using a φ7 mm punch, tablets weighing 120 mg per tablet were prepared.

FORMULATION EXAMPLE 2

Tablets

| | |
|---|---|
| Inventive compound | 10.0 mg |
| Lactose | 70.0 mg |
| Corn starch | 35.0 mg |
| Polyvinylpyrrolidone K30 | 2.0 mg |
| Talc | 2.7 mg |
| Magnesium stearate | 0.3 mg |
| | 120.0 mg |

The compound of the present invention, lactose and corn starch were mixed, kneaded with Polyvinylpyrrolidone K30 paste solution and passed through a 20-mesh sieve for granulation. After drying at 50° C. for 2 hrs, the granules were passed through a 24-mesh sieve, and talc and magnesium stearate were mixed. The mixture was filled in hard capsules (No. 4) to give capsules weighing 120 mg.

The pharmacological action of the pharmaceutical agent of the present invention is explained in the following by way of experimental examples.

EXPERIMENTAL EXAMPLE 1

Rho Kinase Inhibitory Activity (Inhibition of Bovine Aorta Thoracia Rho Kinase)

The Rho kinase was prepared from bovine aorta of thorax by partial purification as in the following. The artery was minced and homogenized with a 9-fold amount of 50 mM Tris-hydroxymethylaminomethane (Tris) (pH=7.4), 1 mM dithiothreitol, 1 mM EGTA, 1 mM EDTA, 100 μM p-amidinophenylmethylsulfonyl fluoride, 5 μM E-64, 5 μM leupeptine and 5 μM pepstatin A. The homogenate was centrifuged (10,000×g, 30 minutes) to give a supernatant. The supernatant was adsorbed onto a hydroxyapatite column. The column was washed with 0.2 M phosphate buffer (pH=6.8). The standard product of Rho kinase was eluted with 0.4 M phosphate buffer (pH=6.8). The Rho kinase was assayed as follows.

A reaction mixture (total amount 50 μl) containing 50 mM Tris, 1 mM EDTA, 5 mM $MgCl_2$, 50 μg/ml histone, 10 μM GTPγS, 100 μg/ml Rho, 2 μM [$^{32}$P]ATP, the Rho kinase (3 μl) prepared in the above and the test compound was reacted at 30° C. for 5 minutes. The reaction was terminated by the addition of 25% trichloroacetic acid (TCA) solution (1 ml) and the mixture was stood at 4° C. for 30 minutes. Then, the mixture was filtered through a membrane filter (HAWP type, Millipore), and the radioactivity of the filter was counted on a liquid scintillation counter. The inhibitory activity of the test compound was calculated from the following formula based on the comparison of the radioactivity with the sample without the test compound (control). The results are shown in Table 1.

$$\text{Inhibition (\%)} = \frac{\text{cpm under control} - \text{cpm in the presence of test compound}}{\text{cpm under control}} \times 100$$

EXPERIMENTAL EXAMPLE 2

Rho Kinase Inhibitory Activity (Inhibitory Activity on Human Rho Kinase)

Human Rho kinase was prepared as follows. Using the following primer prepared based on the human ROCK-1 cDNA sequence reported by Ishizaki et al. (T. Ishizaki et al. EMBO J. 15, 1885–1893, 1996) and Human Placenta cDNA (Clontech, Lot. 7030086) as a template, PCR amplification was carried out.

```
primer No. 1:
CC GAGCTCC ATG TCG ACT GGG GAC AGT TTT GAG   (Seq. Listing SEQ ID No:1)
   Sac I primer No. 2:
TAGCGGCCGC ACT AGT TTT TCC AGA TGT ATT TTT G (Seq. Listing SEQ ID No:2)
   Not I
```

The amplified DNA fragment was digested with Sac I and Not I, and inserted into the Sac I/Not I site of a commercially available vector for insect cell expression, pBAC-1 (Novagenn), whereby a full-length human ROCK-1 protein expression vector was prepared. For preparation of a vector that expresses the kinase domain (1 to 477 amino acids) of the ROCK-1 protein, the full-length protein expression vector was digested with Xba I/Xho I to remove the C-terminal region of the human ROCK-1 cDNA, and a DNA linker, enclosed with a square in FIG. 1, was inserted thereinto and treated, whereby a vector that expresses human ROCK-1 kinase domain (1 to 477 amino acids) having the His-Tag sequence of FIG. 1 added to the C-terminal was prepared.

The kinase domain expression vector prepared above was used to prepare a recombinant baculovirus for kinase domain expression using BacVector-1000 Transfection Kits (Novagen). For expression of a protein, Sf9 cell was infected with a recombinant virus so that MOI=10, and incubated in a commercially available medium (Sf-900II SFM+5% FBS+ penicillin-streptomycin, GIBCO BRL) at 28° C. for 3 days.

After the incubation, the cells were recovered by centrifugal separation, homogenized in a lysis buffer (20 mM Tris-Cl, pH=8.0, 0.5 mM DTT, 0.1% Triton X-100, 300 mM NaCl, 2 mM imidazole, 0.5 mM EDTA, 1 mM benzamidine, 1 μg/ml leupeptin, 1 μg/ml pepstatin A, 1 μg/ml aprotinin, 0.1 mM PMSF), and subjected to centrifugal separation to give a supernatant. The expressed protein was purified from the supernatant using an Ni-chelate affinity column (Qiagen) utilizing the His-Tag sequence added to the C-terminal side of the expressed protein.

The human Rho kinase assay was performed as follows. A 96 well microplate (trade name: Flash Plate, NEN) coated with a plastic scintillator was used as a reaction vessel. To coat histone used as a substrate, 100 μl of phosphate buffered saline containing histone (final concentration of histone 2.5 μg/ml) was added and the mixture was stood at room temperature for 1 hr. The solution in the plate was discarded and 300 μl of phosphate buffered saline containing 0.01% bovine serum albumin was added and discarded. This was repeated three times.

A reaction mixture (total amount 100 μl) containing 20 mM (N-morpholino)propanesulfone acid-NaOH (pH 7.2), 0.1 mg/ml bovine serum albumin, 5 mM dithiothreitol, 10 mM β-glycerophosphoric acid, 50 μM sodium vanadate, 10 mM magnesium chloride, 1 μM [$^{32}$P] ATP, Rho kinase prepared by the above-mentioned method and the test compound was allowed to react at room temperature for 20 min. The reaction was stopped by adding 0.7% phosphoric acid solution (100 μl) and the plate was washed three times. Then, the radioactivity incorporated into the substrate was measured using a liquid scintillation counter. The inhibitory activity (% inhibition) of the test compound was calculated from the following formula wherein the percent inhibition when the test compound was not added was 0%, and the percent inhibition when the enzyme was not added was 100%. In addition, the IC$_{50}$ value was determined using 4 or 5 points sandwiching 50% percent inhibition of the obtained percent enzyme inhibition, by nonlinear regression.

(calculation formula 1)

Percent inhibition (%) =

{1 − (assay value of compound − assay value without enzyme addition)/

(assay value without enzyme inhibitor − assay value without enzyme)} × 100

TABLE 1

| compound | Rho-kinase inhibitory activity (ROCK-1) IC$_{50}$ (nM) |
|---|---|
| Example 10 | 13 |

INDUSTRIAL APPLICABILITY

The results of the above-mentioned pharmacological tests have revealed that the compound of the formula (I) has a superior Rho kinase inhibitory action. From this, the compound of the formula (I), an isomer thereof and a pharmaceutically acceptable salt thereof of the present invention are useful as an anticancer drug, a suppressive agent of metastasis of cancer, a suppressive agent of angiogenesis, an antihypertensive, an anti-pulmonary hypertension drug, an anti-angina pectoris drug, a cerebrovascular contraction suppressive agent, an anti-asthma drug, a peripheral circulation-improving drug, an early delivery-preventive drug, an anti-arteriosclerosis drug, a suppressive agent of angiostenosis, an anti-inflammatory agent, an analgesic, an immunosuppressant, a suppressive agent of autoimmune disorder, an anti-AIDS drug, an inhibitor of fertilization and implantation of fertilized egg, a bone formation-promoting drug, a bone resorption inhibitor, a therapeutic agent of retinopathy, a therapeutic agent of glaucoma, a nerve axon-regenerating drug, a brain function-improving drug, a preventive of cell infection of digestive tract, a suppressive agent of fibrosis of various organs, a therapeutic agent of erectile dysfunction and an agent for the prophylaxis or therapy of ischemia-reperfusion injury.

This application is based on a patent application No. 2000-074764 filed in Japan, the contents of which are hereby incorporated by reference.

SEQUENCE LISTING FREE TEXT

Sequence listing SEQ ID No:1: Oligonucleotide designed to act as primer for PCR.

Sequence listing SEQ ID No:2: Oligonucleotide designed to act as primer for PCR.

Sequence listing SEQ ID No:3: DNA sequence of part of expression vector of human ROCK-1 kinase domain having His-Tag sequence added to C-terminal.

Sequence listing SEQ ID No:4: Complementary strand to DNA sequence of Sequence listing SEQ ID No:3

Sequence listing SEQ ID No:5: Amino acid sequence of part of human ROCK-1 kinase domain having His-Tag sequence added to C-terminal.

What is claimed is:

1. An amide compound of the formula

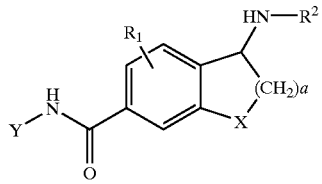
(I)

wherein

R$^1$ is hydrogen, alkyl, cycloalkyl, halogen, hydroxyl, alkoxy, haloalkyl, hydroxyalkyl, aralkyl, acyl, alkoxycarbonyl, alkylcarbamoyl, alkylsulfone, nitro, amino optionally having substituents selected from the group consisting of alkyl having 1 to 4 carbon atoms, acyl having 1 to 4 carbon atoms and benzoyl, cyano or phenyl;

R$^2$ is hydrogen, alkyl, cycloalkyl, phenyl or aralkyl, or a group represented by the formula (II)

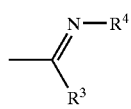
(II)

in the formula (II), R$^3$ is hydrogen, alkyl or amino optionally having substituents selected from the group consisting of alkyl having 1 to 4 carbon atoms, acyl having 1 to 4 carbon atoms and benzoyl, and R$^4$ is hydrogen, alkyl, aralkyl, phenyl, nitro or cyano, or R$^3$ and R$^4$ may be bonded to form a heterocyclic ring selected from the group consisting of imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl, benzoimidazol-2-yl, benzothiazoi-2-yl and benzooxazol-2-yl, which may have substituents selected from the group consisting of halogen, alkyl, alkoxy, haloalkyl, nitro, amino, phenyl and aralkyl;

a is an integer of 1 to 4;

X is S or SO$_2$; and

Y is a group of the formula (III), (IV), (V) or (VI):

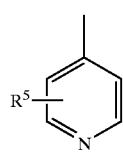
(III)

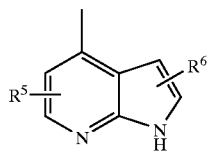
(IV)

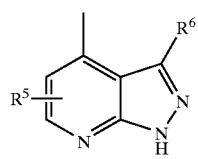
(V)

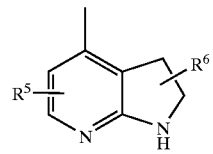
(VI)

in the formulas (III), (IV), (V) and (VI), R$^5$ and R$^6$ are the same or different and each is hydrogen, alkyl, cycloalkyl, phenyl, halogen, hydroxyl, alkoxy, alkoxyalkyl, nitro, amino optionally having substituents selected from the group consisting of alkyl having 1 to 4 carbon atoms, acyl having 1 to 4 carbon atoms and benzoyl or cyano, a geometrical isomer thereof or an optical isomer thereof or a pharmaceutically acceptable salt thereof.

2. The amide compound of claim 1, wherein, in the formula (I), R$^1$ is hydrogen, alkyl, halogen, bydroxyl, alkoxy, nitro, amino optionally having substituents selected from the group consisting of alkyl having 1 to 4 carbon atoms, acyl having 1 to 4 carbon atoms and benzoyl or cyano; R$^2$ is hydrogen; a is an integer of 1 to 3; X is S or SO$_2$; and Y is a group of the formula (III), (IV) or (V), wherein R$^5$ and R$^6$ in the formulas (III), (IV) and (V) are the same or different and each is hydrogen, alkyl, halogen, hydroxyl, alkoxy, nitro, amino optionally having substituents selected from the group consisting of alkyl having 1 to 4 carbon atoms, acyl having 1 to 4 carbon atoms and benzoyl or cyano, a geometrical isomer thereof or an optical isomer thereof or a pharmaceutically acceptable salt thereof.

3. The amide compound of claim 2, which is selected from the group consisting of
(S)-4-amino-N-(4-pyridyl)thiochromane-7-carboxamide,
(S)-4-amino-N-(4-pyridyl)thiochromane-7-carboxamide 1,1-dioxide,
(S)-4-amino-N-(1H-pyrazolo[3,4-b]pyridin-4-yl)thiochromane-7-carboxamide,
(S)-4-amino-N-(1H-pyrazolo[3,4-]pyridin-4-yl)thiochromane-7-carboxamide 1,1-dioxide,
(S)-4-amino-N-(1H-pyrrolo[2,3-b]pyridin-4-yl)thiochromane-7-carboxamide and
(S)-4-amino-N-(1H-pyrrolo[2,3-b]pyridin-4-yl)thiochromane-7-carboxamide 1,1-dioxide,
a geometrical isomer thereof or an optical isomer thereof or a pharmaceutically acceptable salt thereof.

4. The amide compound of claim 2, which is selected from the group consisting of
(S)-4-amino-6-methyl-N-(4-pyridyl)thiochromane-7-carboxamide,
(S)-4-amino-6-methyl-N-(4-pyridyl)thiochromane-7-carboxamide 1,1-dioxide,
(S)-4-amino-6-chloro-N-(4-pyridyl)thiochromane-7-carboxamide,
(S)-4-amino-6-chloro-N-(4-pyridyl)thiochromane-7-carboxamide 1,1-dioxide,
(S)-4-amino-8-methyl-N-(4-pyridyl)thiochromane-7-carboxamide,
(S)-4-amino-8-methyl-N-(4-pyridyl)thiochromane-7-carboxamide 1,1-dioxide,
(S)-4-amino-6-methyl-N-(1H-pyrrolo[2,3-b]pyridin-4-yl)thiochromane-7-carboxamide 1,1-dioxide and
(S)-4-amino-6-chloro-N-(1H-pyrrolo[2,3-b]pyridin-4-yl)thiochromane-7-carboxamide 1,1-dioxide,
a geometrical isomer thereof or an optical isomer thereof or a pharmaceutically acceptable salt thereof.

5. A pharmaceutical composition comprising the amide compound of claim 1, a geometrical isomer thereof or an optical isomer thereof or a pharmaceutically acceptable salt thereof, and a pharmaceutically acceptable carrier.

6. A method for treating hypertension, comprising administering a pharmaceutically effective amount of a Rho kinase inhibitor to a patient in need thereof, wherein the Rho kinase inhibitor comprises the amide compound of claim 1, a geometrical isomer thereof or an optical isomer thereof or a pharmaceutically acceptable salt thereof.

7. A method for treating cerebrovascular contraction, comprising administering a pharmaceutically effective amount of a Rho kinase inhibitor to a patient in need thereof, wherein the Rho kinase inhibitor comprises the amide compound of claim 1, a geometrical isomer thereof or an optical isomer thereof or a pharmaceutically acceptable salt thereof.

* * * * *